United States Patent
Estrada Ramirez et al.

(10) Patent No.: US 10,555,986 B2
(45) Date of Patent: Feb. 11, 2020

(54) DIETARY SUPPLEMENT DERIVED FROM NATURAL PRODCUTS BY HOT MELT EXTRUSION (HME) PROCESSING

(71) Applicants: Omar Augusto Estrada Ramirez, Antioquia (CO); Laura Restrepo Uribe, Medellin (CO); Maria del Pilar Noriega Escobar, Medellin (CO); Katalina Muñoz Durango, Medellin (CO); Catalina María Álvarez Ramírez, Antioquia (CO); Juan Camilo Mazo Rivas, Medellin (CO); Lucas Penagos Vélez, Antioquia (CO)

(72) Inventors: Omar Augusto Estrada Ramirez, Antioquia (CO); Laura Restrepo Uribe, Medellin (CO); Maria del Pilar Noriega Escobar, Medellin (CO); Katalina Muñoz Durango, Medellin (CO); Catalina María Álvarez Ramírez, Antioquia (CO); Juan Camilo Mazo Rivas, Medellin (CO); Lucas Penagos Vélez, Antioquia (CO)

(73) Assignees: INSTITUTO DE CAPACITACIÓN E INVESTIGACIÓN DEL PLÁS, Medellin (CO); COMPAÑÍA NACIONAL DE CHOCOLATES, S.A.S., Medellin (CO)

( * ) Notice: Subject to any disclaimer, the term of this patent is extended or adjusted under 35 U.S.C. 154(b) by 120 days.

(21) Appl. No.: 15/934,288

(22) Filed: Mar. 23, 2018

(65) Prior Publication Data
US 2018/0271928 A1 Sep. 27, 2018

Related U.S. Application Data
(60) Provisional application No. 62/475,674, filed on Mar. 23, 2017.

(51) Int. Cl.
| | | |
|---|---|---|
| A61K 36/00 | (2006.01) | |
| A61K 36/8962 | (2006.01) | |
| A23L 27/12 | (2016.01) | |
| A23L 33/105 | (2016.01) | |
| A23L 27/10 | (2016.01) | |
| A23L 27/00 | (2016.01) | |
| A23L 27/16 | (2016.01) | |
| A23G 1/48 | (2006.01) | |
| A61K 9/48 | (2006.01) | |
| A61K 36/23 | (2006.01) | |
| A61K 36/31 | (2006.01) | |
| A61K 36/38 | (2006.01) | |
| A61K 36/45 | (2006.01) | |
| A61K 36/54 | (2006.01) | |
| A61K 36/63 | (2006.01) | |
| A61K 36/752 | (2006.01) | |
| A61K 36/87 | (2006.01) | |
| A61K 9/14 | (2006.01) | |

(52) U.S. Cl.
CPC ............ *A61K 36/8962* (2013.01); *A23G 1/48* (2013.01); *A23L 27/10* (2016.08); *A23L 27/105* (2016.08); *A23L 27/12* (2016.08); *A23L 27/13* (2016.08); *A23L 27/16* (2016.08); *A23L 27/74* (2016.08); *A23L 27/84* (2016.08); *A23L 33/105* (2016.08); *A61K 9/48* (2013.01); *A61K 36/23* (2013.01); *A61K 36/31* (2013.01); *A61K 36/38* (2013.01); *A61K 36/45* (2013.01); *A61K 36/54* (2013.01); *A61K 36/63* (2013.01); *A61K 36/752* (2013.01); *A61K 36/87* (2013.01); *A23V 2002/00* (2013.01); *A23V 2250/21162* (2013.01); *A23V 2300/16* (2013.01); *A61K 9/146* (2013.01)

(58) Field of Classification Search
CPC ...................................................... A61K 36/00
USPC ........................................................ 424/725
See application file for complete search history.

(56) References Cited

FOREIGN PATENT DOCUMENTS

WO    WO 2018127938    *    7/2018

* cited by examiner

*Primary Examiner* — Michael V Meller
(74) *Attorney, Agent, or Firm* — Isaac Angres

(57) ABSTRACT

The invention provides a composition rich in flavonoids based on natural extracts, comprising a flavonoid extract dispersed by melt mixing or extrusion and encapsulated in a polymer matrix. The invention is also a novel dietary supplement with the naturally occurring ingredient (−)-epicatechin, cacao extracted, that could potentially prevent or reduce the risk of Atherosclerotic pathology. The use of (−)-epicatechin is promising as a therapeutic agent due to its potential antioxidant activity and its diverse biological properties. (−)-Epicatechins are chemically unstable and extensively degraded in fluids of near neutral or greater pH, such as intestinal juice and bile. Current technologies used for taste masking and modified release as spray drying, liposome entrapment, co-crystallization, freeze drying, among others, suffer from numerous shortcomings, including poor repeatability and limitations on target delivery.

1 Claim, 45 Drawing Sheets

Crystallization of fatty acids

DIETARY SUPPLEMENT DERIVED FROM NATURAL PRODCUTS BY HOT MELT EXTRUSION (HME) PROCESSING

This application claims the priority benefit under 35 U.S.C. section 119 of U.S. Provisional Patent Application No. 62/475,674 entitled "Dietary Supplement Derived From Cacao By Hot Melt Extrusion (HME) Processing" filed on Mar. 23, 2017; which is in its entirety herein incorporated by reference.

FIELD OF THE INVENTION

The instant invention generally relates to dietary supplements derived from natural products made by the process of hot melt extrusion processing. The instant invention also relates to dietary supplements derived Cacao and made by the process of hot melt extrusion processing.

BACKGROUND OF THE INVENTION

Cardiovascular disease (CVD) represents the leading determinant of morbidity and mortality in both developed and underdeveloped countries. Studies suggest cardiovascular diseases (CVD) may be preventable by lifestyle modifications, such as stop smoking, exercise and nutrition. Given the consequences, cost and risks associated with CVD and its medical treatment, there is a need for nutritional intervention in order to prevent or reduce the occurrence of this condition. There are a number of synthetic drug formulations available to prevent atherosclerosis disease. Some examples are Statins, Colestipol, Clofibrate, Questran, Gemfibrozil, among others. However, they have high potential for side effects, including muscle pain, nausea, heartburn, hepatic dysfunction and gastrointestinal discomforts.

CVDs are the number 1 cause of death globally: more people die annually from CVDs than from any other cause. Estimates from the World Health Organization show that cardiovascular disease (CVD) accounted for approximately 17.5 million deaths in 2012 (approximately 31% of all global deaths). Of these deaths, an estimated of 7.4 million were due to coronary heart diseases and 6.7 million were due to strokes. In 2015 was estimated that 89.6 million people in Latin America were affected by any CVD.

CVD also represents a major economic burden on health care systems, in terms of direct (e.g., hospitalizations, rehabilitation services, physician visits, prescription drugs) and indirect costs associated with mortality and morbidity. For the year 2015, the first economic analysis was done in Latin America, showing that the CVD costs about 30.9 thousand millions dollars in the region.

A major factor in CVD is atherosclerosis, a process of accumulating plaques in blood vessels wall. This disease, very hard to treat and almost impossible to reverse, is highly preventable. The development of atherosclerosis is a multifactorial process in which endothelial dysfunction, inflammatory response, modified lipids and lipoproteins, and activated platelets all play significant roles in the process.

(−)-Epicatechin research has recently attracted great interest due to its potential health benefit to humans. In recent years, an increasing number of experimental and clinical studies suggests a protective effect of (−)-epicatechin at doses of 1 or 2 mg/kg of body weight against atherogenesis, oxidative stress, inflammation, and endothelial function. Moreover, publications sustained that (−)-Epicatechin may be effective and beneficial in the prevention and treatment of atherosclerosis.

Cacao beans are the fruit seed of the cacao tree (*Theobroma cacao*), which are found in warm, moist climates in areas about 20° latitude north and south of the equator, between 500 and 2000 meters above sea level.

Diseases negatively impact on world cacao production, causing considerable losses that can become 30% or more of the productive potential. Among the most potentially dangerous of these diseases are frosty pod (moniliasis), caused by *Moniliophthora roreri* (moniliasis), and witches' broom, caused by *Moniliophthora perniciosa*. Over the centuries, the use of cacao has evolved to what we now know as chocolate (processed bean in solid or liquid form containing varying percentages of cacao liquor, cacao butter, sugar, and milk). Numerous polyphenolic compounds are present in the cacao, in which flavonoids, anthocyanins and tannins are the major phenols. The compounds of particular interest in the present invention are flavanols, a subclass of flavonoids.

Cacao flavonoids are characterized as catechins (flavan-3-ols) and include the monomelic forms, (−)-epicatechin and (+)-catechin, and the oligomeric form procyanidins (also termed proanthocyanidins), which are polymeric compounds comprising catechin and epicatechin subunits. It has been reported that 60% of the total phenolic compounds in raw cacao beans are flavanol monomers (epicatechin and catechin) and procyanidins oligomers (dimer to decamer).

(−)-Epicatechin is a major component of the polyphenols in cacao beans and it comprises approximately 35% of the total phenolic content in unfermented Cacao beans. A study reported that flavonoid-enriched cacao powder contain 128.9 mg/g of procyanidins, and particularly 19.36 mg/g of (−)-epicatechin.

Suggestions regarding the existence of possible cacao-dependent health benefits are not an innovative concept. In the past, "*Theobroma cacao*" was frequently used as a medicine for various diseases, but its medical use progressively disappeared. In contrast to this, recent studies have demonstrated a potential and to a certain extent unanticipated and unexpected role of cacao in "promoting health". In fact, a large body of evidence supports that dietary intake of catechins might exert some beneficial vascular effects, reduce the risk of cardiovascular morbidity and mortality, and contribute to the prevention of other chronic diseases. A considerable number of epidemiological investigations have generated data that support an association between the intake of flavanol containing foods and a decreased risk of diseases, in particular cardiovascular ones. Researchers have evaluated the outcomes of 15 prospective cohort studies, which aimed at investigating the relationship between the intake of flavonoid containing foodstuffs and the risk of cardiovascular disease. Thirteen of these studies provided evidence supporting a positive correlation between the dietary intake of flavanols and cardiovascular health, with a reduction of cardiovascular disease mortality of up to 65%. Evidence indicates that (−)-epicatechin is the main cacao flavanol associated with cardiovascular effects. (−)-Epicatechin counteracts the action of oxidized LDL on endothelial cells, an action considered pivotal for endothelial dysfunction in the pathogenesis of atherosclerosis. Additionally, it improves the vascular function, lowers blood pressure and improves insulin sensitivity. These compounds reportedly act as free radical scavengers and inhibitors of eicosainoid biosynthesis; in model systems, they also reduce low-density lipoprotein oxidation, prevent platelet aggregation and protect the heart from ischemia injury.

(−)-Epicatechin in cacao quenches OH 100 times more effectively than mannitol, a typical OH scavenger. According to Norman Hollenberg, professor of medicine at Harvard Medical School, (−)-epicatechin can reduce the risk of four of the major health problems: stroke, heart failure, cancer and diabetes. He studied the Kuna people in Panama, who drink up to 40 cups of cacao a week, and found that the prevalence of the "big four" is less than 10%. He believes that (−)-epicatechin should be considered essential to the diet and thus classed as a vitamin. Interestingly, data from a population-based cohort study of 1,169 patients link chocolate consumption with decreased mortality after myocardial infarction.

Other studies have shown the effects of (−)-epicatechin on myocardial infarct size and left ventricular remodeling after permanent coronary occlusion. The results demonstrated the unique capacity of (−)-epicatechin to confer cardioprotection in the setting of a severe form of myocardial ischemic injury. Protection was sustained over time and preserved left ventricle structure and function. The cardioprotective mechanism(s) of (−)-epicatechin seemed to be unrelated to protein kinase B(AKT) or extracellular signal-related kinase (ERK) activation. Results yield a reduction in scar (infarct) size of approximately 33%.

A study has reported that the activity of (−)-epicatechin in endothelial cells modulates the endothelial nitric oxide synthase (eNOS) in a favorable direction by (i) preventing a proteasome-mediated loss of eNOS protein due to oxidatively modified low density lipoproteins (LDL) with concomitant protection of endothelial cells against oxidized low density lipoprotein mediated cell death, (ii) ameliorating endothelial nitric oxide (NO) production at the posttranslational level. The study concludes that (−)-epicatechin contribute to protect the integrity of endothelial cells not only by scavenging free radicals but also by maintaining endothelial NO synthase. Concluding that improving the function of the eNOS pathway may be effective and beneficial in the prevention and treatment of atherosclerosis.

Tolerance trials for a green tea catechin supplement have been carried out concluding that the optimum dosage to obtain the best health benefits from catechins was of 800 mg. This dosage is tolerated well by subjects undergoing an overnight fast. Other research reported that a consumption of a dose approached 500 mg of flavonoids may be beneficial in patients with atherosclerotic disease.

A ninety-three patients trial, administering 27 g/day of flavonoid-enriched chocolate containing 850 mg of flavan-3-ols and a content of 90 mg of epicatechin resulted in a significant reduction of peripheral insulin resistance and improvements in insulin sensitivity. Concluding that one year intervention with flavan-3-ols and isoflavones improved biomarkers of CVD risk, highlighting the additional benefit of flavonoids to standard drug therapy in managing CVD risk in postmenopausal type 2 diabetic patients.

The study suggested that epicatechin dose may be a key contributor. Doses of 50 mg epicatechin/day reduced systolic and diastolic blood pressure. For fasting glucose and triglycerides, beneficial effects were observed at only the 50-100-mg/day epicatechin dose. These findings support oral administration of pure (−)-epicatechin mimicking acute vascular effects.

Thus, one of the major pitfalls of (−)-epicatechins is that they are chemically unstable. In solution, they readily undergo oxidation, involving the loss of hydrogen atoms, the generation of a semiquinone radical intermediate and the formation of quinoneoxidised products. A number of factors, including oxygen concentration and pH, influence the stability of (−)-epicatechins. The most crucial factor in (−)-epicatechin degradation is pH; it has been shown that the rate of oxidation increases as the pH increases.

During heat treatment, nonenzymatic browning is developed through the Maillard reaction (MR), accompanied by the formation of a variety of MR products (MRPs). This reaction involves not only reducing sugars and amino acids but also carbonyl compounds resulting from lipidoxidation. Together with oxidation, condensation, and complexation of polyphenol compounds and following protein and starch hydrolysis, MR is responsible for the formation of the characteristic brown color, pleasant aroma, and texture of roasted cacao beans. It was established that MR is responsible for the decrease of reduced sugar and amino acid concentrations observed during the roasting of cacao beans. The reaction occurs extensively in food systems and in vivo. (−)-Epicatechins react with Maillard reactants in model systems; two main reaction products are reported, epicatechin-C5 and -C6 sugar fragment adducts and quenched 3-deoxy-2-hexosulose (a key source C6 to C1 sugar fragments) and consequently inhibited Maillard product formation.

(−)-Epicatechins are rapidly absorbed in the human body, however, their duration in plasma is considerably short and their excretion from the body appears to be fast. This instability has been cited as one of the reasons for the poor bioavailability of these compounds. The oral bioavailability of (−)-epicatechins is low, at less than 5%, with most of the catechin degradation believed to occur under the small intestine conditions where the elevated pH and the presence of reactive oxygen species provide favorable conditions for catechin auto-oxidative reactions.

Limited Transport of catechins in the intestine is due to the Multidrug Resistance Proteins (MRP) and P-glycoprotein (PgP,) known for limiting the uptake of catechins. Combined, poor intestinal transport and stability may result in limiting the absorption of catechins following oral consumption.

By additional way of background, U.S. Pat. No. 7,488,503 B1 relates to an encapsulation composition prepared in an extruder with water as a liquid plasticizer to be able to extrude the first polymer, the starch. The composition has a selected component from the group consisting of a sugar, a polyol, a corn syrup solid, and mixtures thereof. The second food polymer is at least one member selected from the group consisting of gum arabic, gum karaya, gum tragacanth, konjac, larch gum, locust bean gum, guar gum, xanthan gum, sodium carboxymethyl cellulose, agar agar, type A gelatin, type B gelatin, and mixtures thereof. The objective of the encapsulation is the flavoring agent.

U.S. Pat. No. 6,475,510 features a method for the preparation of a bite-dispersion tablets with the ability to disperse quickly in the mouth without the aid of water. The process comprises a dry granulation of one or more drugs blended with an excipient, flavors and a combination of a waxy material and phospholipid. The bite-dispersion tablet has an intense sweetener derived from fruit flavonoids for taste-masking.

WO/2008/086400 describes a method to produce a bioenhanced products by dry blending and solvent spray drying. In one embodiment the solubility-enhancing organic material is polymeric. The products describe by the invention include pharmaceuticals, nutraceuticals, cosmetic, and personal care products for man and animal.

US 2013/0046011 teaches a hot-melt extruded composition that includes about a plant-derived phenolic material, one or more edible or bioerodible excipients, a surface active material, an oral absorption enhancer, and one or more pharmaceutical or food grade additives. The composition has been hot-melt extruded at a temperature substantially below the melting point of the plant-derived phenolic material.

WO/2015/099842 relates to a nutritional composition for fortifying a hot beverage, or transform a hot beverage into an enhanced energy drink.

WO/2011/141708 discloses new particles comprising a tetracycline or one of its pharmaceutically acceptable salts and an antioxidant. Methods of encapsulation of a tetracycline or one of its pharmaceutically acceptable salts and an antioxidant could be spray drying or melt extrusion.

US 2007/0077279 features a composition containing at least a polyphenol and polyethylenlglycol, to product food, beverages, dietary supplements, feed, pharmaceuticals and personal care products. It describes the use of polyethylenglycol for masking the bitter taste of such polyphenols. The polyphenols are preferably selected from the group consisting of epigallocatechin gallate, resveratrol, hydroxytyrosol, oleuropein, polyphenols present in green tea extracts, catechins, polyphenols present in extracts of red grape skin, polyphenols present in olives and/or olive waste water, and their mixtures.

US 2015/0374019 relates to a formulations containing isomaltulose and a polyphenol. The same isomaltulose is used for masking unwanted taste components, in particular bitter substances in the formulations containing tea extracts.

A few delivery systems have been developed for catechins in recent years. One system is based on biodegradable photocured polyesters, from which the entrapped (−)-epigallocatechin-3-gallate, catechin from tea, was slowly released upon the erosion of the polymers, for preventing *Escherichia coli* biofilm formation. Another system used a chewing gum for the slow intake of catechins over a chewing period of about 30-40 min. However, little progress has been reported on an oral delivery system, which can sustainably release the entrapped catechins during digestion. The catechin or (−)-Epicatechins can be protected to prevent any degradation by the addition of ascorbic acid. The prior art is silent in that the protection can be achieved by encapsulation in a polymeric system with Hot Melt Extrusion (HME) technology.

Atherosclerotic pathology is very hard to treat and almost impossible to reverse, but is highly preventable. Given the consequences, cost and risks associated there is a need for nutritional interventions in order to prevent the occurrence of this condition.

OBJECTS OF THE INVENTION

The main objective of the invention is the development of nutraceutical formulations by using Hot Melt Extrusion (HME) which may be scaled and commercially launched either as a nutraceutical or pharmaceutical products or functional food ingredients.

The invention provides taste masking, characterization, stability and functionality of an encapsulated cacao extract, dissolution (incl. release) and other in-vitro tests required to demonstrate its efficiency. Another object of the invention is a food ingredient derived from cacao, with high content of procyanidins (epicathechin, catechin and other flavanols), by HME processing for taste masking.

A further object of the invention is to provide a dietary supplement with a potential for human use, using epichatechin as an active pharmaceutical ingredient, by HME processing.

SUMMARY OF THE INVENTION

Figure 1:
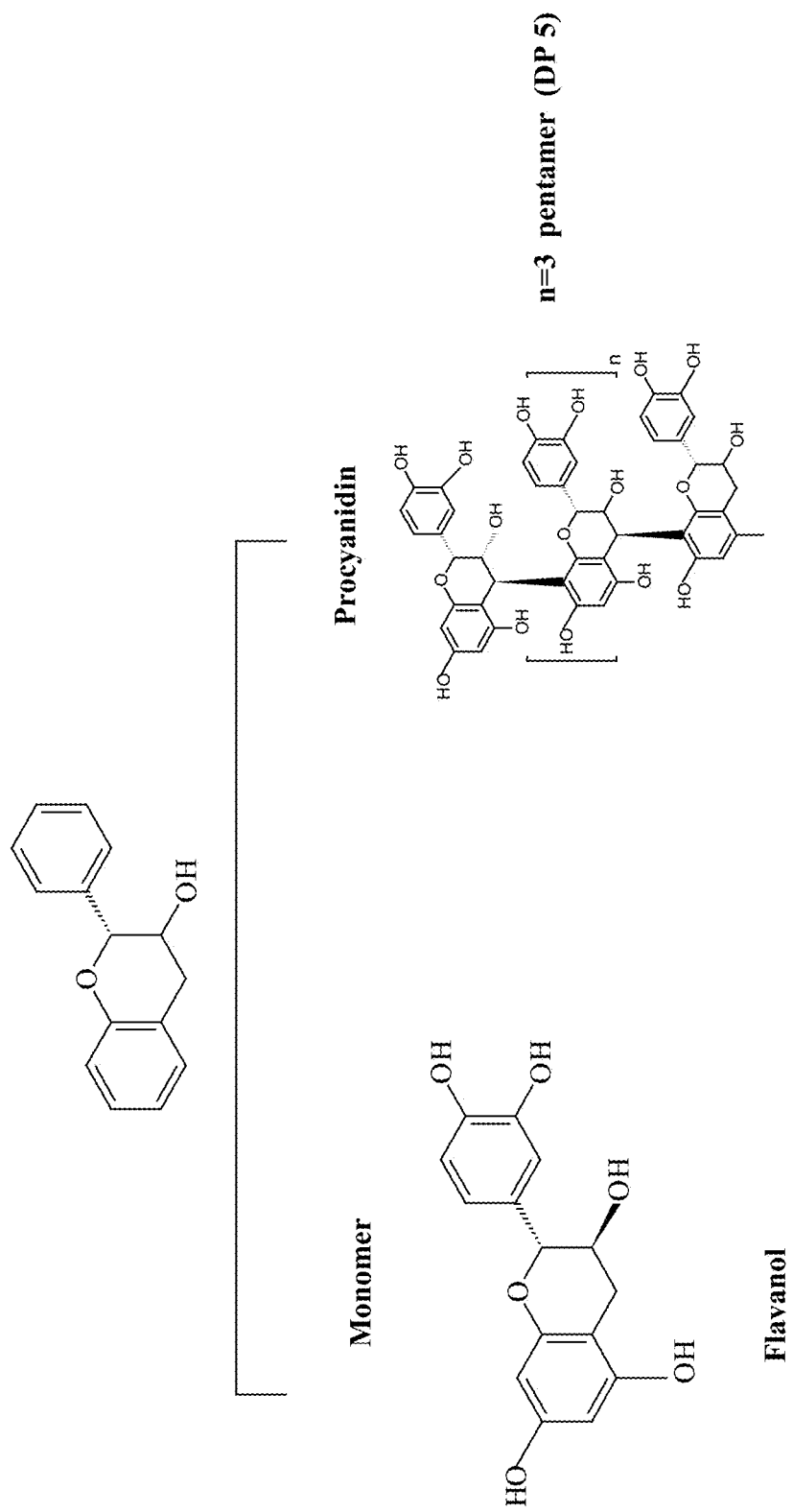
FIG. 1 shows the chemical structure of flavanols and procyanidin (DP5).

The invention is directed to a composition rich in flavonoids based on natural extracts, comprising a flavonoid extract dispersed by melt mixing or extrusion and encapsulated in a polymer matrix.

The invention also relates to a taste masking composition rich in flavonoids based on natural extracts, comprising a flavonoid extract dispersed by melt mixing or extrusion and encapsulated in a polymer matrix.

The invention is a novel dietary supplement with the naturally occurring ingredient (−)-epicatechin, cacao extracted, that could potentially prevent or reduce the risk of Atherosclerotic pathology. The use of (−)-epicatechin is promising as a therapeutic agent due to its potential antioxidant activity and its diverse biological properties. (−)-Epicatechins are chemically unstable and extensively degraded in fluids of near neutral or greater pH, such as intestinal juice and bile. Current technologies used for taste masking and modified release as spray drying, liposome entrapment, co-crystallization, freeze drying, among others, suffer from numerous shortcomings, including poor repeatability and limitations on target delivery.

In order to modify the rate of release and protect epicatechins from degradation in the gastrointestinal tract, polymeric systems such as polyvinyl caprolactam-polyvinyl acetate-polyethylene glycol graft copolymer, polyvinyl acetate-povidone copolymer, methacrylic acid-methyl methacrylate copolymer, ethylcellulose, among others, could be used as carriers. This would provide benefits such as protection from rapid degradation, modified release and prolonged duration of bioactive agents.

The instant invention provides a product made by hot melt extrusion for oral consumption containing a bioactive compound such as epicatechin, cacao extract. Furthermore, nutraceutical formulations rich in flavonoids or other sort of antioxidants have been developed by using Hot Melt Extrusion (HME) or continuous melt mixing techniques. The corresponding compound consist of about 30-60% wt. of natural extract and polymers GRAS type (Generally Regarded as Safe) as taste masking and release agents.

The formulations have to be extruded at a temperature substantially below the melting point of the interest molecules which guaranties that a significant degradation of these molecules does not occur. In order to monitor any possible chemical and thermal change on the formulations, the samples ought to be characterized by using different techniques, such as simple and Oxidative Induction Times Testing (OIT), Differential Scanning calorimetry (DSC), Thermogravimetric analysis (TGA); likewise, chemical evaluations may be carried out by using chromatographic and spectrophotometric techniques.

The invention also provides a food ingredient derived from cacao, with high content of procyanidins (epicatechin, catechin and other flavanols), by HME processing for taste masking. The invention further provides a dietary supplement for human use, using epichatechin as an active pharmaceutical ingredient, by HME processing.

The invention provides nutraceutical formulations by using Hot Melt Extrusion (HME) which may be scaled and commercially launched either as a nutraceutical or pharmaceutical products or functional food ingredients.

The present invention is also directed to a novel dietary supplement or food additive with the naturally occurring ingredient (−)-epicatechin and catechins extracted from cacao, that could potentially prevent or reduce the risk of the atherosclerotic pathology. The structures of cathechins are of the family having structures such as:

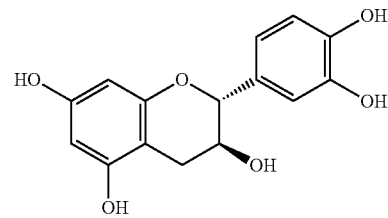 [SMILES: Oc1cc(O)c2c(c1)O[C@H](c1ccc(O)c(O)c1)[C@@H](O)C2]

DETAILED DESCRIPTION OF THE INVENTION

The pharmaceutical industry is facing two main problems, having poorly soluble drugs that require an increased dosage formulation so the proper drug absorption can be guaranteed, and the low bioavailability of the drug due to deficient dissolution during its passage through the gastrointestinal tract. Different approaches can be applied to overcome the solubility and bioavailability problems. One of them is manufacturing of solid dispersions; systems where one component, such as an API, is dispersed in a carrier, usually polymeric, and where the whole system appears to be in a solid state.

There are different types of solid dispersions, but only 3 can be achieved by HME, crystalline solid dispersion, amorphous solid dispersion, and solid solutions. Crystalline solid dispersions are systems wherein the crystalline drug substance is dispersed into an amorphous carrier matrix. The Differential Scanning calorimetry (DSC) profile for such a system is characterized by the presence of a melting endotherm (Tm) corresponding to the crystalline API and a characteristic glass transition temperature (Tg) corresponding to the amorphous carrier. They are generally designed to achieve controlled drug release profiles for highly soluble drugs.

Amorphous solid dispersions result when a melt extruded drug-polymer mixture is cooled at a rate that does not allow the drug to recrystallize or processed at temperatures at which the drug melts but remains immiscible with the carrier. The DSC profile for this system is characterized by the presence of two Tg. They have a potential to revert to the more stable crystalline form. In a solid solution, the drug molecule is molecularly dissolved in the polymeric carrier matrix and exhibits a single Tg. An amorphous solid solution is a pharmaceutically desirable single-phase system preferably including an amorphous polymer as the carrier, a drug in its high-energy state, as well as other excipients such as processing aids, recrystallization inhibitors, and wetting agents. A better understanding of the structure of a solid dispersion, particularly the existing physical form of a drug in the polymer excipient is necessary to predict the stability, solubility and hence bioavailability of melt extrudates.

Hot-Melt Extrusion (HME) is a recognized process that has been used in the last two decades for the manufacturing of solid dispersions. It has become very popular in the pharmaceutical field because it is a continuous process, solvent free, easy to clean and can be used for the preparation of different drug delivery systems; including granules, pellets, sustained released tablets, suppositories, stents, ophthalmic inserts, and transdermal and transmucosal delivery systems. Since it is a continuous process, fewer steps are involved resulting in lower cost of production.

HME is a process where a material that melts or softens under elevated temperatures and pressures is forced through an orifice by screws to produce polymeric products of uniform shape and density. It is carried out using an extruder, a barrel containing one or two rotating screws that transport material down the barrel. Optimization of process parameters, characterization and performance evaluation of the product, and assessment of its stability are inevitable tasks for successful application of HME in pharmaceutical formulations. The solid dispersion can be analyzed by different techniques such as Differential Scanning calorimeter (DSC), Thermogravimetric Analysis (TGA), rheometry, X-Ray Diffraction (XRD), and microscopy, among others. One of the challenges of generating solid dispersions with HME is the tendency of the API to recrystallize after the temperature drops from elevated processing temperature to room temperature. Different strategies can be employed to address the recrystallization issue, for example, if the goal is to improve bioavailability of the drug via increasing the APIs dissolution rate, then choosing appropriate excipients and/or optimizing the HME process is needed to improve the drug-polymer miscibility or dramatically slow down the recrystallization rate.

For HME applications, the polymer excipient has to present thermoplastic characteristics, it must be thermally stable at the extrusion temperature employed, the Tg should be between 50 and 180° C., it should exhibit low hygroscopicity to avoid crystallization, and it has to be no toxic.

Hot-stage microscopy (HSM), DSC and rheological analysis can be used to measure HME processing temperatures and design HME process and formulations. Low Tm and Tg from the polymeric excipient enable the low temperature extrusion process and makes the solubility analysis easier since the phase separation and recrystallization (dissolution kinetics) are faster when compared to polymeric excipients with high Tg. However, fast kinetics are not desirable if the API recrystallization is what should be avoided. Theoretically, Tg can be calculated with Fox equation (Eq. 1)

$$\frac{1}{T} = \frac{w_1}{T_{g1}} + \frac{w_2}{T_{g2}} \qquad \text{(Eq. 1)}$$

if the sample is based on two components, where w1 and w2 refer to the weight fraction and Tg1 and Tg2 to the glass transition temperatures of drug and polymeric excipient, respectively. The Gordon Taylor equation has been applied as well to drug-polymer samples to study the miscibility of the binary components.

It has been shown that the dissolution behavior of HME solid dispersion depends on the physicochemical characteristics of the excipient(s) applied, therefore, the choice of excipients plays an important role in a successful formulation. Different polymers as excipients can be employed to prepare immediate and sustained release dosage forms via HME. Polyethylene oxide (PEO), polyethylene glycol (PEG), polyvinylpyrrolidone (PVP), hydroxypropyl methyl cellulose (HPMC), hydroxypropyl cellulose (HPC), vinylpyrrolidone-vinylacetate copolymer (Kollidon® VA 64), dimethylaminoethyl methacrylate copolymer (Eudragit® E), PEG 6000-vinyl caprolactam-vinylacetate copolymer, and polyvinylcaprolactam-polyvinyl acetate-polyethylene glycol graft co-polymer (Soluplus®) can be used as immediate release (IR) polymeric excipients. On the other hand, ethylene vinyl acetate (EVA), polyvinyl acetate (PVA), polyL-lactic acid (PLA), polylactic-co-glycolic acid (PLGA), polycaprolactone, silicone, ammonium methacrylate copolymer (Eudragit® RS/RL), polyvinyl acetate-polyvinylpyrrolidone (Kollidon SR), and lipid matrices (microcrystalline wax, stearic acid, carnauba wax, etc.) can be used as sustained release (SR) polymeric excipients.

The most suitable pair (API-excipient or API-excipient combination IR/SR) can improve the drug release profile, and samples that have a more sustained release because they are less porous and have better mechanical properties can be produced by HME.

Figure 2:
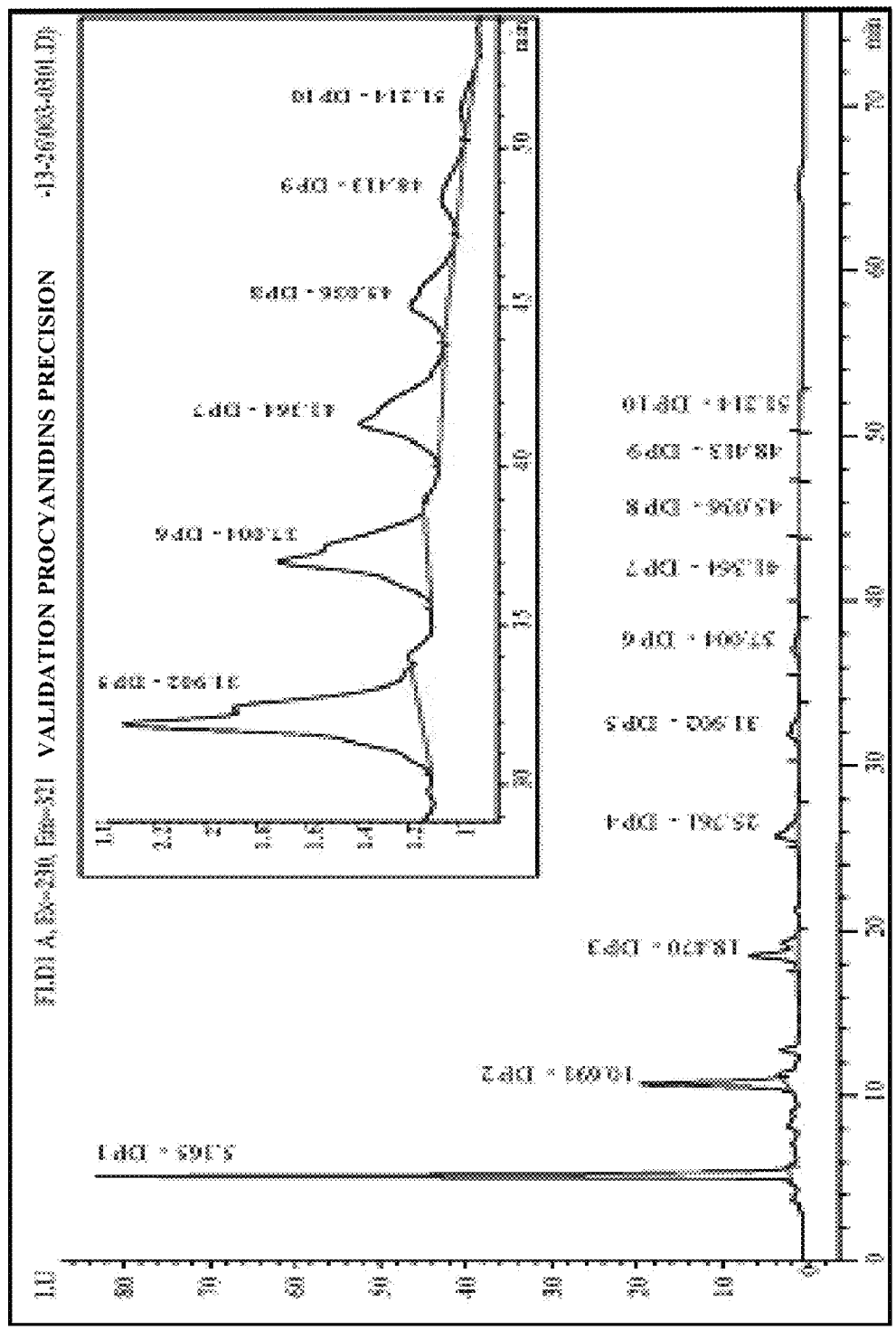
FIG. 2 illustrated the chromatograpic profile by HPLC for the reference material.

Little is found in the literature concerning API solubility in a polymeric excipient after HME processing and storage at a given temperature. Some researchers have used HSM, DSC and rheological analysis to characterize acetaminophen dissolution in PEO. The samples were prepared with increasing loads of acetaminophen and by the HME process. FIG. 2 shows the different temperatures of acetaminophen dissolved in PEO; this diagram can be interpreted as a "phase diagram". In region A acetaminophen and PEO form a liquid solution and are fully miscible, in region B acetaminophen does not totally dissolve and there are solid drug particles.

Therefore, it is more favorable to process acetaminophen-PEO formulations in region A. In region C (solid dispersion region) acetaminophen can molecularly disperse in PEO and it can partially recrystallize. This kind of "phase diagram" is very useful because valuable information can be obtained to formulate and develop the HME process; it is based on the API dissolution in the polymer excipient at different temperatures and increasing the API loading dose.

Hydrophobic excipients including polyvinylpyrrolidone and polyvinylpyrrolidone-co-vinyl acetate, polyethylene glycols, poly-ethylene oxides, some celluloses, polymethacrylate derivatives and a polyvinyl caprolactam-polyvinyl acetate-polyethylene glycol graft copolymer (Soluplus®) have been used to enhance the solubility and bioavailability of poorly water soluble active ingredients using HME techniques.

The polymers showing their physical properties in Tables 1-4 are particularly suitable for the invention.

TABLE 1

| Polymer | Tm (° C.) | Tg (° C.) | Tdeg (° C.) | Density (g/cm$^3$) |
|---|---|---|---|---|
| Extracto de cacao | | | ~200 | 1.2 |
| (−)-Epicatechin 90% | ~242 | | ~260 | |
| Aqualone EC-N7 | | 123.75/164.32/196.70 | ~255 | 1.14 |
| Kollidon SR | | 42.56 | ~220 | 1.2 |
| Soluplus | | 77.29 | ~270 | 1.082 |
| Eudragit L100 | | 81.24 | ~250 | 11.887 |
| Ethocel Standard 10 | 174.95 | 127.61 | ~220 | 1.251 |
| Klucel EF | 192.03 | | ~247 | 1.296 |

TABLE 2

| Chemical name | Commercial name | Tm (° C.) | Tg (° C.) | Tdeg (° C.) |
|---|---|---|---|---|
| Polyvinylpyrrolidone | Kollidon 12PF | N.A. | ~90 | ~225 |
| Vinylpyrrolidone-vinyl acetate copolymer | Kollidon VA 64 | N.A. | ~101 | ~238 |
| Polyethylene glycol | PEG 3350 | ~53-57 | | |
| Polyvinyl acetate-Polyvinylpyrrolidone | Kollidon SR | | 42.56 | ~220 |
| Hydroxypropyl Methylcellulose Acetate Succinate | Aqoat AS-HG | 57.1 | 135 | 218.8 |
| Methylcellulose | Metolose 60SH | | ~163 | ~280-300 |
| Hydroxy propyl cellulose | Klucel HF. GF, LF | | 100-150 | >250 |
| Coplymer of N-vinyl-2-pyrrolidone and vinyl acetate | Plasdone S-630 | | 109-112 | >300 |
| Ethylcellulose | Aqualon N7, N22 | N.A. | ~156 | >250 |
| Modified Starch | Starch 1500 | ~300 | | ~300 |
| Polylactic acid | PLA | ~155 | ~65 | ~250 |
| Methacrylic Acid-Methyl Methacrylate Copolymer | Eudragit L100/ Eudragit E PO | | 81.24 | ~250 |
| Ethylcellulose | Ethocel standard 10 | 174.95 | 127.61 | ~250 |

TABLE 3

| Chemical name | Commercial name | Tm (° C.) | Tg (° C.) | Tdeg (° C.) |
|---|---|---|---|---|
| Polyvinylpyrrolidone | Kollidon 12PF | N.A. | ~90 | ~225 |
| vinylpyrrolidone-vinyl acetate copolymer | Kollidon VA 64 | N.A. | ~101 | ~238 |
| Polyethylene glycol | PEG 3350 | ~53-57 | | |
| Polyvinyl acetate-polyvinylpyrrolidone | Kollidon SR | | 42.56 | ~220 |
| Hydroxypropyl Methylcellulose Acetate Succinate | Aqoat AS-HG | 57.1 | 135 | 218.8 |
| Methylcellulose | Metolose 60SH | | ~163 | ~280-300 |
| Hydroxy propyl cellulose | Klucel HF. GF, LF | | 100-150 | >250 |
| Coplymer of N-vinyl-2-pyrrolidone and vinyl acetate | Plasdone S-630 | | 109-112 | >300 |
| Ethylcellulose | Aqualon N7, N22 | N.A. | ~156 | >250 |
| Modified Starch | Starch 1500 | ~300 | | ~300 |
| Polylactic acid | PLA | ~155 | ~65 | ~250 |
| Methacrylic Acid-Methyl Methacrylate Copolymer | Eudragit L100/ Eudragit E PO | | 81.24 | ~250 |
| Ethylcellulose | Ethocel standard 10 | 174.95 | 127.61 | ~250 |

TABLE 4

| BASF | | TG | TM | MW | pH | RESTRICTIONS |
|---|---|---|---|---|---|---|
| KOLLIDON | VA 64 | 101 | — | 45K | independent | |
| | 30 | 149 | — | 50K | independent | |
| | 90 | 156 | | 1.25M | independent | |
| | CL | | | | | cross-linked |

TABLE 4-continued

| BASF | | TG | TM | MW | pH | RESTRICTIONS |
|---|---|---|---|---|---|---|
| KOLLICOAT | IR | 45 | 208 | 45K | independent | |
| | MAE 30 | | | | | emulsion |
| | MAE 100 | | | 250K | >5.5 | |
| | DP | | | | | |
| EVONIK | Protect | 45 | | 47K | <5.0 | |
| EUDRAGUAR | Control | | | | | emulsion |
| | Biotic | | | | | emulsion |

In its broadest aspect the invention provides the taste masking, characterization, stability and functionality of an encapsulated cacao extract, dissolution (including release) and other in-vitro tests required to demonstrate its efficiency.

The present invention provides a novel dietary supplement or food additive with the naturally occurring ingredient (−)-epicatechin and catechins extracted from cacao, that are particularly useful to prevent or reduce the risk of the atherosclerotic pathology.

In carrying out the instant invention, compounds rich in polyphenols (incl. cacao extract) are polymer encapsulated for taste masking and modified release. The product of the invention rich in polyphenols (incl. cacao extract) has modified release independent of particle size between 120 μm and 425 μm.

Similarly, the compound rich in polyphenols (incl. cacao extract) are polymer encapsulated for thermal stability and moisture resistance. The product of the invention containing compounds rich in polyphenols (incl. cacao extract) do not include taste masking agents or processing aids or flavor additives or sweeteners.

The formulations of the invention are made by continuous melt mixing process for manufacturing said compound rich in polyphenols with special screw configuration to guarantee dispersion and considering the low melting point of cacao extract (10-19° C.).

The product of the invention which includes compounds rich in polyphenols (incl. cacao extract) does not include coatings, crosslinking or chemical reactions affecting the said compound. The cacao extract of the invention is characterized as shown below.

Chemical Characterization of Cacao Extract

Flavanols and procyanidins are specific classes of flavonoids. Procyanidins are the oligomers of the monomeric flavanols (i.e., epicatechin and catechin) as shown in FIG. 1. The molecular weight of the flavanols oligomers is expressed as their degree of polymerization (DP). Separation based on DP permits the capture of the large structural diversity. Specifically, for cacao flavanols and procyanidins have been quantified up to a predefined molecular weight cut of DP=10 by summing oligomeric fractions DPI-DP10 (Robbins et al., 2012). Nevertheless, an additional method was used in order to quantify independently the monomers and xanthines. FIG. 1 illustrates the chemical structure of flavanols and procyanidin (DP5), modified from (Robbins et al., 2012).

The determination of flavanol and procyanidin (by degree of polymerization 1-10) content of cacao flavanol extract was also conducted. The determination of flavanol and procyanidins content of cacao extract was based on a normalized AOAC method. This methodology is applicable to the determination of flavanols and procyanidins (DP1-DP10) content of chocolate, cacao liquors, cacao powders and cacao extracts. The sum of monomeric (DP=1) and oligomeric fractions (DP2-DP10) is reported as the total procyanidins content.

Sample Preparation

The cacao extract was extracted with hexane to remove their lipid content components prior to extraction of flavanols and procyanidins. Flavanols and procyanidins (DP1-DP10) were extracted with an acidified aqueous acetone solvent system [acetone:water:acetic acid (AWAA). Then, the extract was passed through SPE cartridges Strata SCX, 55|im particle size and pore 70 A (Phenomenex 8B-S10-HBJ, California, Estados unidos), filtered and transferred to vials for normal-phase HPLC analysis. The method of calibration for this protocol was (−)-epicatechin and the relative response factors (RRFs) for DP2-10 (Table 5).

TABLE 5

Relative response factors for fractions DP1-DP10 under HPLC conditions (Robbins et al., 2012)

| Oligomeric fraction | Relative response factor |
|---|---|
| DP1 (monomers) | 1.0 |
| DP2 (dimers) | 0.374 |
| DP3 (trimers) | 0.331 |
| DP4 (tetramers) | 0.249 |
| DP5 (pentamers) | 0.237 |
| DP6 (hexamers) | 0.198 |
| DP7 (heptamers) | 0.169 |
| DP8 (octamers) | 0.139 |
| DP9 (nonamers) | 0.116 |
| DP10 (decamers) | 0.121 |

High Performance Liquid Chromatography-FLD Parameters

The identification, integration and quantification of the chromatographic signals were performed in a HPLC with fluorescence detector (FLD) (Agilent 1200). The column used was a Develosil Diol 100 A 250×4.6 mm, 5 p,m particle size (Phenomenex, Torrance, Calif.). Temperature of the oven was kept at 35° C. and the flow rate was 1 mL/min. The injection volume was 5|iL. The mobile phase consisted of acidic acetonitrile [(A) $CH_3CN$—HOAc, 98+2 (v/v)] and [(_,6)$CH_3OH$—$H_2O$—HOAc, 95+3+2 (v/v/v)]. The starting mobile phase condition was 7% B, 3 min; subsequently, ramp solvent B to 37.6% for 57 min and to 100% B, 3 min thereafter. The FLD was operated at $X_{excitation}$=230 nm $X_{emission}$=321 nm. Results are expressed in mg/g. In FIG. 2 is presented the chromatogram of the reference material NIST2381, DP1-DP10. NIST2381, DP1-DP10. FIG. 2 shows the chromatograpic profile by HPLC for the reference material DETERMINATION OF FLAVANOLS ((+)-CATECHIN AND (−)-EPICATECHIN) AND XANTHINES (THEOBROMINE AND CAFFEINE) CONTENT OF CACAO FLAVANOL EXTRACTS BY NORMAL PHASE HIGH-PERFORMANCE LIQUID Chromatography-FLD/DAD Based Method
Chemicals
Theobromine, caffeine, (+)-Catechin and (−)-Epicatechin were obtained from Sigma-Aldrich Co. (St. Louis, USA). Analytical grade reagents, such as solvents, were all chromatographic grade provided by Merck Millipore Co. (Darmstadt, Germany).
Sample Preparation To 1 g of dry extract was added 15 mL of extracted solution (Isopropanol/water 60:40; water pH: 9). Then the mixture was submitted to sonic bath to enhancing the extraction during 1 h at room temperature. The resulting solution was vortexing for 1 min and incubating for 1 h at −20° C. The obtained product was centrifuged (4000 rpm; 20 min) and 1 mL of supernatant was filtered (0.45 gm). An aliquot of 200 gL was added with a solution of acetic glacial 0.1% in a volumetric ball (2 mL) and 5 gL was injected in the HPLC.

High Performance Liquid Chromatography-FLD/DAD

The analytical method applied allows detecting and quantifying the flavanoles and xanthines content in fermented and/or roasted cacao beans. The identification, integration and quantification of the chromatographic signals were performed with an HPLC coupling with two detectors online, DAD (diode array detector) and FLD (fluorescence detector) (Agilent 1200). The FLD was operated at $X_{excitation}$=280 nm $X_{emission}$=315 nm and the DAD was operated at 280 nm. The quantification was performed by using the external standard method. The calibration curves were built for each standard as follows: 0.5-20 ppm for catechin; 5-200 ppm for epicatechin; 10-275 ppm for theobromine and 5-125 ppm for caffeine. The column used was a C18 Zorbax bonus HPLC Column (5 p,m particle size, L*I.D. 25 cm*4.6 mm). The results are expressed in mg/g.

TABLE 6

Compounds evaluated

| Compound | Formula | Chemical nomenclature |
|---|---|---|
| Theobromine | $C_7H_8N_4O_2$ | 3,7-dimetilxanthine |
| Caffeine | $C_8H_{10}N_4O_2$ | 1,3,7-trimetilxanthine |
| (+)-Catechin | $C_{15}H_{14}O_6$ | (2R,3S)-Catechin |
| (−)-Epicatechin | $C_{15}H_{14}O_6$ | (−)-Epicatechin (2R,3R) |

Results are summarized in table 7.

TABLE 7

Xanthines, flavanols and procyanidins in cacao extract (mg/g)

| Compound | Cacao extract Concentration (mg/g) M ± SD |
|---|---|
| Theobromine | 14.6 ± 0.2 |
| Caffeine | 2.30 ± 0.03 |
| (+)-Catechin | 6.52 ± 0.15 |
| (−)-Epicatechin | 21.30 ± 0.43 |
| Total Procyanidins (DP1-DP10) | 35.3 |

Additional extracts that can be used in the present invention includes:

*Vitis vinifera* Seeds and Skin Extract
Bioactive compounds: *Vitis vinifera* seeds standardized extracts contain approximately 15% of (+)-catechin and (−)-epicatechin, and 80% of proanthocyanidins of (−)-epicatechin 3-O-gallate, dimers, trimers, tetramers and their gallates and 5% of pentamers, hexamers, heptamers and their gallates.

Biological activity: Extracts have been tested in humans showing ability to reduce dyslipidemia markers, reduce blood pressure, reduce oxidative stress on LDL, help with weight management, improve skin conditions like chloasma, improve metabolic syndrome.

*Persea americana* Leaves, Peel and Seed Extract
Bioactive compounds: Flavanol monomers (catechin), proanthocyanidins, hydroxy-cinnamic acids (5-O-caffeoylquinic, 3-O-caffeoylquinic acid, 3-O-p-coumaroylquinic acid), and flavonol glycosides (quercetin derivatives) and procyanidin A trimers.

Biological activity: Avocado seeds may improve hypercholesterolemia, and be useful in the treatment of hypertension, hepatic inflammatory conditions and diabetes. Other activities are reported like amoebicidal, giardicidal, antimycobacterial, and antimicrobial.

*Allium cepa* Extract
Bioactive compounds: quercetin and quercetin glucosides, isorhamnetin glucosides, kaempferol glucoside, and, among anthocyanins, cyanidin glucoside. Also organosulphur compounds alliin. Biological activity: onion peel extract has the potential target in obesity by remodeling the characteristics of white fat to brown fat and controlling body weight. Promotes wound healing and improves the cosmetic appearance of postsurgical and hypertrophic scars. Also useful in the treatment of mild hypertension.

*Allium sativum* Extract
Bioactive compounds: quercetin and quercetin glucosides, isorhamnetin glucosides, kaempferol glucoside, and, among anthocyanins, cyanidin glucoside. Also organosulphur compounds allicin, ajoene, allicin, thiosulfinate, diallyl-di sulfide.

Biological activity: supported by clinical data as an adjuvant to dietetic management in the treatment of hyperlipidemia, and in the prevention of atherosclerosis. Also useful in the treatment of mild hypertension. Reduce symptoms associated with diabetes mellitus. Prevent inflammatory processes associated with asthma.

*Vaccinium oxycoccos* and *Vaccinium macrocarpon* Extract
Bioactive compounds: Proanthocyanidins (delphinidin), epicatechin, myricetin, and quercetin, chlorogenic and p-coumaric acid.

Biological activity: Cranberry fruit extracts (peel, seeds, pulp) may reduce the risk of symptomatic urinary tract infections in men and women.

*Nasturtium Officinale* Extract
Bioactive compounds: Phenyl isothiocyanates (PEITC), rutin.

Biological activity: Watercress plant extracts has been shown to reduce serum glucose, total cholesterol and LDL-cholesterol in diabetic rats, is also anti-inflammatory and antioxidant.

*Petroselinum crispum* Extract
Bioactive compounds: Apigenin, apigenin-7-O-glucoside or cosmosiin, apigenin-7-O-apiosyl-(1→2)-O-glucoside or apiin and the coumarin 2″,3″-dihydroxyfuranocoumarin or oxypeucedanin hydrate.

Biological activity: Parsley extract has been shown to be a good antioxidant activity, reduce hepatic steatosis in animal models.

*Vitis vinifera* Fruit and Red Wine Extract
Bioactive compounds: 4.32 mg epicatechin, 2.72 mg catechin, 2.07 mg gallic acid, 0.9 mg trans-resveratrol, 0.47 mg rutin, 0.42 mg epsilon-viniferin, 0.28 mg, p-coumaric acid, 0.14 mg ferulic acid and 0.04 mg quercetin per gram.

Biological activity: For its antioxidant activity improve endothelial function in patients with coronary heart disease. Also improves markers of cardiovascular disease.

Citrus Peel Extracts:

*Citrus reticulate, Citrus Sinensis, Citrus Limon* and *Citrus paradise.*

Bioactive compounds: Hesperidin, neohesperidin, narirutin, tangeretin, sinnesetina, nobiletin. Caffeic acid, p-coumaric acid, ferulic acid and sinapic acid.

Biological activity: A wide range of biological effects have been published for molecules derived from *citrus* peel extracts. For hesperetin (flavanone) studies showed the effect of dietary hesperetin on the hepatic lipid content and enzyme activities involved in triacylglycerol synthesis in rats. Hesperetin and naringenin improves coronary vasodilatation, decrease the platelets activity to clot the blood, and prevents LDLs from oxidizing. Hesperidin has anti-inflammatory activity in vitro. In neuroptrotection, hesperetin protects cortical neurons from oxidative injury. Hesperidin and neohesperidin at physiological (0.4-4.0 ^M) and high (20-50 ^M) doses, all exhibit multiple mechanisms of neuroprotection against oxidative damage in PC12 cells, including the inhibition of ROS formation and caspase-3 activity, decreases in membrane and DNA damage, enhancement of antioxidant enzyme activity, and the maintenance of calcium homeostasis and mitochondrial potential. Naringenin has shown antimutagenic effect. Nobiletin and neohesperetin inhibit amylase-catalyzed starch digestion, while nobiletin inhibits both amylose and amylopectin digestion, which suggest an hypoglycemic effect.

*Olea europaea* Leaves and Fruits Extract

Bioactive compounds: Gallic acid, hydroxytyrosol, chorogenic acid, protocatechuic acid hydroxyphenylacetic acid, 4-Hydroxybenzoic acid, catechin, oleuropeine, p-coumaric acid, ferulic acid, rosmarinic acid, vanillic acid, m-coumaric acid, phenylacetic acid, cinnamic acid, luteolin, apigenin and 3-Hydroxybenzoic acid.

Biological activity: The olive oil polyphenols (standardised by the content of hydroxytyrosol and its derivatives) protect LDL particles from oxidative damage which contributing with cardiovascular health. The active components have a potent antioxidant activity.

*Garnicia mangostana* Extract

Bioactive compounds: a mangostin 0.20% (w/w), x-mangostin 0.11% (w/w). P-mangostin, 9-hydroxycalabaxanthone, mangostanol, mangostenone, allanxanthone E, mangostingone, garcinone D, mangosenone G, cudraxanthon, 1,5,8-trihydroxy-3-methoxy-2-(3-methylbut-2-enyl) xanthone, 8-deoxygartanin, gartanin, and smeathxanthone A.

Biological activity: *Garcinia mangostana* improves the antioxidant activity of plasma in humans and has antiinflamatory activity.

*Garcinia* Species Extract: *G. cambogia, G. kola, G. madruno*

Bioactive compounds: biflavonoids, flavonoids, benzophenones, xanthones, and organic acids, hydroxycitric acid.

Biological activity: *Garcinia* species are used for the prevention and treatment of multiple symptoms and diseases such as ulcers, diarrhoea, hypertension, obesity, inflammatory disorders, hepatic damage, among others.

Thermal Characterization of Cacao Extract

Cacao extracts were analyzed by a variety of thermal characterization techniques.

Figure 3:
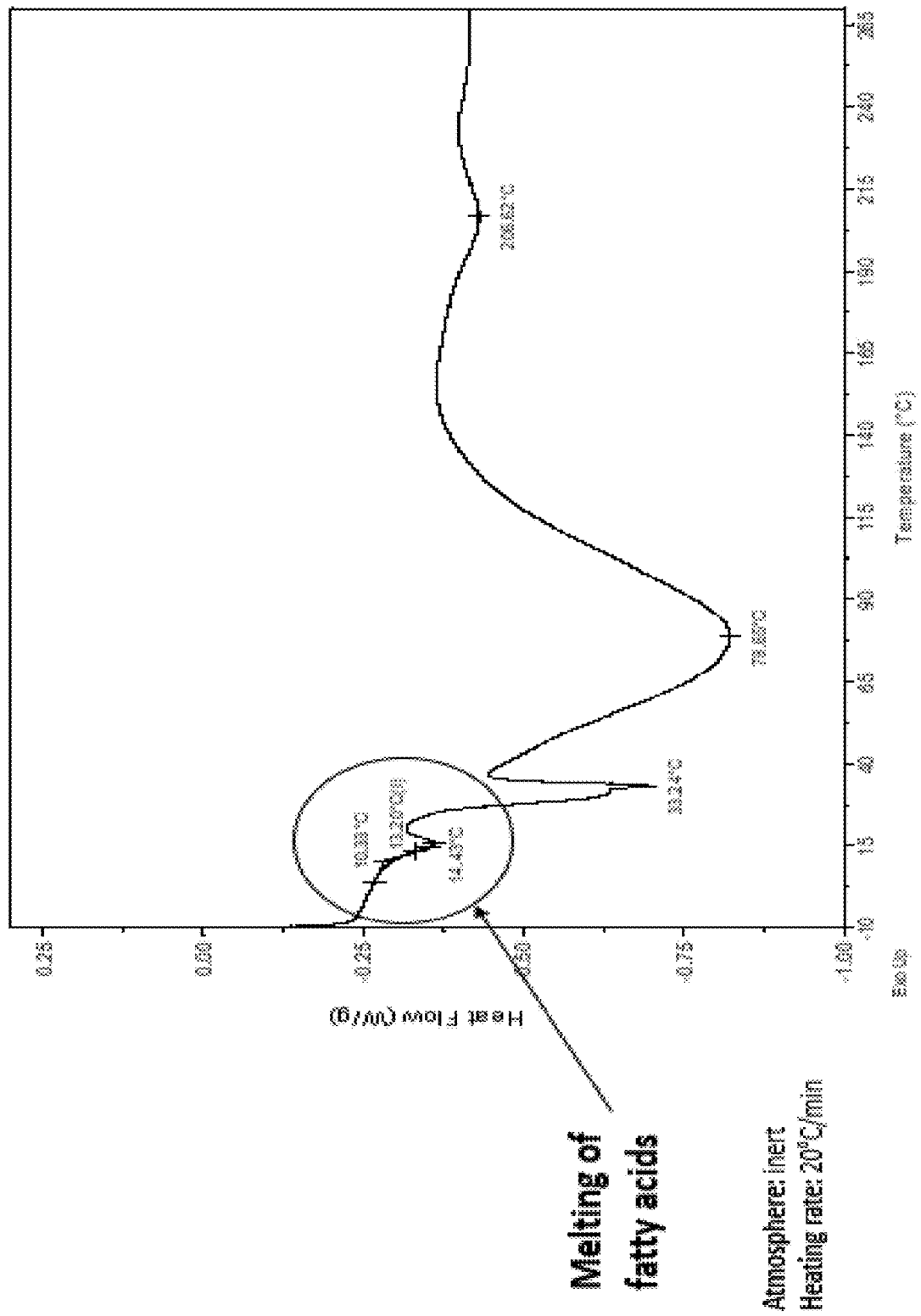
FIG. 3 describes the first heat Cacao Extract Differential Scanning calorimetry (DSC) characterization.

Cacao Extract Differential Scanning calorimetry (DSC) characterization: First heat thermal analysis is shown in FIG. 3.

The melting points of different fatty acids are shown in Table 8.

TABLE 8

| Unsaturated Fatty Acids | | |
| --- | --- | --- |
| Formula | Common Name | Melting Point |
| CH3(CH2)5CH=CH(CH2)7CO2H | Palmitoleic Acid | 0° C. |
| CH3(CH2)7CH=CH(CH2)7CO2H | Oleic acid | 13° C. |
| CH3(CH2)4CH=CHCH2CH=CH(CH2)7CO2H | Linoleic Acid | −5° C. |
| CH3CH2CH=CHCH2CH=CHCH2CH=CH(CH2)7CO2H | Linoleic acid | −11° C. |
| CH3(CH2)4(CH=CHCH2)4(CH2)2CO2H | Arachidonic acid | −49° C. |

Figure 4:
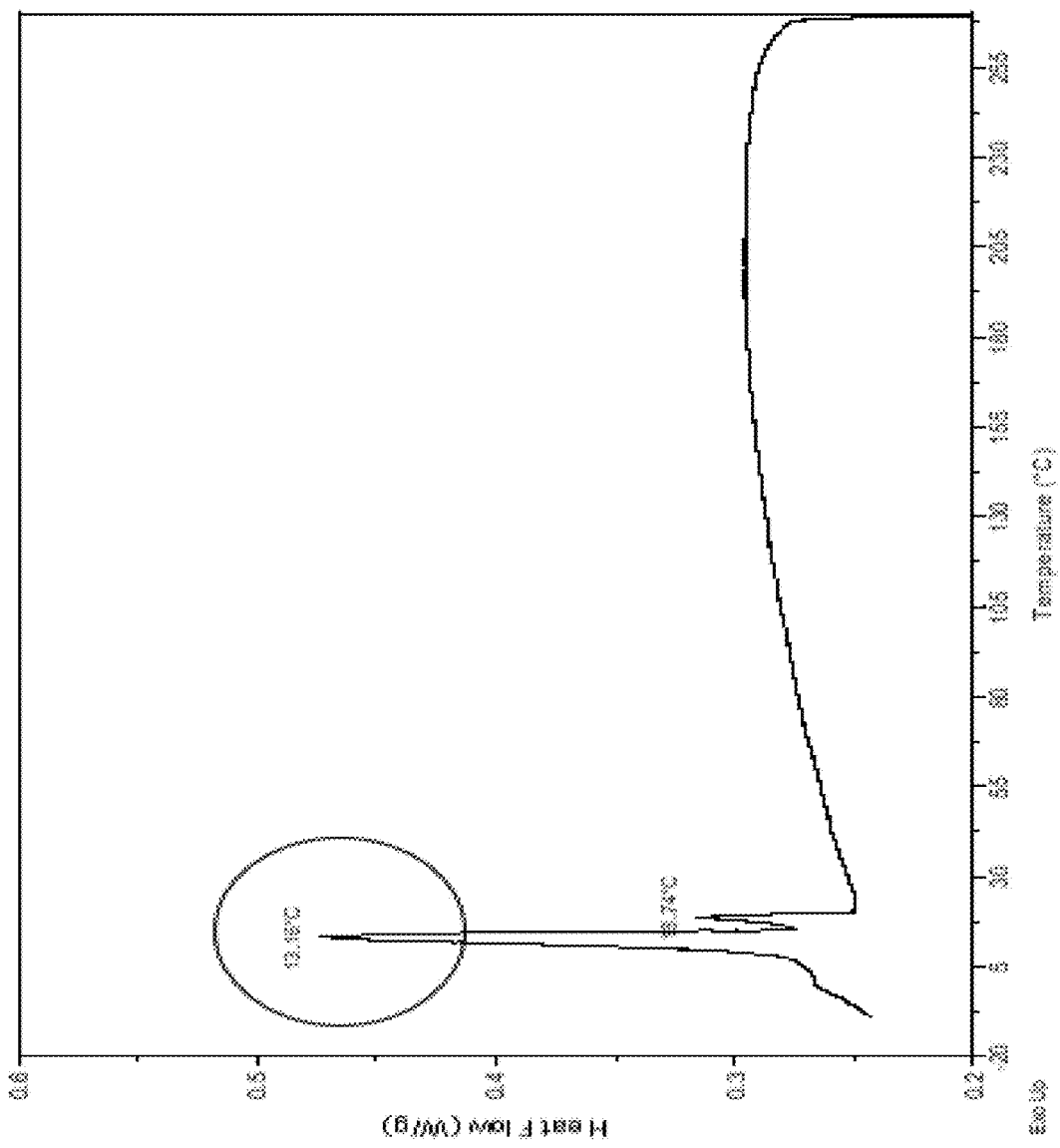
FIG. 4 shows the Cacao extract Differential Scanning calorimetry (DSC) Cooling curve. characterization.
Figure 5:
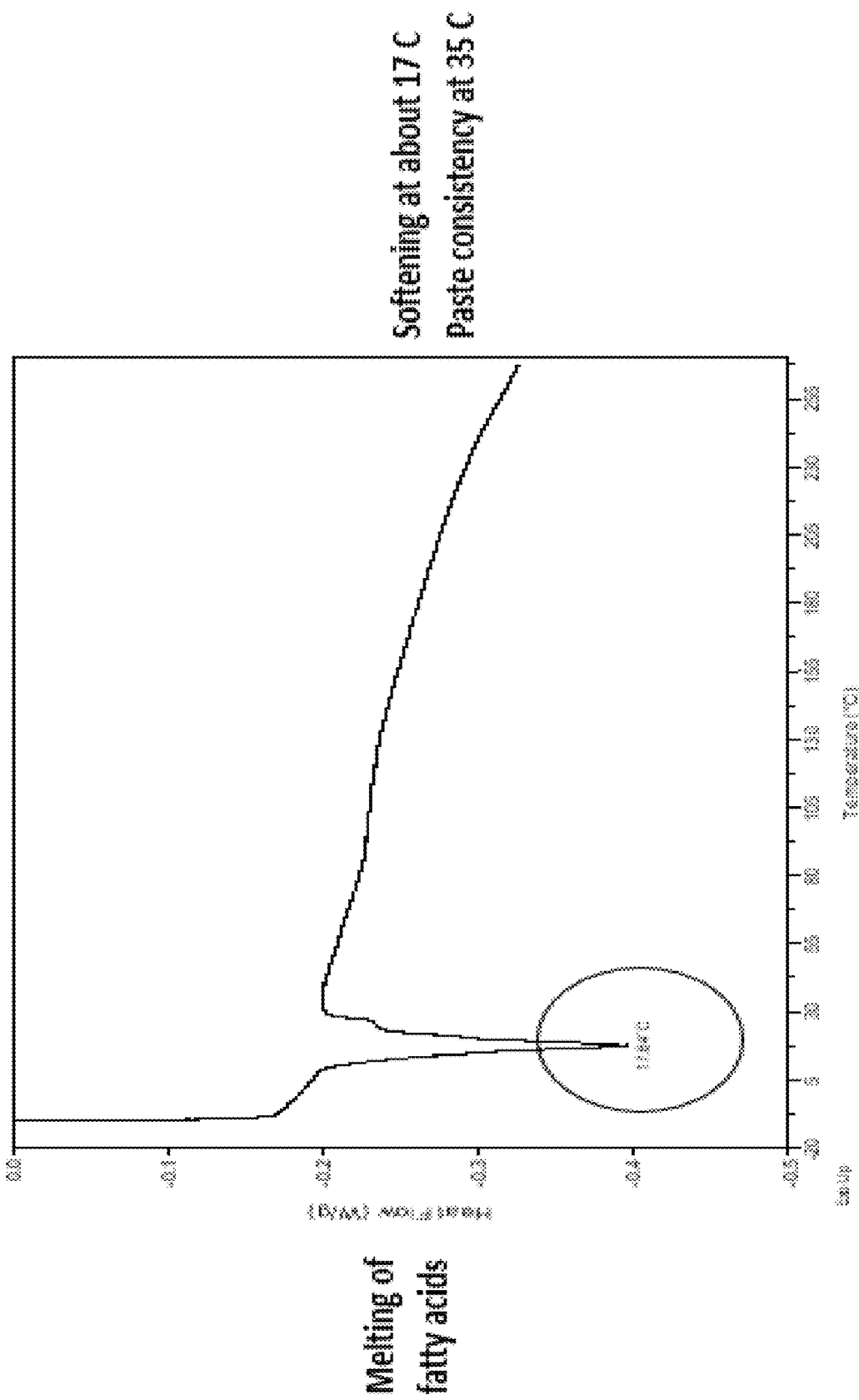
FIG. 5 illustrates the second heat thermal analysis Cacao extract Differential Scanning calorimetry (DSC) characterization.

FIG. 4 shows Cacao extract Differential Scanning calorimetry (DSC) characterization: Cooling curve, while FIG. 5 features a cacao extract Differential Scanning calorimetry (DSC) characterization second heat thermal analysis.

Figure 6:
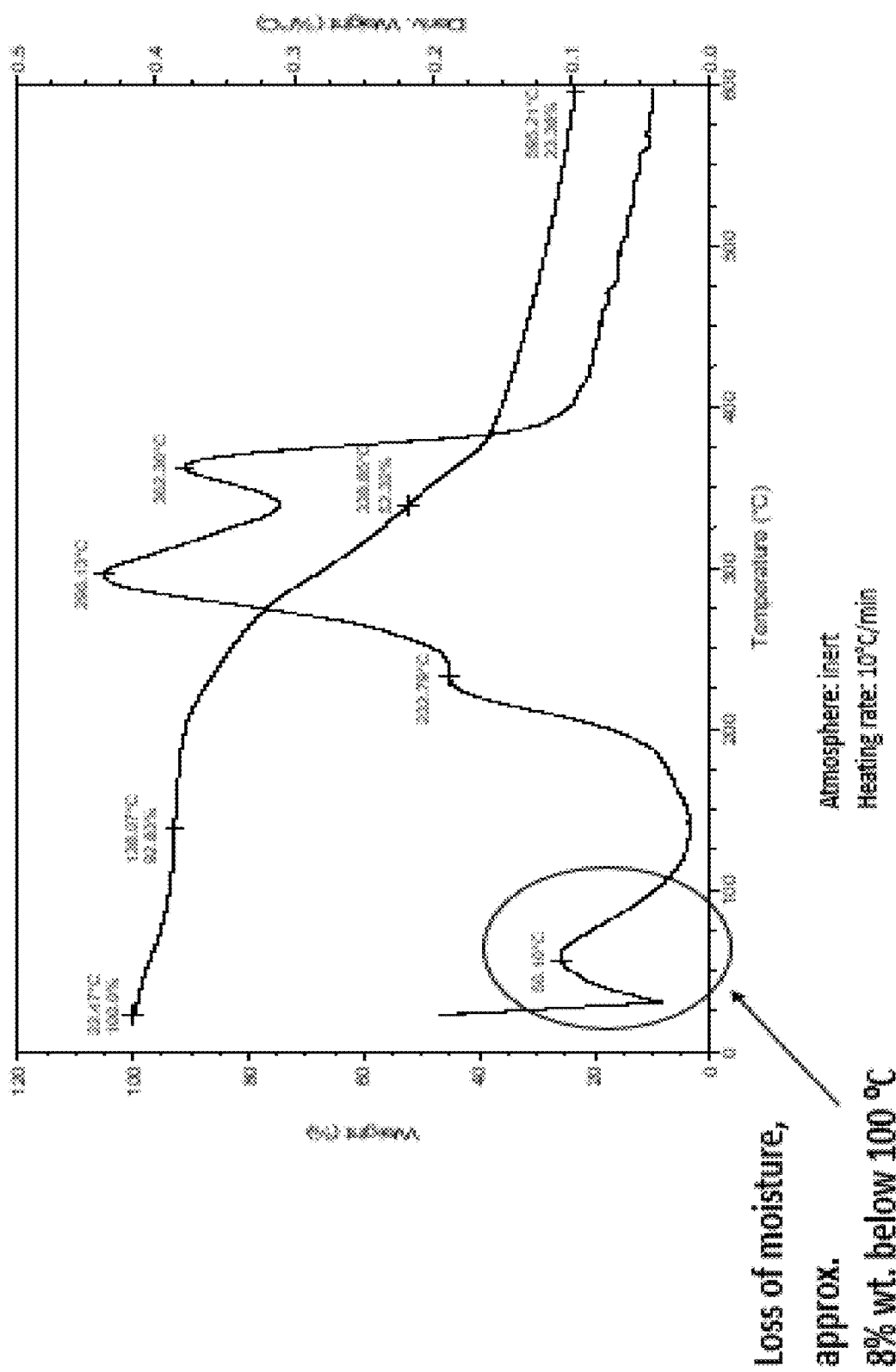
FIG. 6 describes the cacao extract Thermogravimetric analysis (TGA) characterization.
Figure 7:
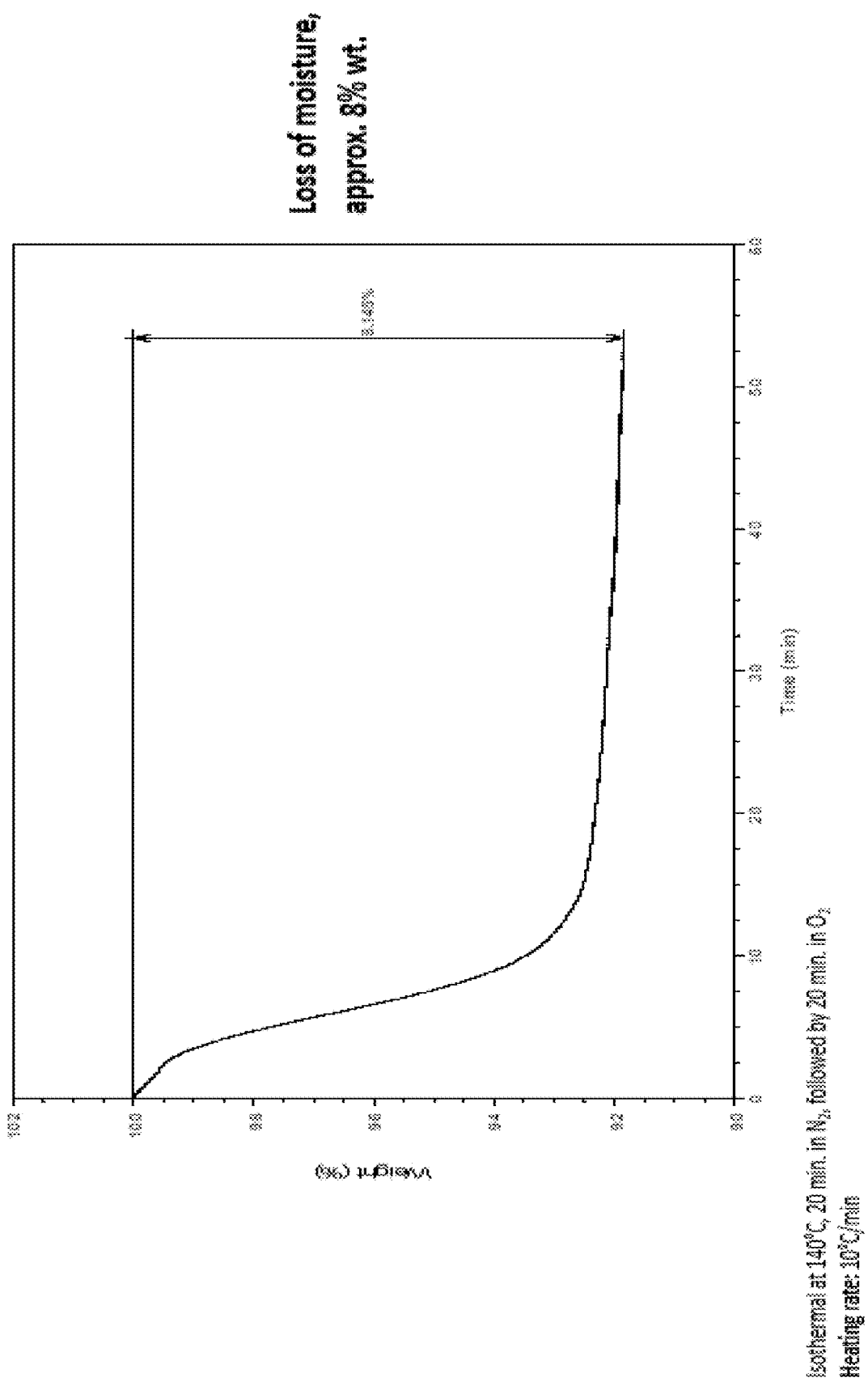
FIG. 7 features the cacao extract Isothermal Thermogravimetric characterization.

FIG. 6 describes the thermogravimetric analysis (TGA) characterization of a cacao extract while FIG. 7 is a cacao extract Isothermal Thermogravimetric characterization.

Figure 8:
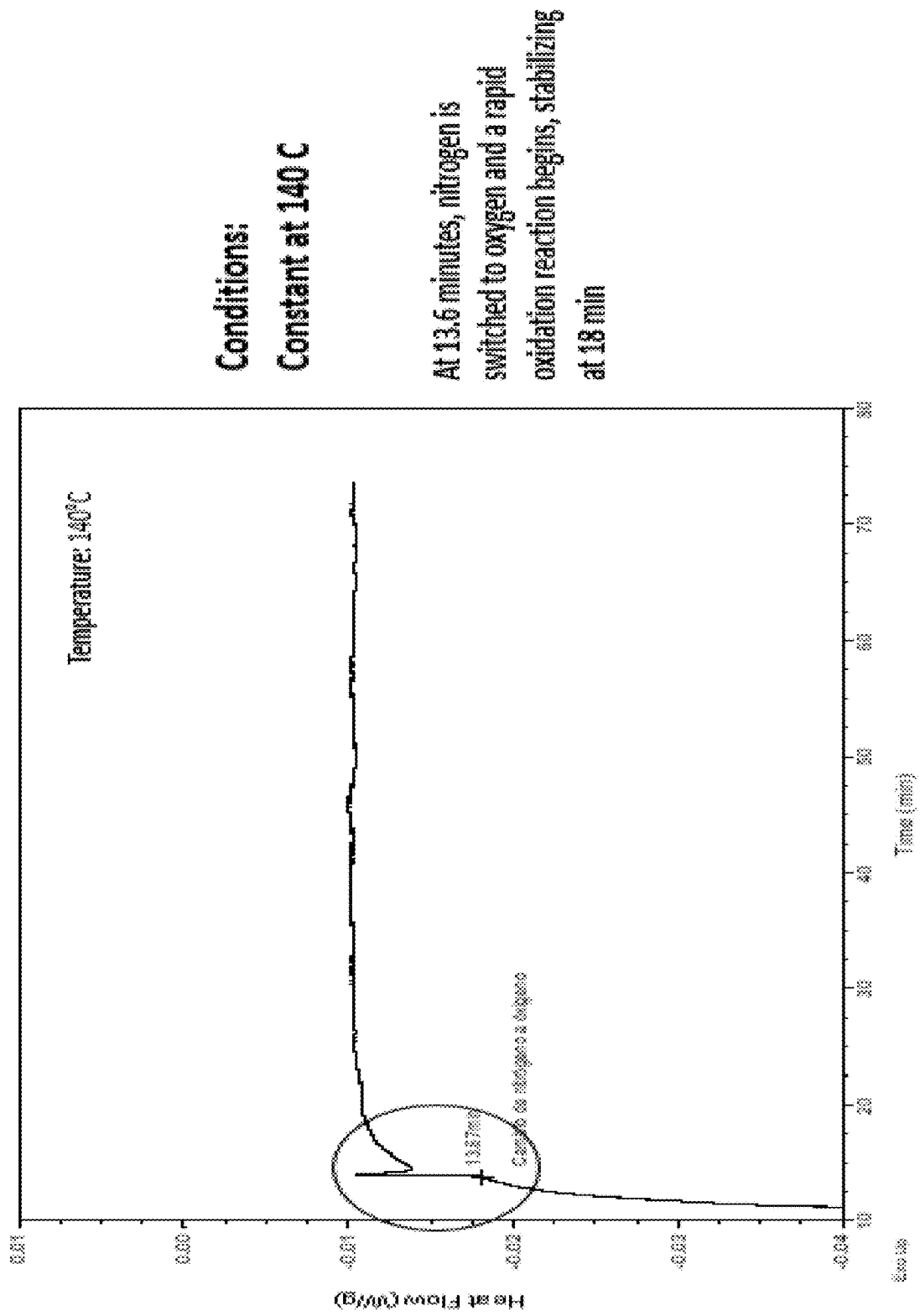
FIG. 8 illustrates the Cacao extract Oxygen Induction Time (OIT) characterization-Stability Analysis.
Figure 9:
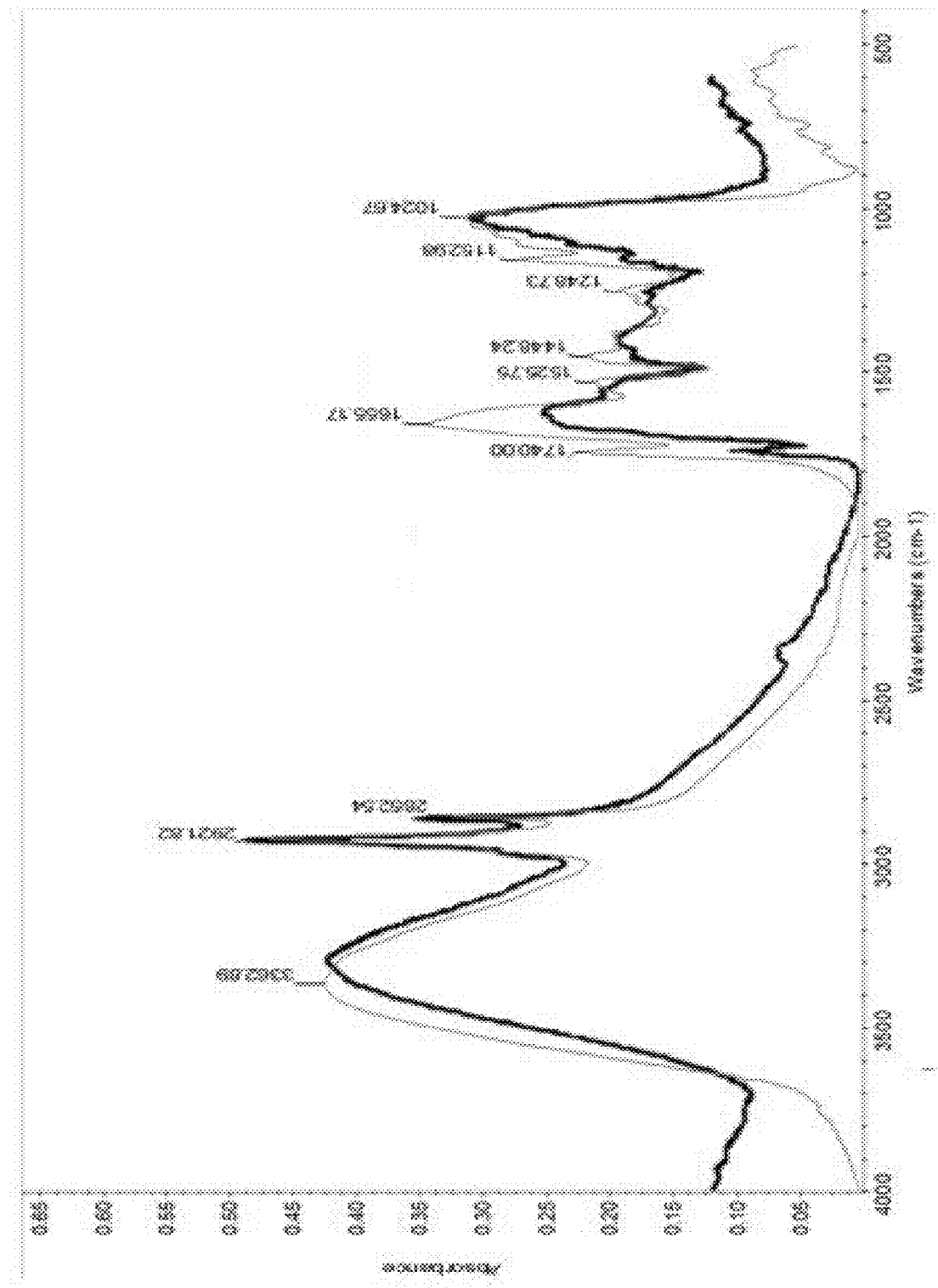
FIG. 9 describes the Cacao extract Fourier-Transform Infrared Spectrocopy (FTIR) characterization.

FIG. 8 illustrates the cacao extract Oxygen Induction Time (OIT) characterization-Stability Analysis and FIG. 9 shows a cacao extract Fourier-Transform Infrared Spectrocopy (FTIR) characterization.

The FTIR spectrum was compared to other spectra of cacao extracts in the literature, showing similar absorption bands. [Vesela A, eta al. Infrared spectroscopy and outer product analysis for quantification of fat, nitrogen, and moisture of cacao powder. Analytical Chimica Acta 2007; 601: 77-86]

The absorption bands in the cacao extract (FTIR) are shown in Table 9.

TABLE 9

| Wave number (cm$^{-1}$) | Assignment |
| --- | --- |
| 3362 | Stretching O—H of fatty acids, carbohydrates and others |
| 2921 | Stretching C—H of methylene and CH2 carbohydrates |
| 2852 | Stretching C—H of fatty Acids |
| 1740 | Stretching C=O of fatty Acids |
| 1656 | Stretching C=O of amide I protein |
| 1525 | Stretching C—N of amide II protein |
| 1448 | Flexing C—H |
| 138 | Flexing O—H of fatty acids, carbohydrates and others |
| 1248 | Flexing N—H of amide III protein |
| 1152 | Stretching C—O of fatty acids |

TABLE 9-continued

| Wave number (cm$^{-1}$) | Assignment |
|---|---|
| 1024 | Stretching C—O of carbohydrates |
| <900 | Flexing C—H out of scope |

Thermal Characterization of (−)-Epicatechin

Figure 10:
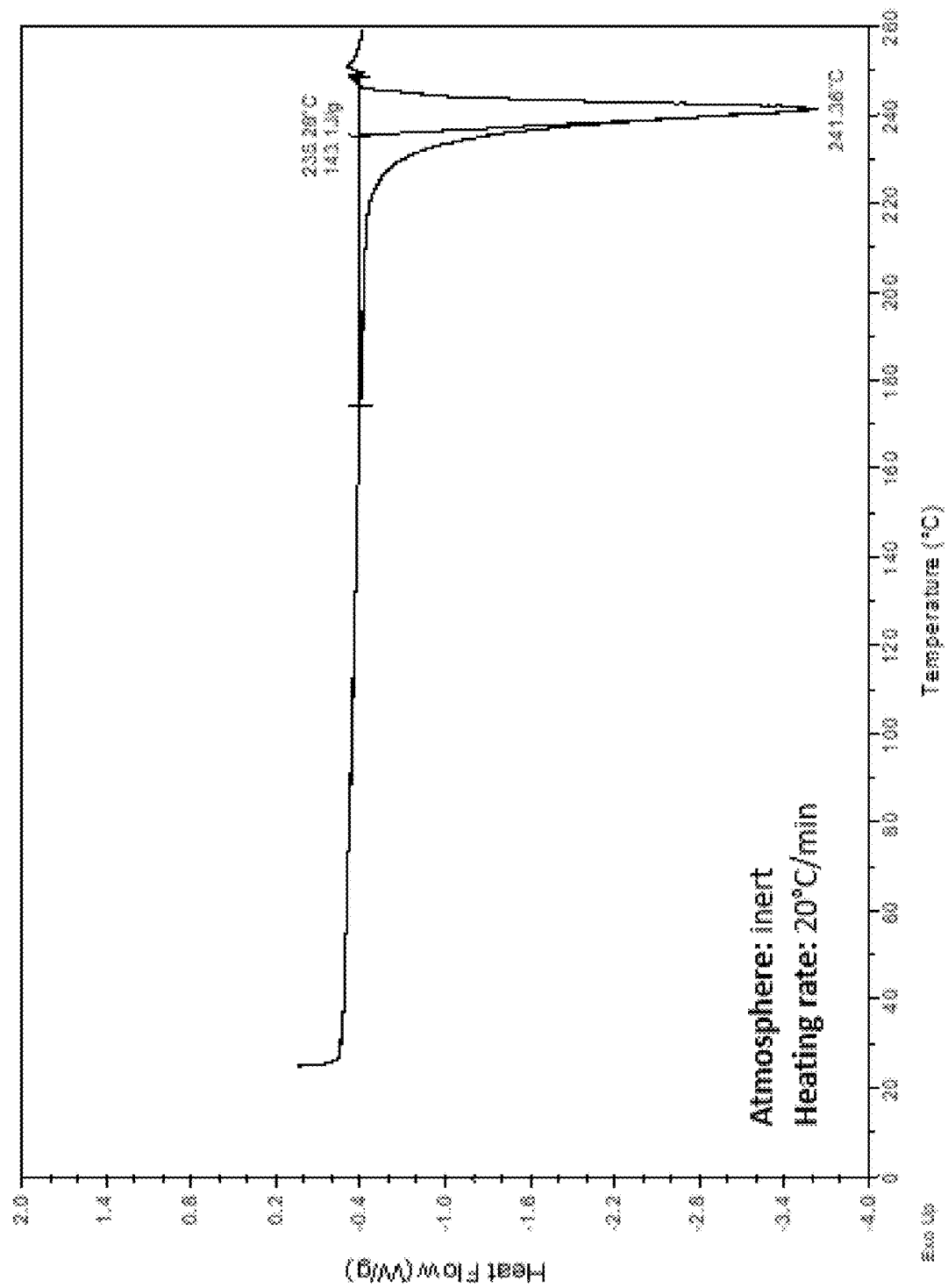
FIG. 10 shows the first heating thermal analysis of (−)-Epicatechin at 90% Differential Scanning calorimetry (DSC) characterization.

FIG. 10 illustrates the (−)-Epicatechin at 90% Differential Scanning calorimetry (DSC) characterization for the first heating thermal analysis.

Thermal Characterization of Cocoa Extract

Figure 11:
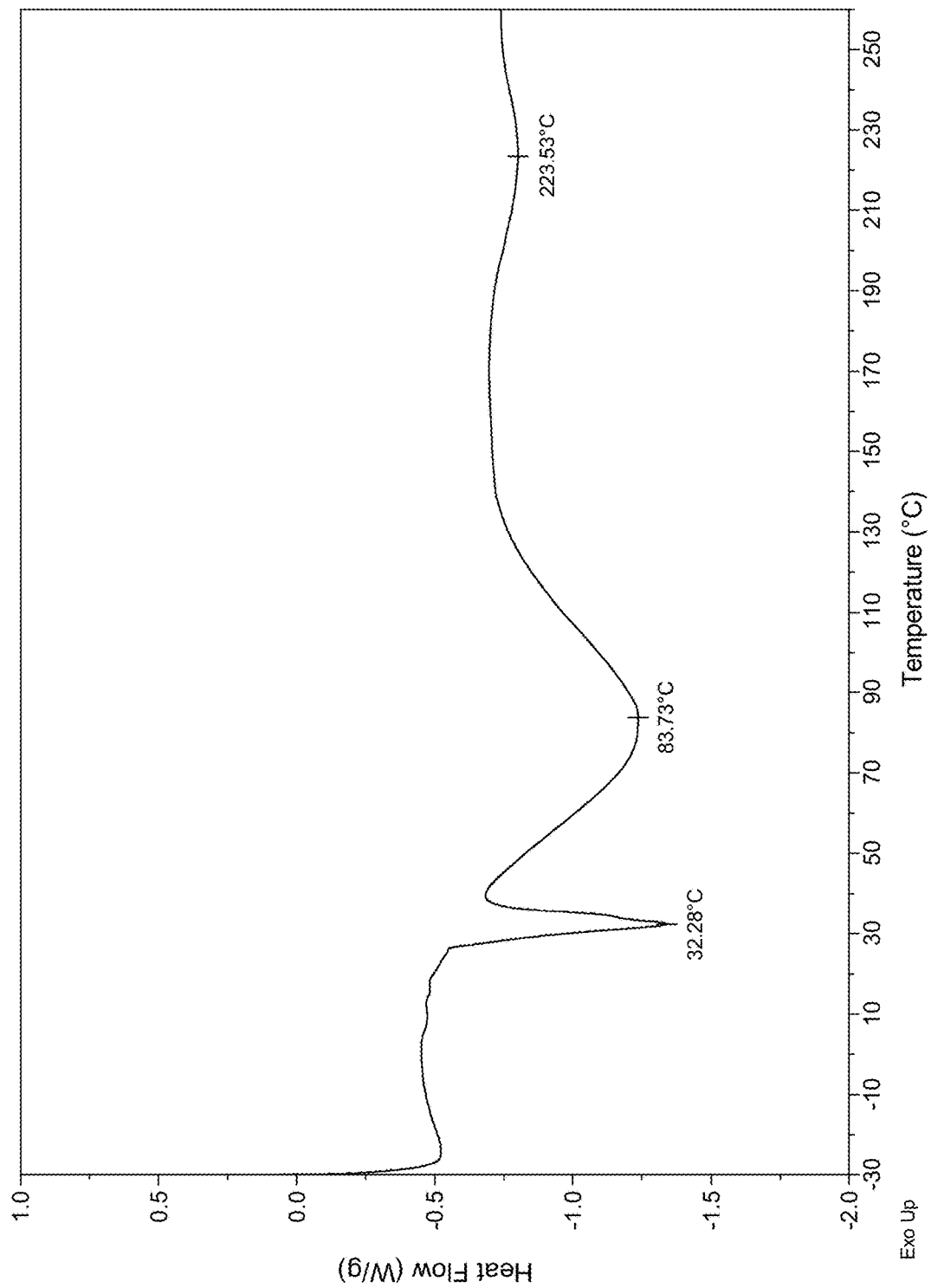
FIG. 11 features another first heating thermal analysis Cocoa Extract Differential Scanning calorimetry (DSC) characterization.

FIG. 11 illustrates the cocoa xxtract Differential Scanning Calorimetry (DSC) characterization first heating thermal analysis.

EXAMPLES

The invention is exemplified as shown in the Examples below.

Example I

50EXT-40SOLU-10L100-T120-120RPM-RT
50% Cacao Extract
40% Soluplus (BASF polymer)
10% Eudragit L100 (Evonik polymer)
Process Conditions: batch melt mixing at 120 RPM and processing temperature of 120° C.

Example II

50EXT-30AN7-10SR-10L100-T150-120RPM-RT
50% Cacao Extract
30% Aqualon N7 (Ashland polymer)
10% Kollidon SR (Basf polymer)
10% Eudragit L100 (Evonik polymer)
Process Conditions: batch melt mixing at 120 RPM and processing temperature of 150° C.

Example III

50EXT-30AN7-10SR-10L100-120RPM-TSE
50% Cacao Extract
30% Aqualon N7 (Ashland polymer)
10% Kollidon SR (Basf polymer)
10% Eudragit L100 (Evonik polymer)
Process Conditions: twin screw extrusion (Nano 16 Leistritz) at 120 RPM (co-rotating screws) and temperature profile: 80° C. (feed zone), 150° C., 140° C. (metering zone), 140° C. (die)

Example IV

50EXT-30ES10-10SR-10L100-T150-120RPM-RT
50% Cacao Extract
30% Ethocel Standard 10 (Dow polymer)
10% Kollidon SR (Basf polymer)
10% Eudragit L100 (Evonik polymer)
Process Conditions: batch melt mixing at 120 RPM and 150° C.

Example V

Figure 12:
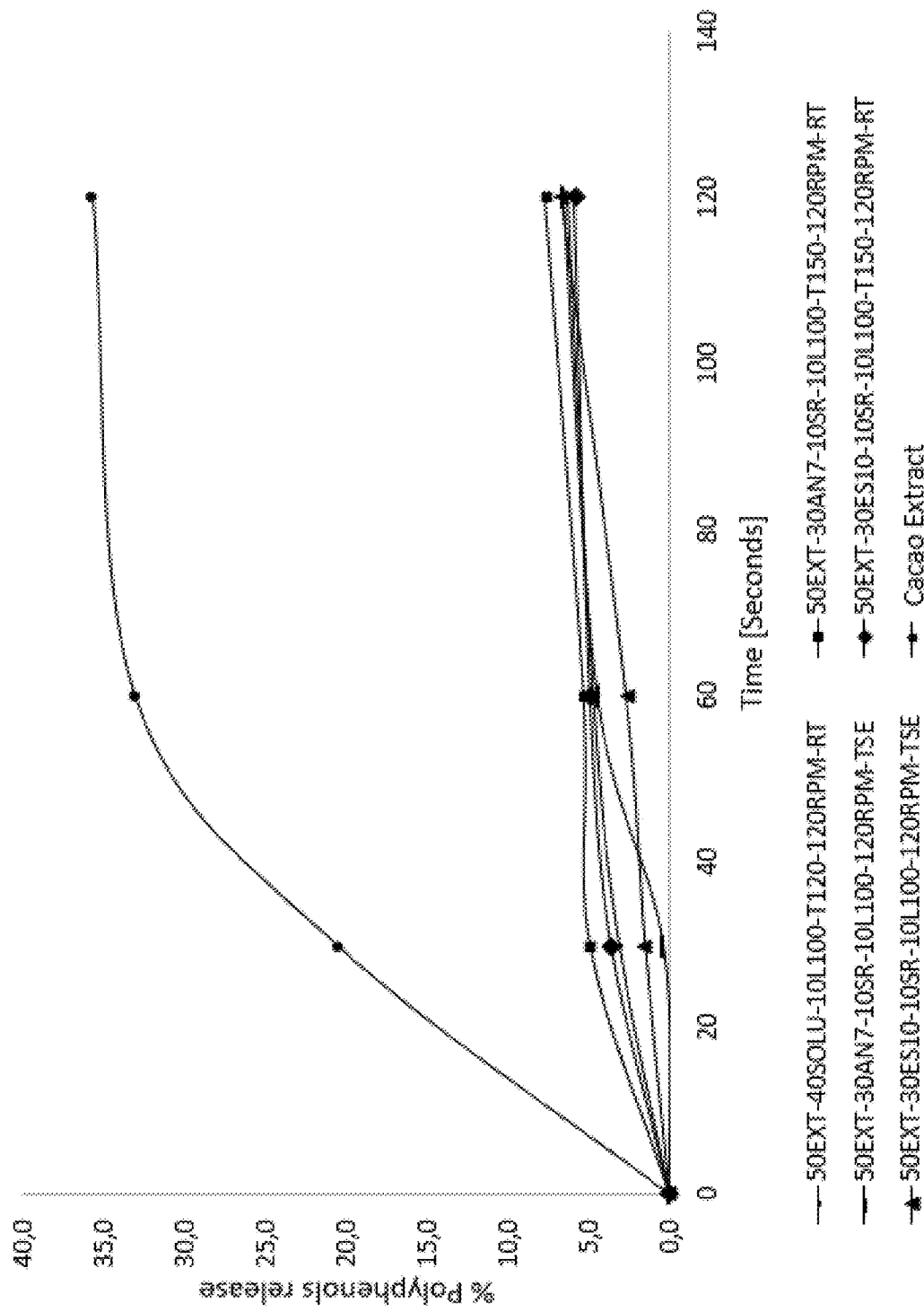
FIG. 12 illustrates the release profile of polyphenols in artificial saliva at 23° C. for examples I to V.

50EXT-30ES10-10SR-10L100-120RPM-TSE
50% Cacao Extract
30% Ethocel Standard 10 (Dow polymer)
10% Kollidon SR (Basf polymer)
10% Eudragit L100 (Evonik polymer)
Process Conditions: twin screw extrusion (Nano 16 Leistritz) at 120 RPM (co-rotating screws) and temperature profile: 80° C. (feed zone), 140° C., 140° C. (metering zone), 130° C. (die). FIG. 12 shows the Release profile of polyphenols in artificial saliva at 23° C. for EXAMPLES I TO V.

The FIG. 12 graph shows the encapsulated cacao extract (batch melt mixing, RT, and Twin Screw Extrusion, TSE), not tasted in food.

The Artificial Saliva at pH 6.2 is shown in Table 10.

TABLE 10

| Chemical | Amount (g/L) |
|---|---|
| CaCl2•2H2O | 0.228 |
| MgCl2•6H2O | 0.061 |
| NaCl | 1.071 |
| K2CO3 | 0.603 |
| Na2HPO4 | 0.204 |
| NaH2PO4 | 0.273 |

Figure 13:
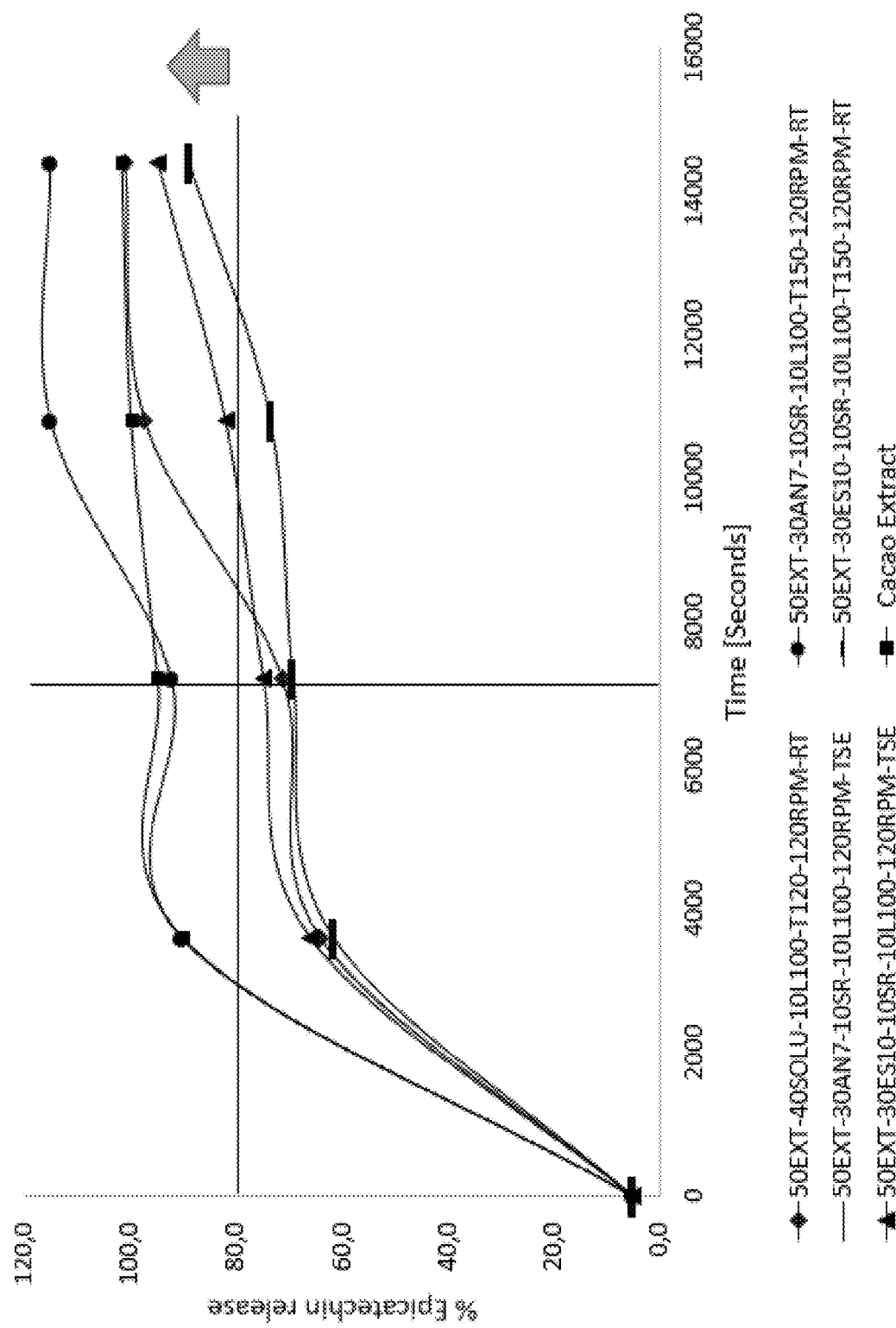
FIG. 13 describes the Release profile of (−)-Epicatechin at 2 hour in a medium with pH of 1.2 and 2 more hours in a medium with pH of 6.8, at 37° C. for examples I to V.

FIG. 13 shows the release profile of (−)-Epicatechin at 2 hour in a medium with pH of 1.2 and 2 more hours in a medium with pH of 6.8, at 37° C. Releases for EXAMPLES I TO V.

Figure 14:
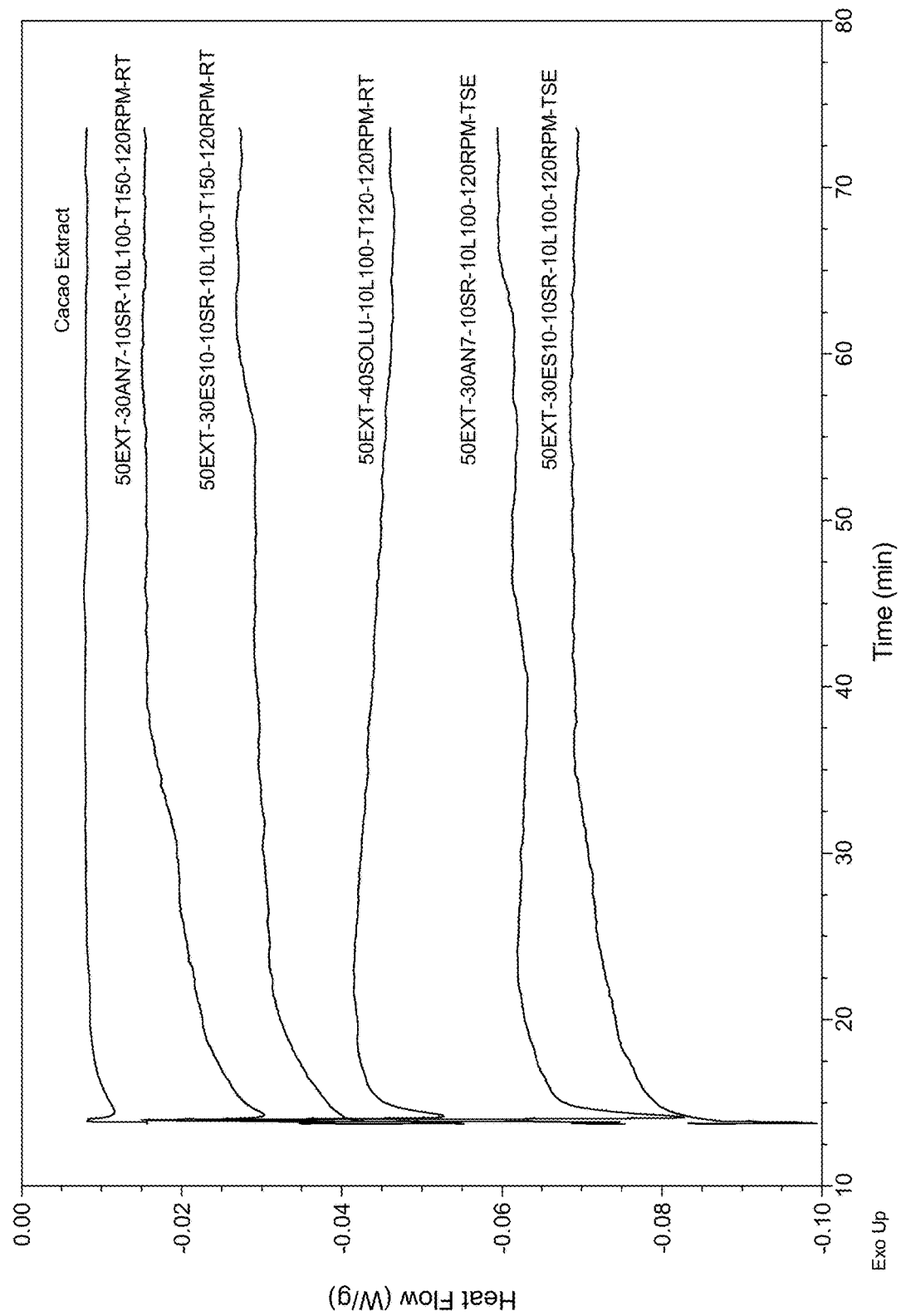
FIG. 14 shows the Oxygen Induction Time (OIT) for stability analysis of encapsulated formulations vs cacao extract for examples I to V.

FIG. 14 illustrates the Oxygen Induction Time (OIT) for stability analysis of encapsulated formulations vs cacao extract for EXAMPLES I TO V.

Example VI

50EXT-30AN7-10 SR-10L100-120RPM-TSE
50% Cacao Extract
30% Aqualon N7 (Ashland polymer)
10% Kollidon SR (Basf polymer)
10% Eudragit L100 (Evonik polymer)
Process Conditions: twin screw extrusion (Nano 16 Leistritz) at 120 RPM (co-rotating screws) and temperature profile: 80° C. (feed zone), 150° C., 140° C. (metering zone), 140° C. (die).

Figure 15:
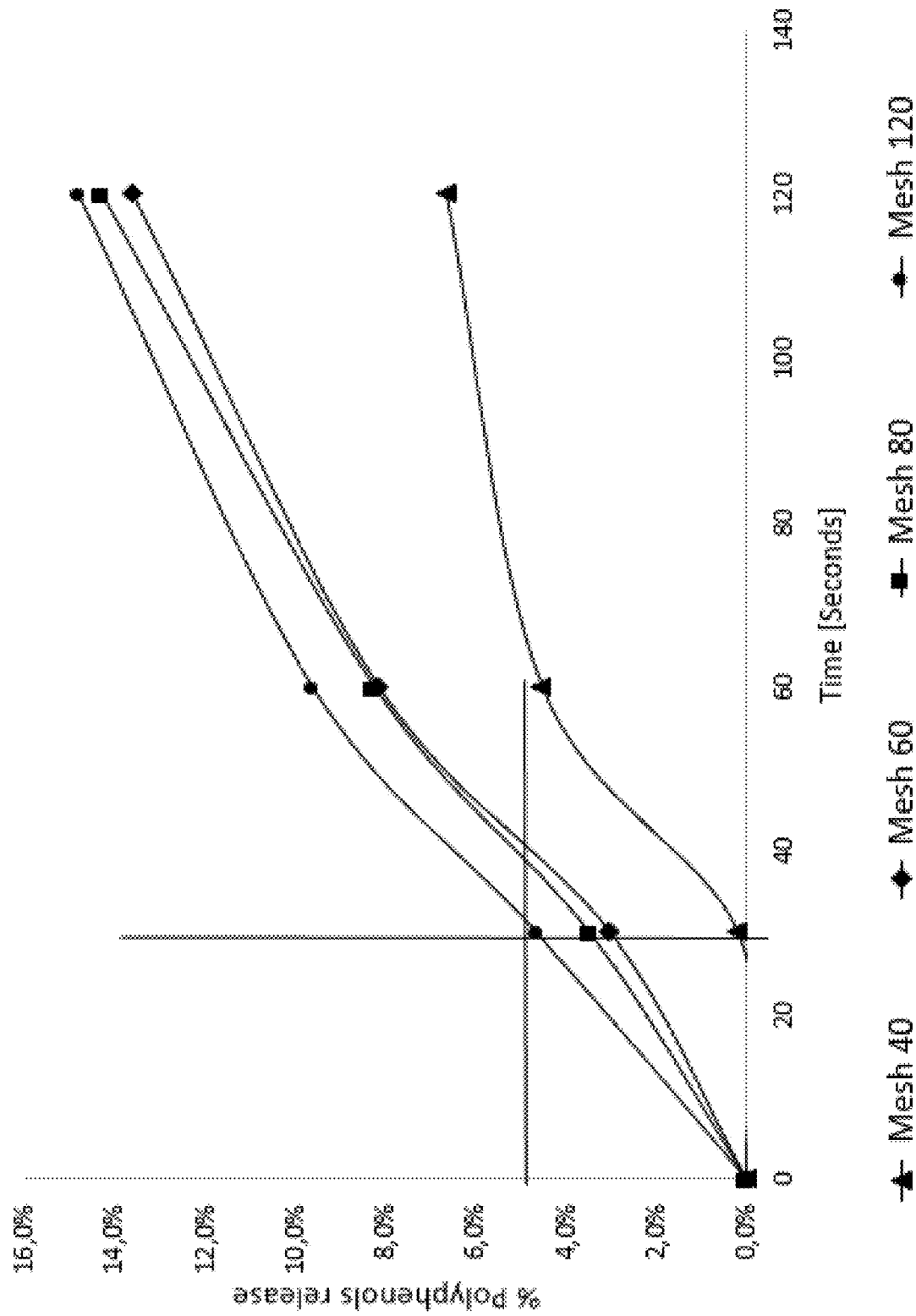
FIG. 15 shows the release profile of polyphenols in artificial saliva at 23° C. for example VI.

FIG. 15 shows the release profile of polyphenols in artificial saliva at 23° C. for EXAMPLE VI with particle size distribution between 250 μm and 425 μm (Mesh 40), 180 μm and 250 μm (Mesh 60), 125 μm and 180 μm (Mesh 80), and particle size smaller than 120 μm (Mesh 120):

Example VII

50EXT-30ES10-10SR-10L100-120RPM-TSE
50% Cacao Extract
30% Ethocel Standard 10 (Dow polymer)
10% Kollidon SR (Basf polymer)
10% Eudragit L100 (Evonik polymer)
Process Conditions: twin screw extrusion (Nano 16 Leistritz) at 120 RPM (co-rotating screws) and temperature profile: 80° C. (feed zone), 140° C., 140° C. (metering zone), 130° C. (die).

Figure 16:
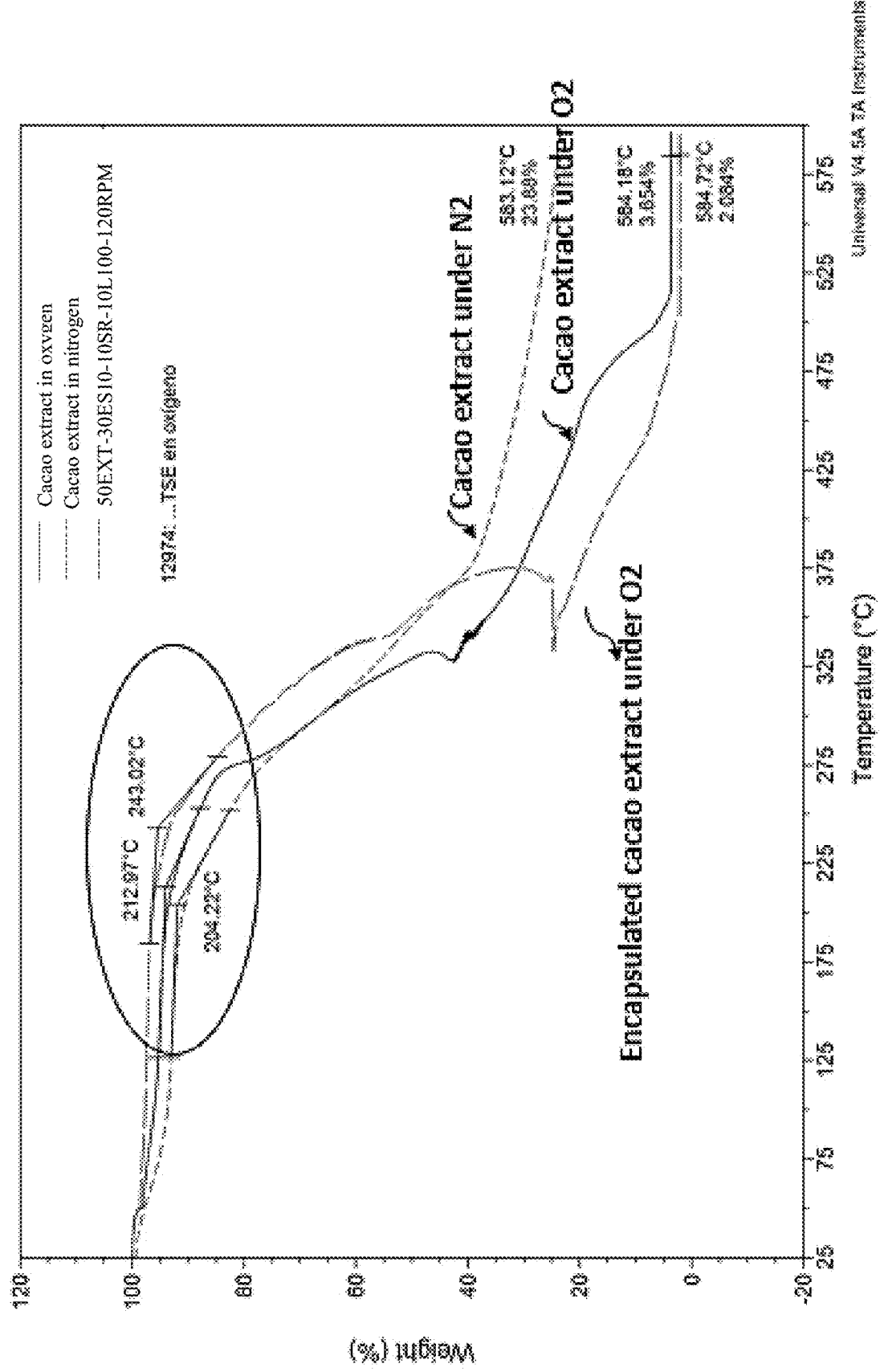
FIG. 16 describes the Thermogravimetric analysis of cacao extract vs an encapsulated formulation from example VII.

FIG. 16 describes the Thermogravimetric analysis of cacao extract vs an encapsulated formulation from example VII. Encapsulation provides thermal stability and moisture resistance to the cacao extract.

Example VIII

50EXT-50ES10-T180-120 RPM-RT
50% Cacao Extract
50% Ethocel Standard 10 (Dow polymer)
Process Conditions: batch melt mixing at 120 RPM and processing temperature of 180° C.

Example IX

50EXT-50AN7-T140-70RPM-RT
50% Cacao Extract
50% Aqualon N7 (Ashland polymer)
Process Conditions: batch melt mixing at 70 RPM and processing temperature of 140° C.

Figure 17:
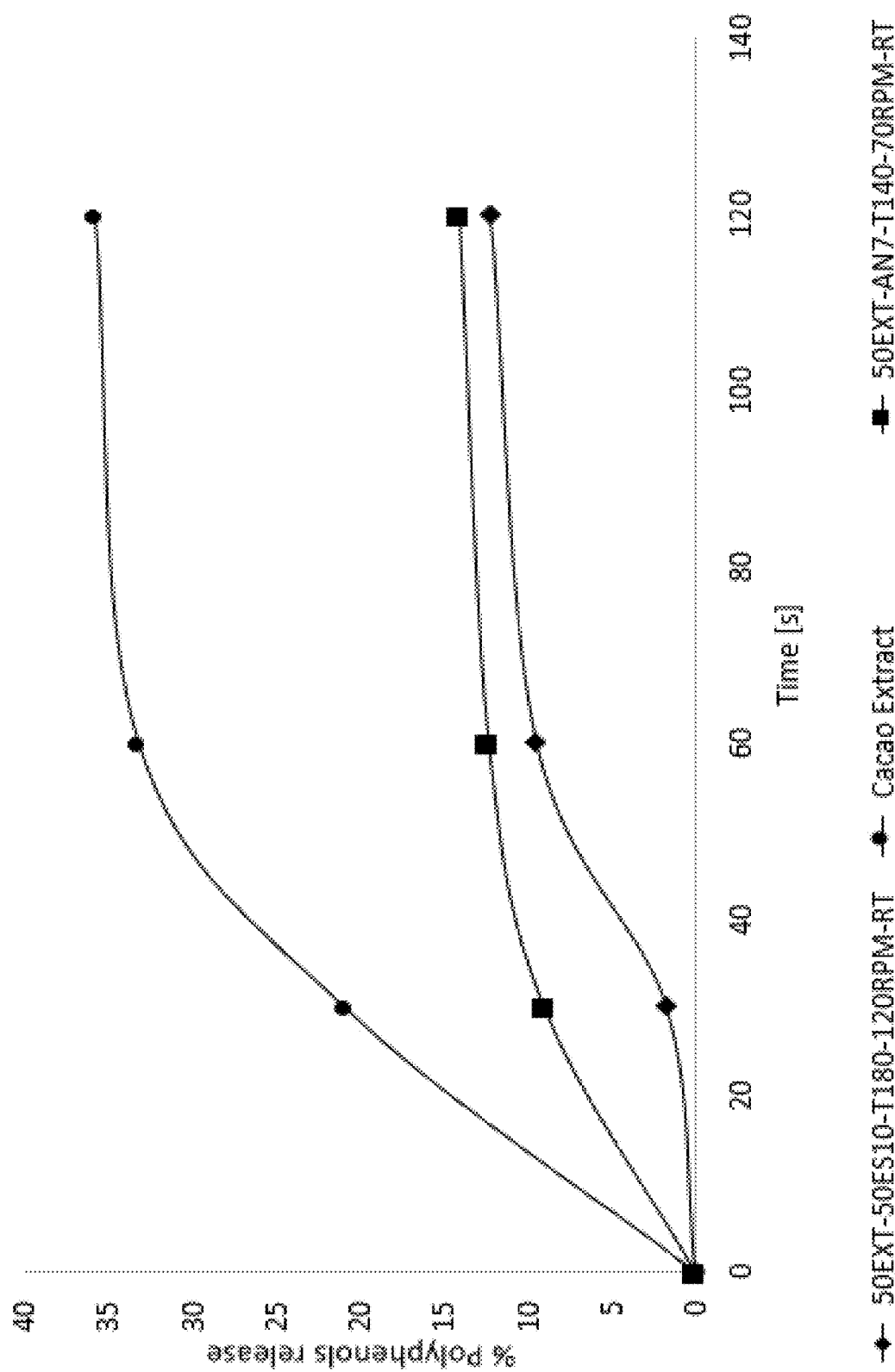
FIG. 17 illustrates Release profile of polyphenols in artificial saliva at 23° C. for examples VIII and IX.

FIG. 17 illustrates Release profile of polyphenols in artificial saliva at 23° C. for EXAMPLE VIII and IX.

Figure 18:
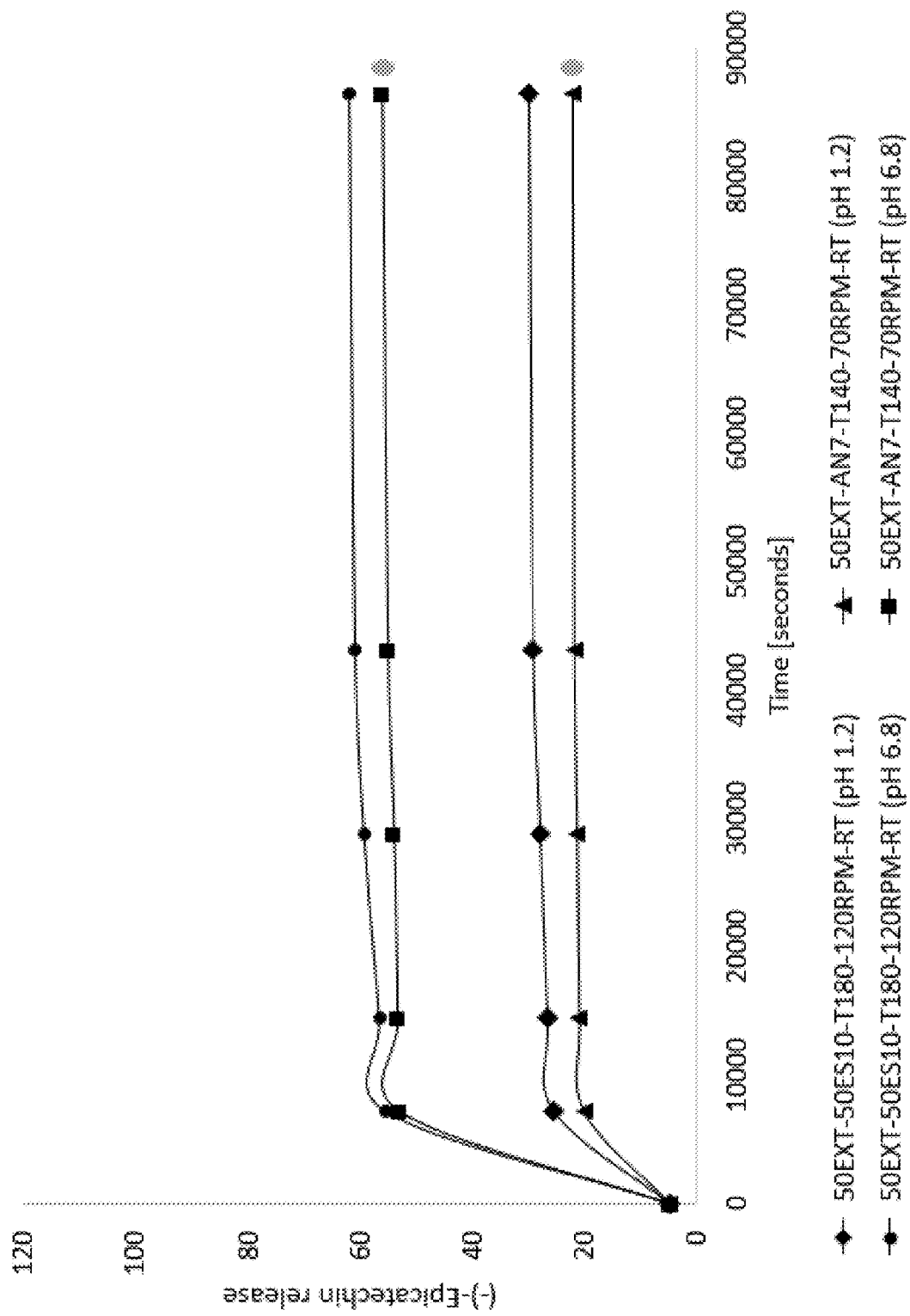
FIG. 18 shows the release profile of (−)-Epicatechin at 2 hour in a medium with pH of 1.2 and 2 more hours in a medium with pH of 6.8, at 37° C. for examples VIII and IX.

FIG. 18 shows the release profile of (−)-Epicatechin at 2 hour in a medium with pH of 1.2 and 2 more hours in a medium with pH of 6.8, at 37° C. for examples VIII and IX.

Example X

50EPI-30AN7-10L100-10 SR-T130-70RPM-RT
50% (−)-Epicatechin (90%)
30% Aqualon N7 (Ashland polymer)
10% Eudragit L100 (Evonik polymer)
10% Kollidon SR (Basf polymer)
Process Conditions: batch melt mixing at 70 RPM and processing temperature of 130° C.

Example XI

50EPI-30AN7-10L100-10SR-T130-100RPM-RT
50% (−)-Epicatechin (90%)
30% Aqualon N7 (Ashland polymer)
10% Eudragit L100 (Evonik polymer)
10% Kollidon SR (Basf polymer)
Process Conditions: batch melt mixing at 100 RPM and processing temperature of 130° C.

Example XII

50EPI-30AN7-10L100-10 SR-T150-70RPM-RT
50% (−)-Epicatechin (90%)
30% Aqualon N7 (Ashland polymer)
10% Eudragit L100 (Evonik polymer)
10% Kollidon SR (Basf polymer)
Process Conditions: batch melt mixing at 70 RPM and processing temperature 150° C.

Example XIII

50EPI-30AN7-10L100-10SR-T150-100RPM-RT
50% (−)-Epicatechin (90%)
30% Aqualon N7 (Ashland polymer)
10% Eudragit L100 (Evonik polymer)
10% Kollidon SR (Basf polymer)
Process Conditions: batch melt mixing at 100 RPM and processing temperature 150° C.

Figure 19:
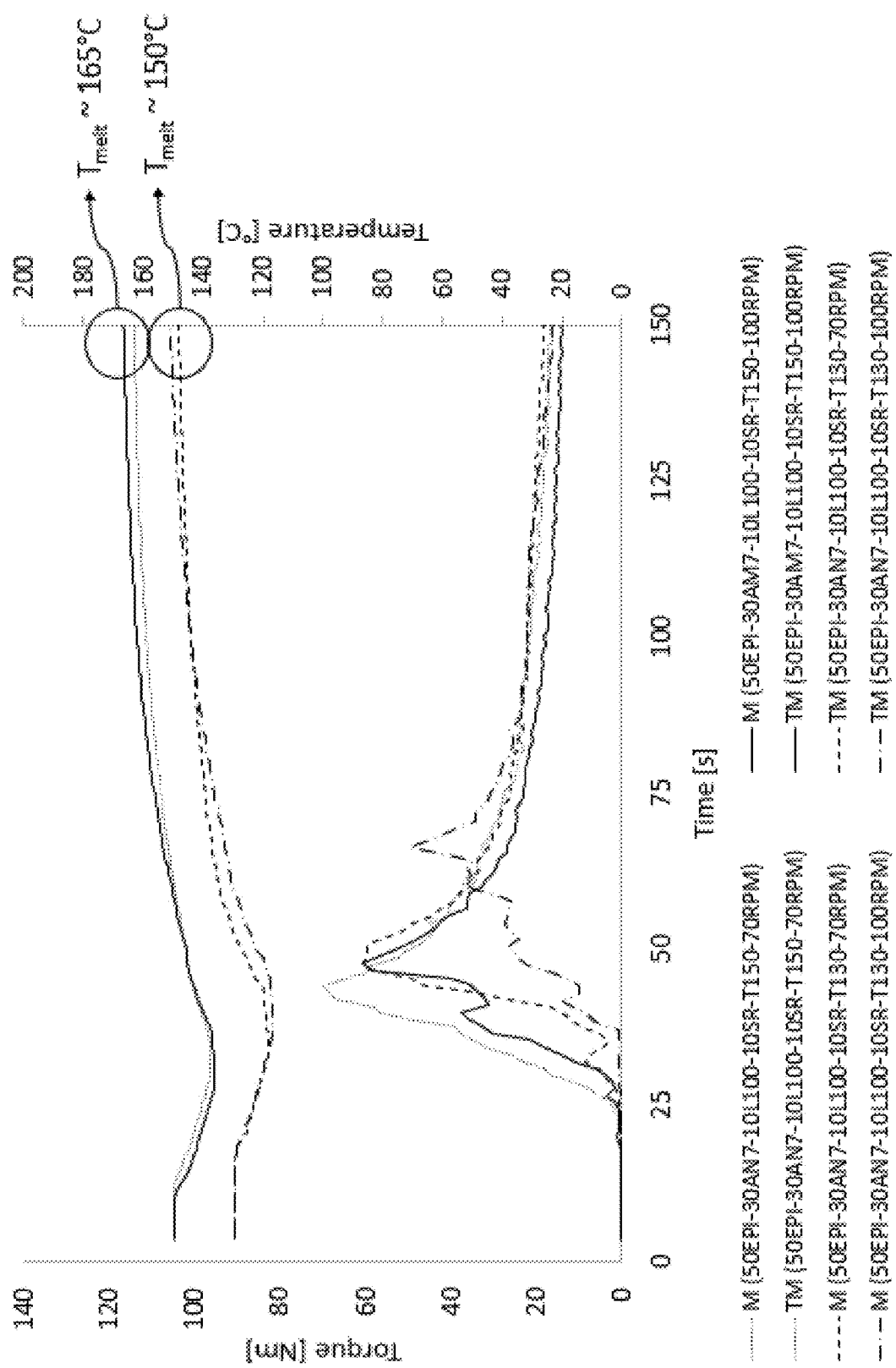
FIG. 19 describes the torque and melt temperature behavior of examples X to XIII FIG. 20 describes the release profile of (−)-Epicatechin in artificial saliva at pH 6.2 and 23° C. for examples X to XIII
Figure 20:
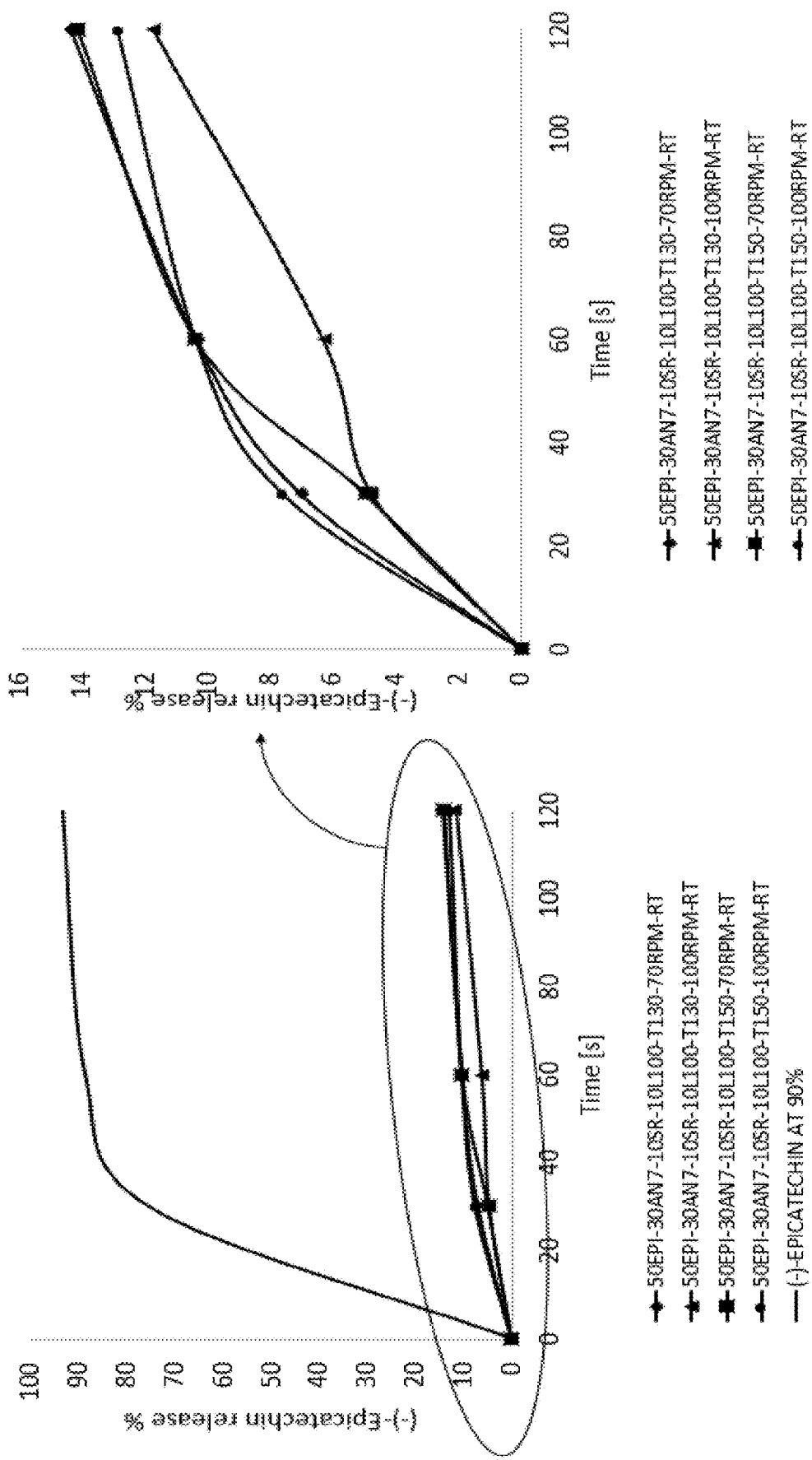

FIG. 19 describes the torque and melt temperature behavior of examples X to XIII FIG. 20 describes the release profile of (−)-Epicatechin in artificial saliva at pH 6.2 and 23° C. for examples X to XIII with a particle size distribution between 250 μm and 425 μm (Mesh 40).

Figure 21:
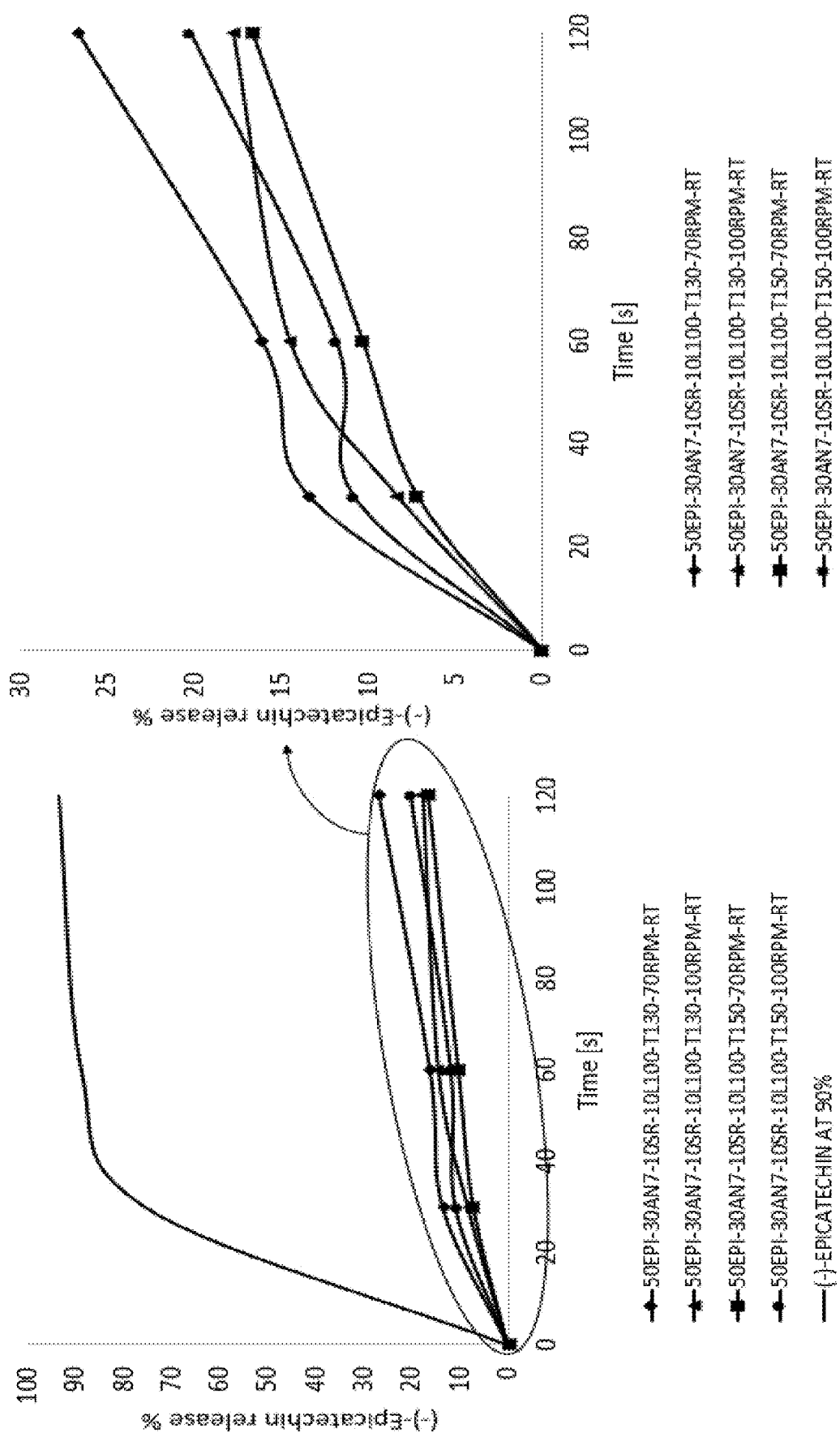
FIG. 21 illustrates the release profile of (−)-Epicatechin in artificial saliva at pH 6.2 and 23° C. for examples X to XIII FIG. 22 features release profile of (−)-Epicatechin at 2 hour in a medium with pH of 1.2 and 2 more hours in a medium with pH of 6.8, at 37° C. examples X to XIII

FIG. 21 illustrates the release profile of (−)-Epicatechin in artificial saliva at pH 6.2 and 23° C. for EXAMPLE X to XIII with a particle size distribution between 180 μm and 250 μm (Mesh 60).

Figure 22:
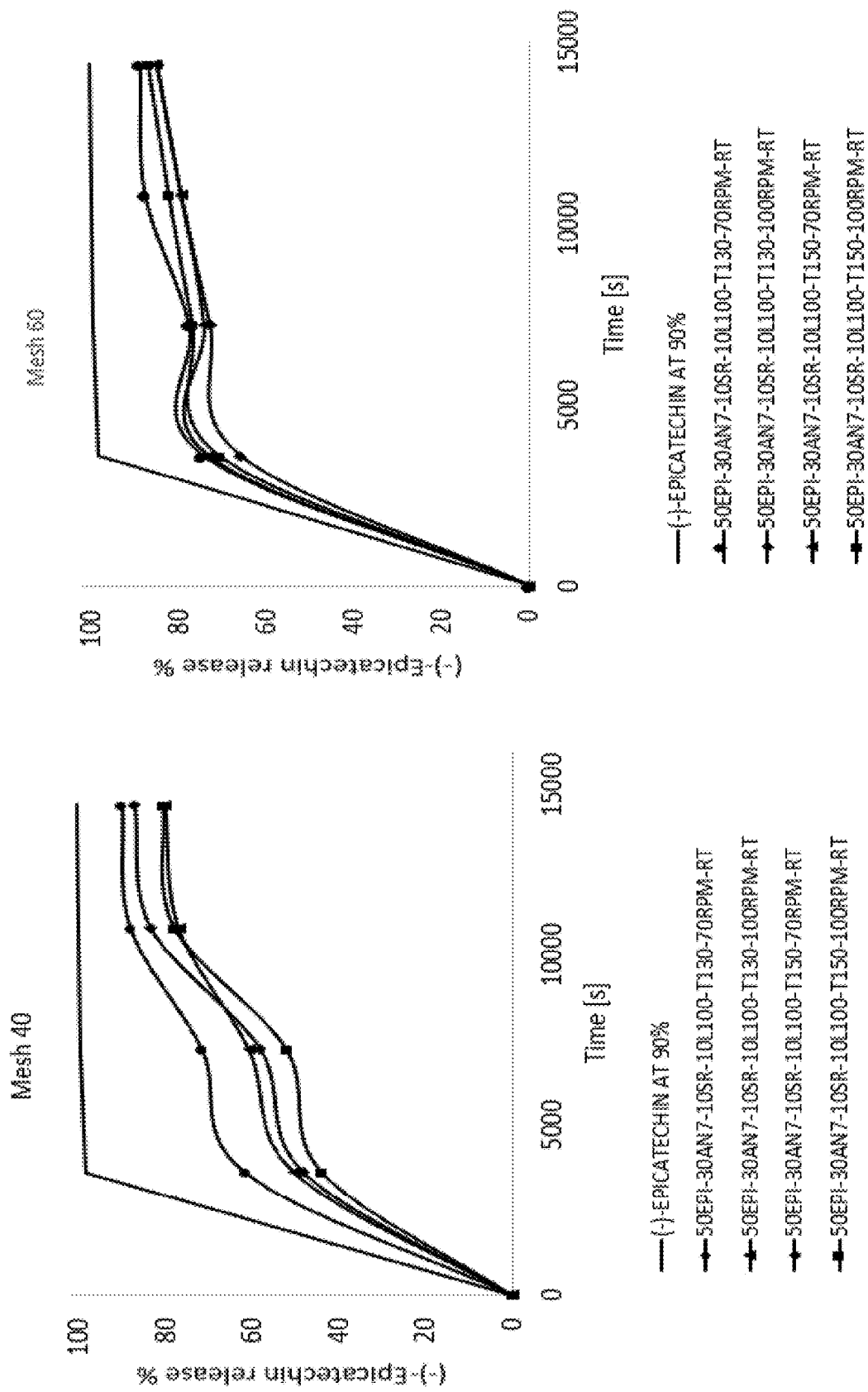

FIG. 22 features release profile of (−)-Epicatechin at 2 hour in a medium with pH of 1.2 and 2 more hours in a medium with pH of 6.8, at 37° C. Releases for examples X to XIII with a particle size distribution between 250 μm and 425 μm (Mesh 40); and particle size distribution between 180 μm and 250 μm (Mesh 60).

Table 11 below describes the release profile percentages for EXAMPLES X to XIII with a particle size distribution between 250 μm and 425 μm (Mesh 40); and particle size distribution between 180 μm and 250 μm (Mesh 60).

TABLE 11

| Samples | Time | | | | | | |
|---|---|---|---|---|---|---|---|
| | 30 s % release | 60 s % release | 120 s % release | 1 h % release | 2 h % release | 3 h % release | 4 h % release |
| EPICATECHIN AT 90% | 75.30 | 88.70 | 93.43 | 98.59 | 99.94 | 100.22 | 100.84 |
| 50EPI-30AN7-10SR-10L100-T130-70 rpm-RT-Mesh 40 | 7.01 | 10.36 | 14.35 | 61.80 | 71.78 | 88.41 | 90.23 |
| 50EPI-30AN7-10SR-10L100-T130-100 rpm-RT-Mesh 40 | 4.77 | 6.33 | 11.72 | 50.23 | 60.80 | 77.08 | 80.09 |
| 50EPI-30AN7-10SR-10L100-T150-70 rpm-RT-Mesh 40 | 4.97 | 10.39 | 14.15 | 48.25 | 58.27 | 83.80 | 87.44 |
| 50EPI-30AN7-10SR-10L100-T150-100 rpm-RT-Mesh 40 | 7.09 | 10.36 | 12.86 | 43.92 | 52.10 | 78.20 | 80.73 |
| 50EPI-30AN7-10SR-10L100-T130-70 rpm-RT-Mesh 60 | 9.50 | 16.09 | 26.67 | 75.01 | 78.11 | 88.15 | 89.23 |
| 50EPI-30AN7-10SR-10L100-T130-100 rpm-RT-Mesh 60 | 8.35 | 14.50 | 17.79 | 66.27 | 73.17 | 79.74 | 85.23 |
| 50EPI-30AN7-10SR-10L100-T150-70 rpm-RT-Mesh 60 | 8.10 | 10.36 | 16.71 | 73.63 | 74.51 | 79.77 | 85.33 |
| 50EPI-30AN7-10SR-10L100-T150-100 rpm-RT-Mesh 60 | 8.93 | 11.87 | 20.26 | 71.05 | 77.03 | 82.41 | 87.15 |

Example XIV

50EPI-30ES10-10L100-10SR-T130-70RPM-RT
50% (−)-Epicatechin (90%)
30% Ethocel Standard 10 (Dow polymer)
10% Eudragit L100 (Evonik polymer)
10% Kollidon SR (Basf polymer)
Process Conditions: batch melt mixing at 70 RPM and processing temperature of 130° C.

Example XV

50EPI-30ES10-10L100-10SR-T130-100RPM-RT
50% (−)-Epicatechin (90%)
30% Ethocel Standard 10 (Dow polymer)
10% Eudragit L100 (Evonik polymer)
10% Kollidon SR (Basf polymer)
Process Conditions: batch melt mixing at 100 RPM and processing temperature of 130° C.

Example XVI

50EPI-30ES10-10L100-10SR-T150-70RPM-RT
50% (−)-Epicatechin (90%)
30% Ethocel Standard 10 (Dow polymer)
10% Eudragit L100 (Evonik polymer)
10% Kollidon SR (Basf polymer)
Process Conditions: batch melt mixing at 70 RPM and processing temperature 150° C.

Example XVII

50EPI-30ES10-10L100-10SR-T150-100RPM-RT
50% (−)-Epicatechin (90%)
30% Ethocel Standard 10 (Dow polymer)
10% Eudragit L100 (Evonik polymer)
10% Kollidon SR (Basf polymer)
Process Conditions: batch melt mixing at 100 RPM and processing temperature 150° C.

Figure 23:
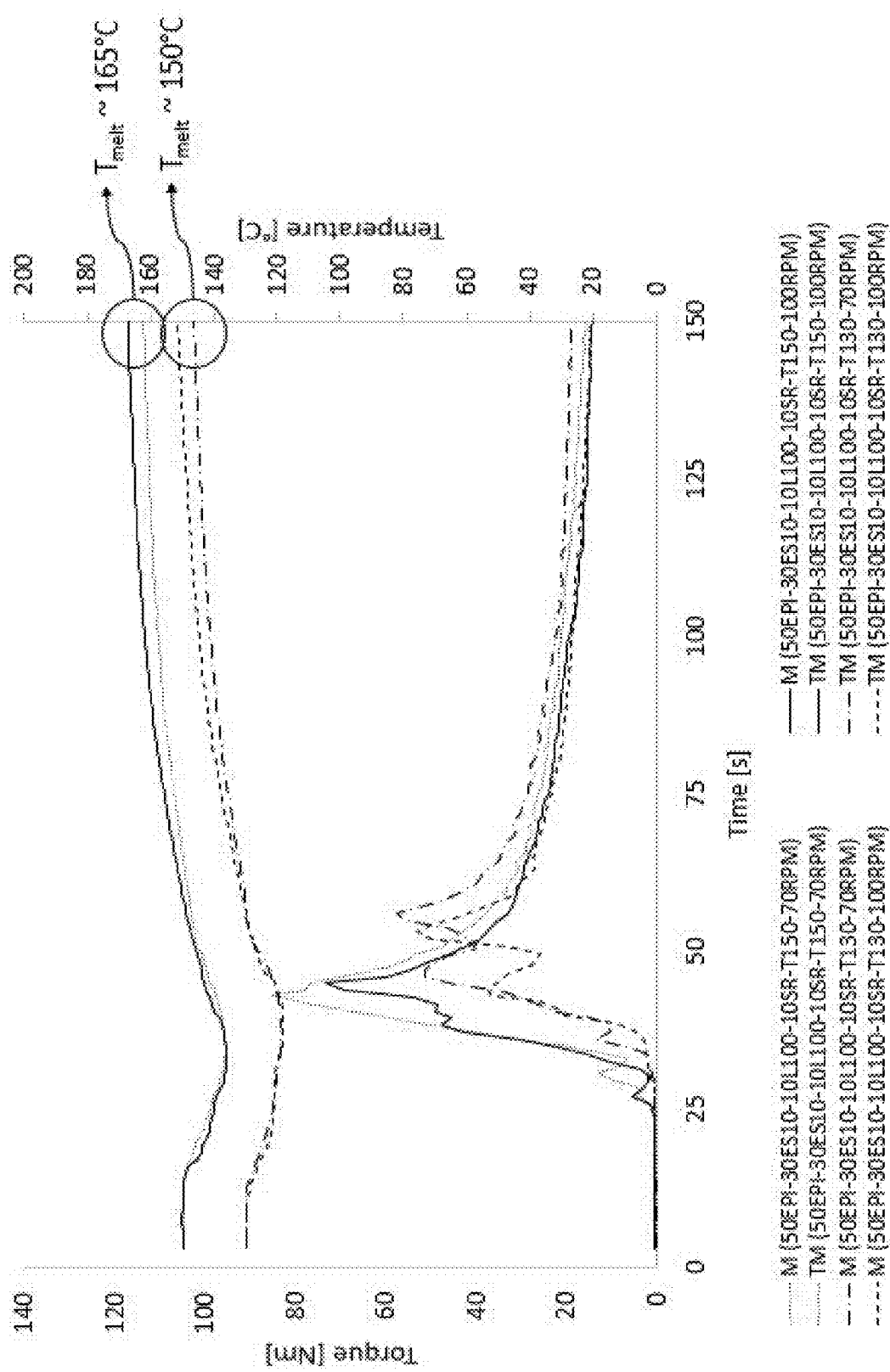
FIG. 23 illustrates the torque and melt temperature behavior of examples XIV to XVII.

FIG. 23 illustrates the torque and melt temperature behavior of examples XIV to XVII.

Figure 24:
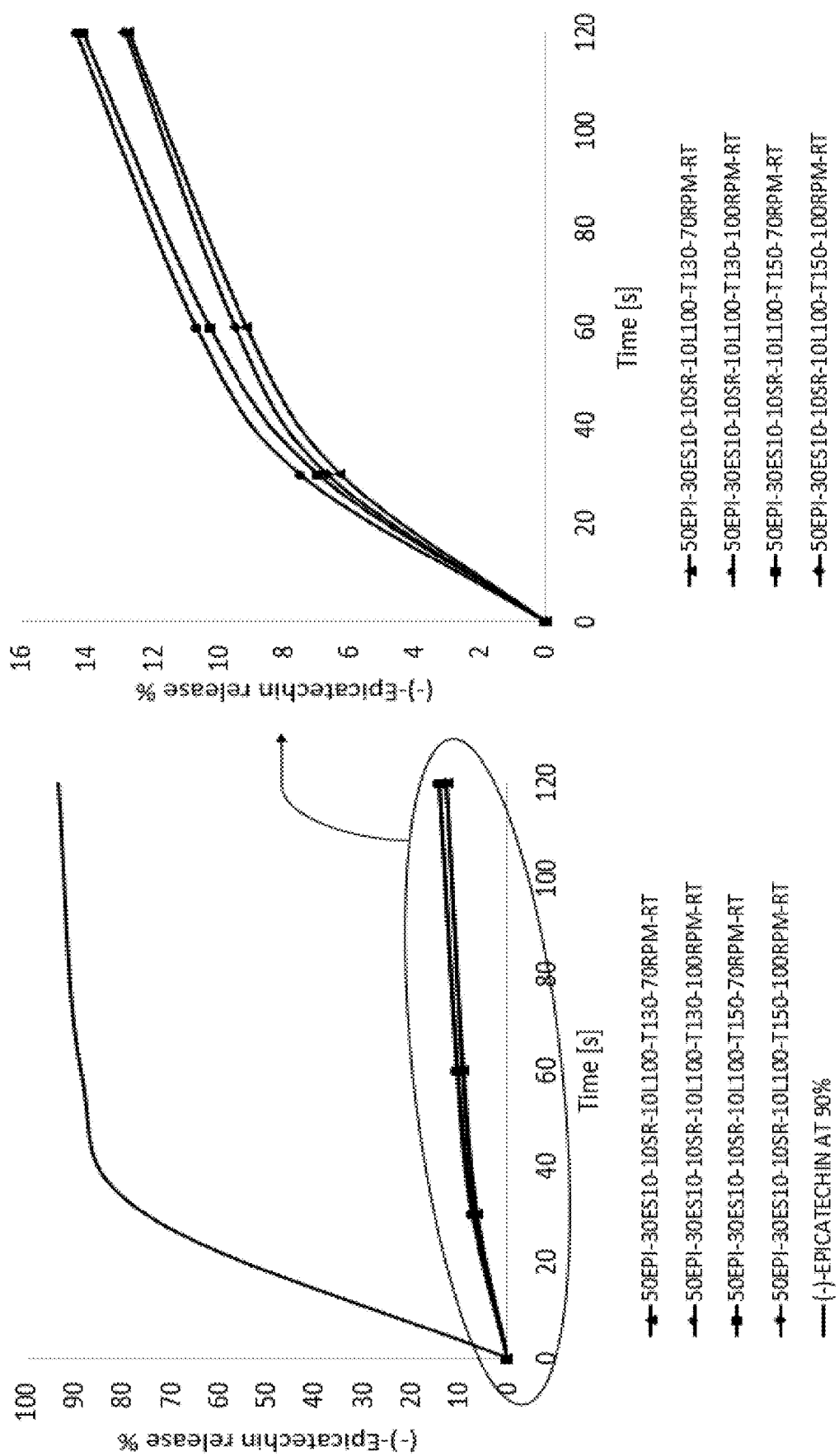
FIG. 24 shows the release profile of (−)-Epicatechin in artificial saliva at pH 6.2 and 23° C. for examples X to XIII at given particle size distribution.

FIG. 24 shows the release profile of (−)-Epicatechin in artificial saliva at pH 6.2 and 23° C. for examples X to XIII with a particle size distribution between 250 μm and 425 μm (Mesh 40).

Figure 25:
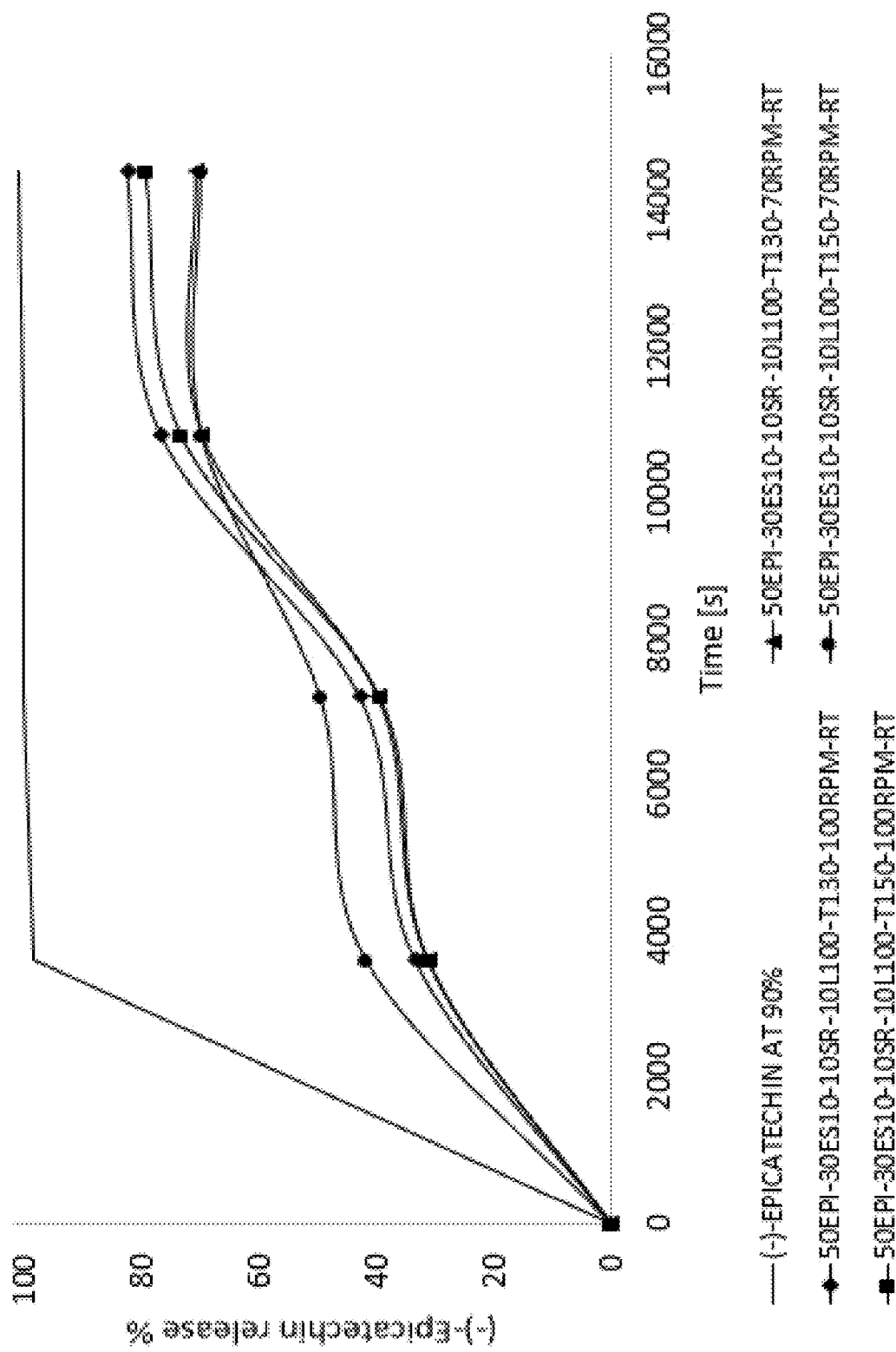
FIG. 25 features the release profile of (−)-Epicatechin at 2 hour in a medium with pH of 1.2 and 2 more hours in a medium with pH of 6.8, at 37° C. for examples X to XIII

FIG. 25 features the release profile of (−)-Epicatechin at 2 hour in a medium with pH of 1.2 and 2 more hours in a medium with pH of 6.8, at 37° C. Releases for EXAMPLES X to XIII with a particle size distribution between 250 μm and 425 μm (Mesh 40).

Table 12 below shows the dissolution release percentages for EXAMPLES X to XIII with a particle size distribution between 250 μm and 425 μm (Mesh 40).

TABLE 12

| | Time | | | | | | |
|---|---|---|---|---|---|---|---|
| Samples | 30 s % release | 60 s % release | 120 s % release | 1 h % release | 2 h % release | 3 h % release | 4 h % release |
| 50EPI-30ES10-10SR-10L100-T130-70 rpm-RT | 6.31 | 9.17 | 12.78 | 31.35 | 39.79 | 69.97 | 70.99 |
| 50EPI-30ES10-10SR-10L100-T130-100 rpm-RT | 7.52 | 10.69 | 14.35 | 33.38 | 42.74 | 76.81 | 82.44 |
| 50EPI-30ES10-10SR-10L100-T150-70 rpm-RT | 6.97 | 10.27 | 14.14 | 41.80 | 49.60 | 69.95 | 70.09 |
| 50EPI-30ES10-10SR-10L100-T150-100 rpm-RT | 6.70 | 9.52 | 12.88 | 31.12 | 39.36 | 73.36 | 79.32 |

Example XVIII

50EPI-30AN7-10L100-10SR-T160-250RPM-AS70-C2.3
50%(−)-Epicatechin (90%)
30% Aqualon N7 (Ashland polymer)
10% Eudragit L100 (Evonik polymer)
10% Kollidon SR (Basf polymer)
Process Conditions: twin screw extrusion (Nano 16 Leistritz) at 250 RPM (co-rotating screws), temperature profile: 160° C. (feed zone), 165° C., 145° C. (metering zone), 145° C. (die); feeding rate of volumetric feeder at 680 g/h; and estimated filling factor 33%.

Figure 26:
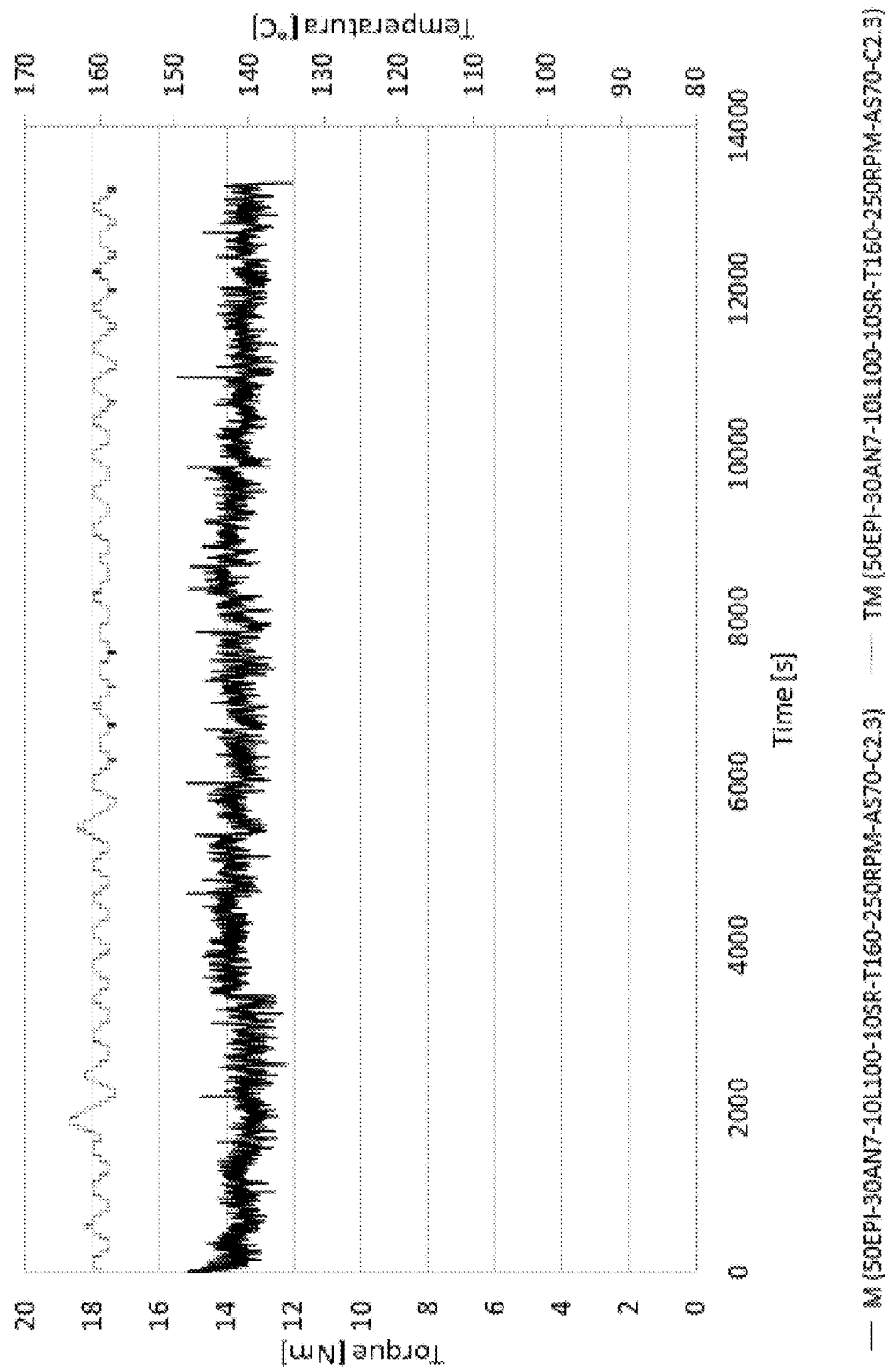
FIG. 26 illustrates the torque and melt temperature behavior of example XVIII.

FIG. 26 illustrates the torque and melt temperature behavior of example XVIII.

Figure 27:
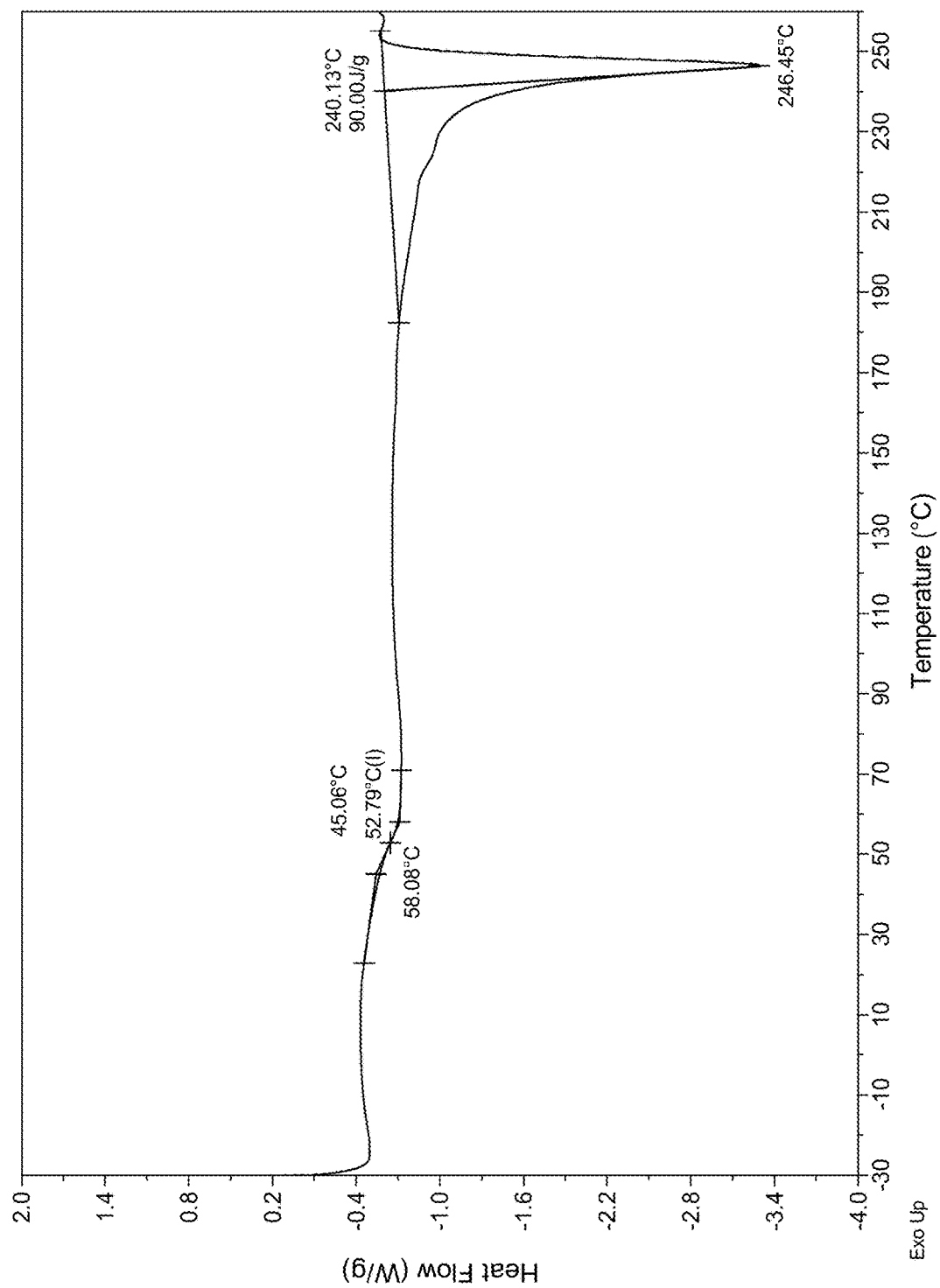
FIG. 27 shows the thermal characterization of example XVIII.

FIG. 27 shows the thermal characterization of EXAMPLE XVIII.

Figure 28:
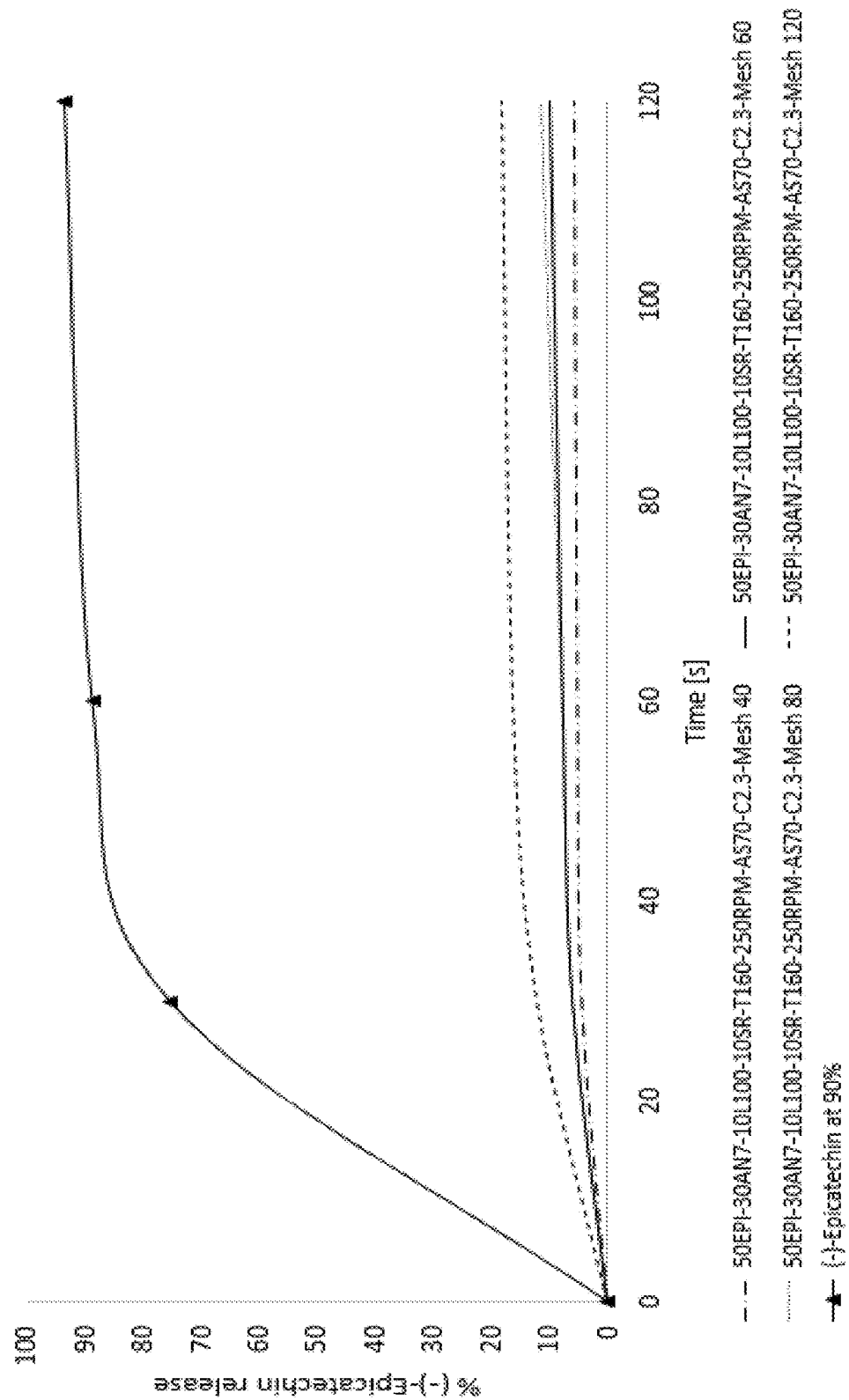
FIG. 28 describes the release profile of (−)-Epicatechin in artificial saliva at pH 6.2 and 23° C. for example XVIII.

FIG. 28 describes the release profile of (−)-Epicatechin in artificial saliva at pH 6.2 and 23° C. for example XVIII with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

Figure 29:
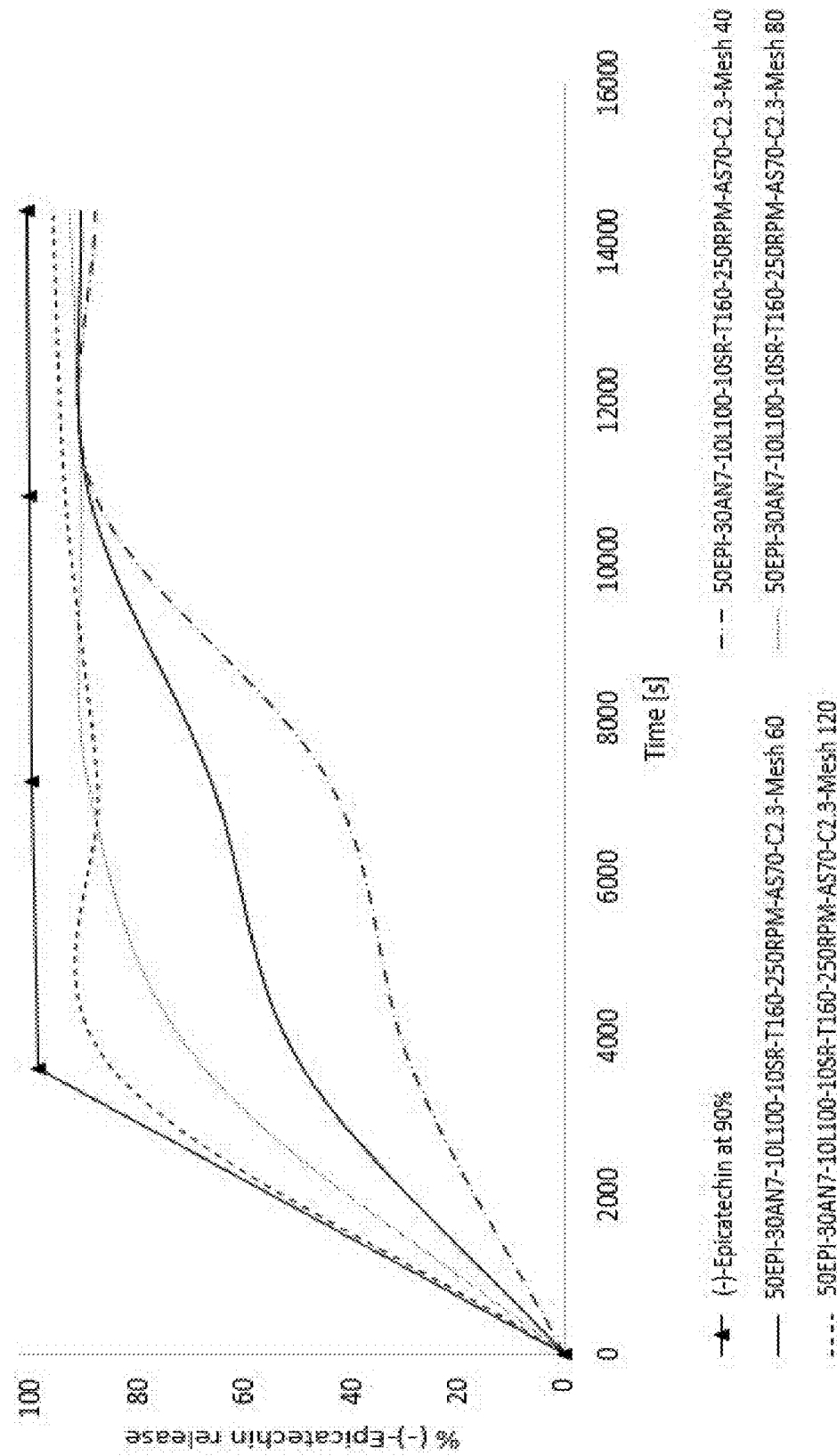
FIG. 29 features the release profile of (−)-Epicatechin at 2 hour in a medium with pH of 1.2 and 2 more hours in a medium with pH of 6.8, at 37° C. for example XVIII.

FIG. 29 features the release profile of (−)-Epicatechin at 2 hour in a medium with pH of 1.2 and 2 more hours in a medium with pH of 6.8, at 37° C. Releases for EXAMPLE XVIII with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

Table 13 illustrates the release profile percentages for EXAMPLE XVIII with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

TABLE 13

| Samples | 30 s % | 60 s % | 120 s % | 1 h % | 2 h % | 3 h % | 4 h % |
|---|---|---|---|---|---|---|---|
| (−)-EPICATECHIN AT 90% | 75.30 | 88.70 | 93.43 | 98.59 | 99.94 | 100.22 | 100.84 |
| 50EPI-30AN7-10L100-10SR-T160-250 RPM-AS70-C2.3-Mesh 40 | 4.28 | 4.99 | 5.53 | 28.71 | 44.11 | 88.00 | 88.02 |
| 50EPI-30AN7-10L100-10SR-T160-250 RPM-AS70-C2.3-Mesh 60 | 5.93 | 7.59 | 9.75 | 49.01 | 66.04 | 89.02 | 90.58 |
| 50EPI-30AN7-10L100-10SR-T160-250 RPM-AS70-C2.3-Mesh 80 | 6.02 | 7.86 | 11.37 | 67.72 | 89.55 | 90.75 | 93.00 |
| 50EPI-30AN7-10L100-10SR-T160-250 RPM-AS70-C2.3-Mesh 120 | 12.10 | 16.28 | 18.23 | 84.95 | 87.62 | 93.71 | 95.93 |

Example XIX

50EPI-30ES10-10L100-10SR-T160-270RPM-AS70-C2.3
50% Epicatechin (90%)
30% Ethocel Standard 10 (Dow polymer)
10% Eudragit L100 (Evonik polymer)
10% Kollidon SR (Basf polymer)

Process Conditions: twin screw extrusion (Nano 16 Leistritz) at 250 RPM (co-rotating screws), temperature profile: 160° C. (feed zone), 165° C., 145° C. (metering zone), 145° C. (die); feeding rate of volumetric feeder at 680 g/h; and estimated filling factor 31%.

Figure 30:
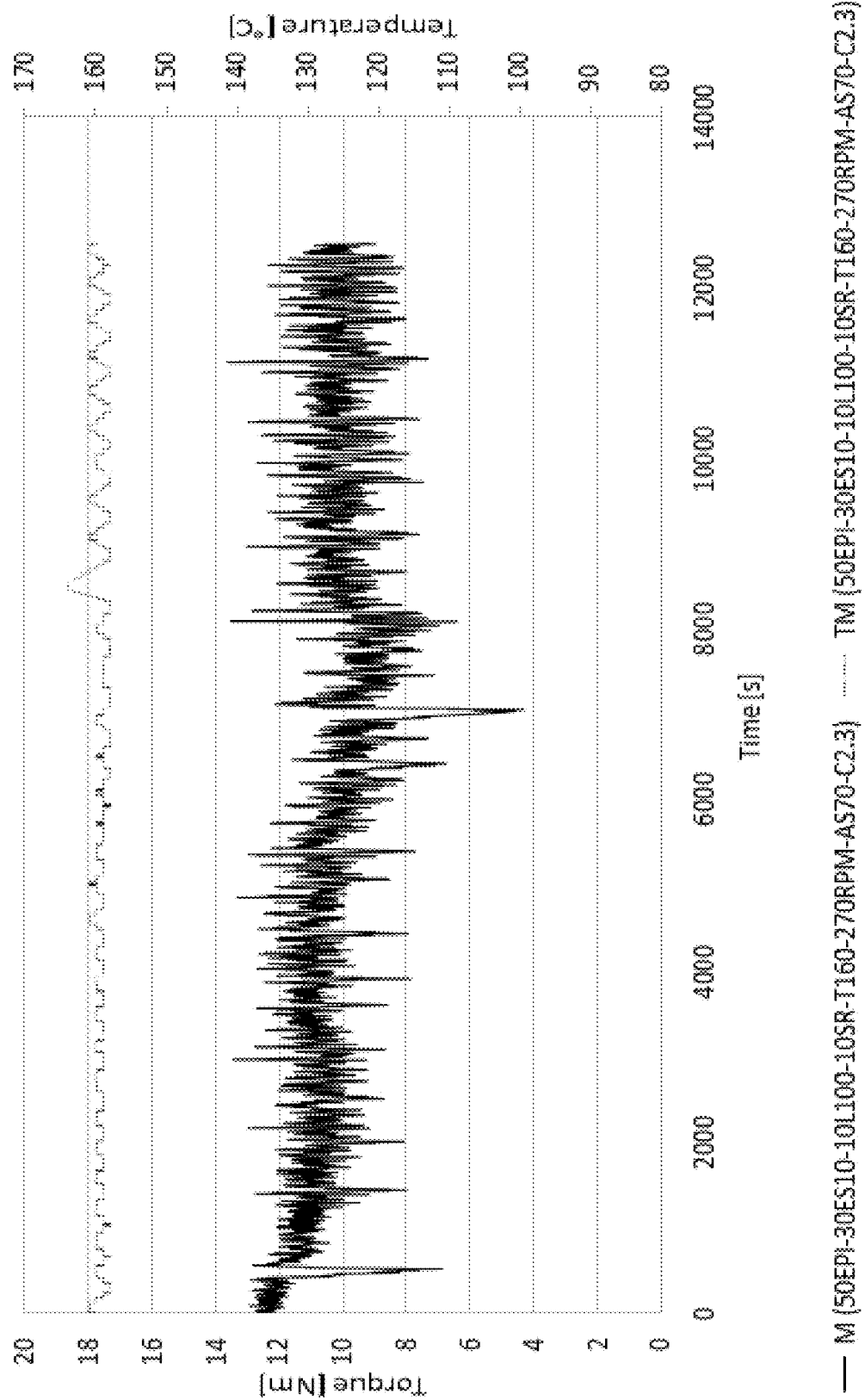
FIG. 30 describes the torque and melt temperature behavior of example XIX.

FIG. 30 describes the torque and melt temperature behavior of example XIX.

Figure 31:
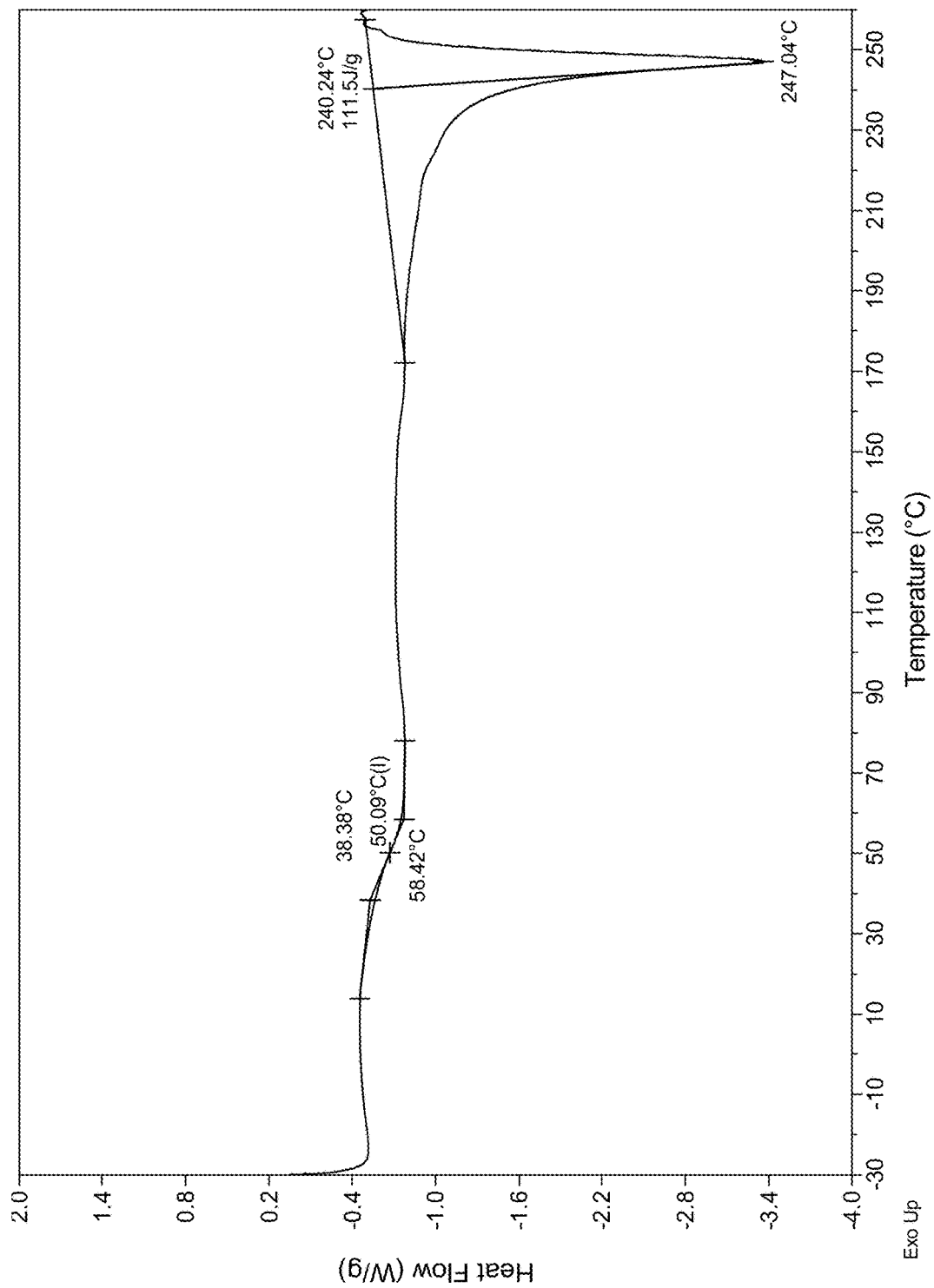
FIG. 31 illustrates the thermal characterization of example XIX.

FIG. 31 illustrates the thermal characterization of example XIX.

Figure 32:
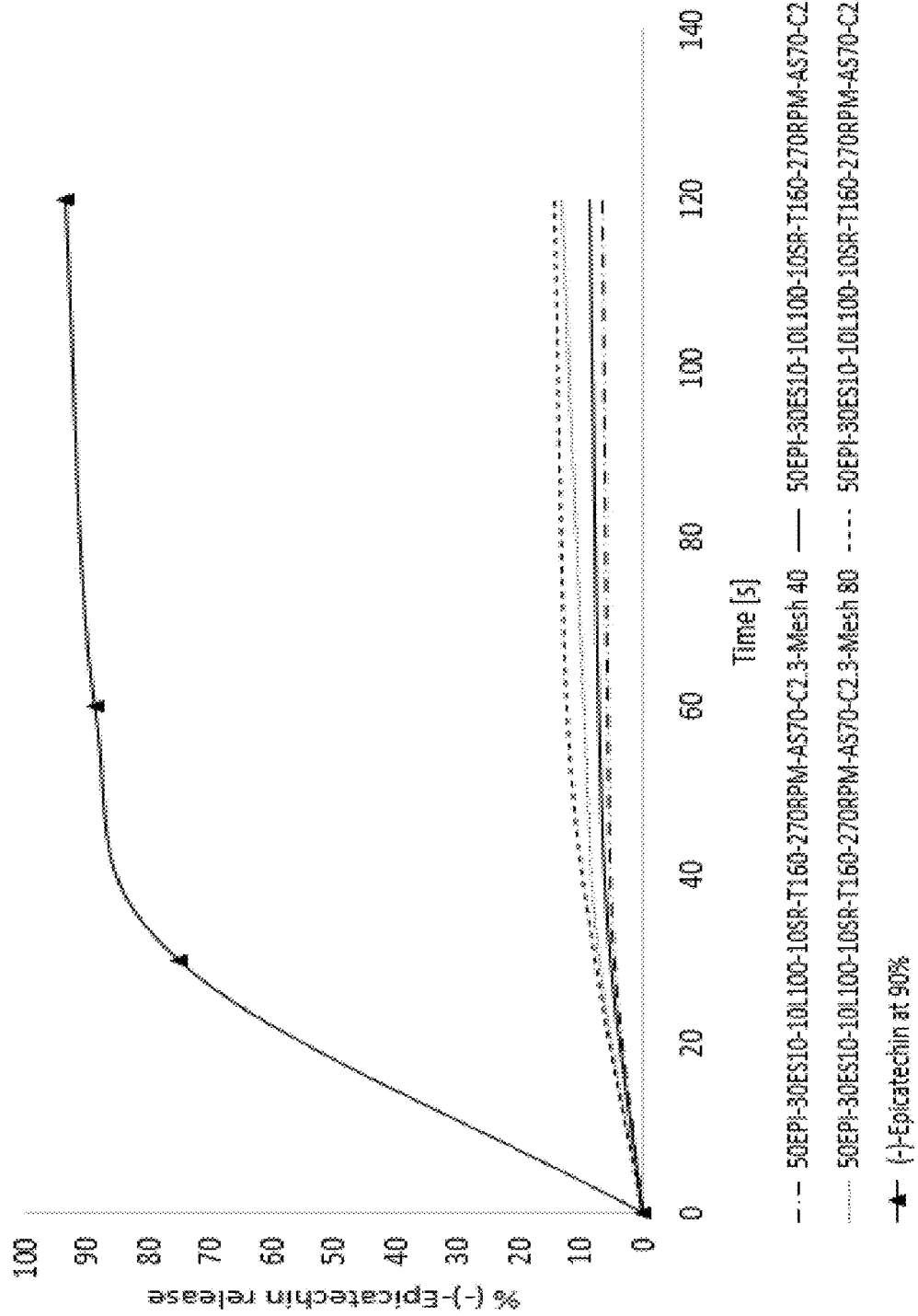
FIG. 32 shows the release profile of (−)-Epicatechin in artificial saliva at pH 6.2 and 23° C. for example XIX.

FIG. 32 shows the release profile of (−)-Epicatechin in artificial saliva at pH 6.2 and 23° C. for example XIX with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

Figure 33:
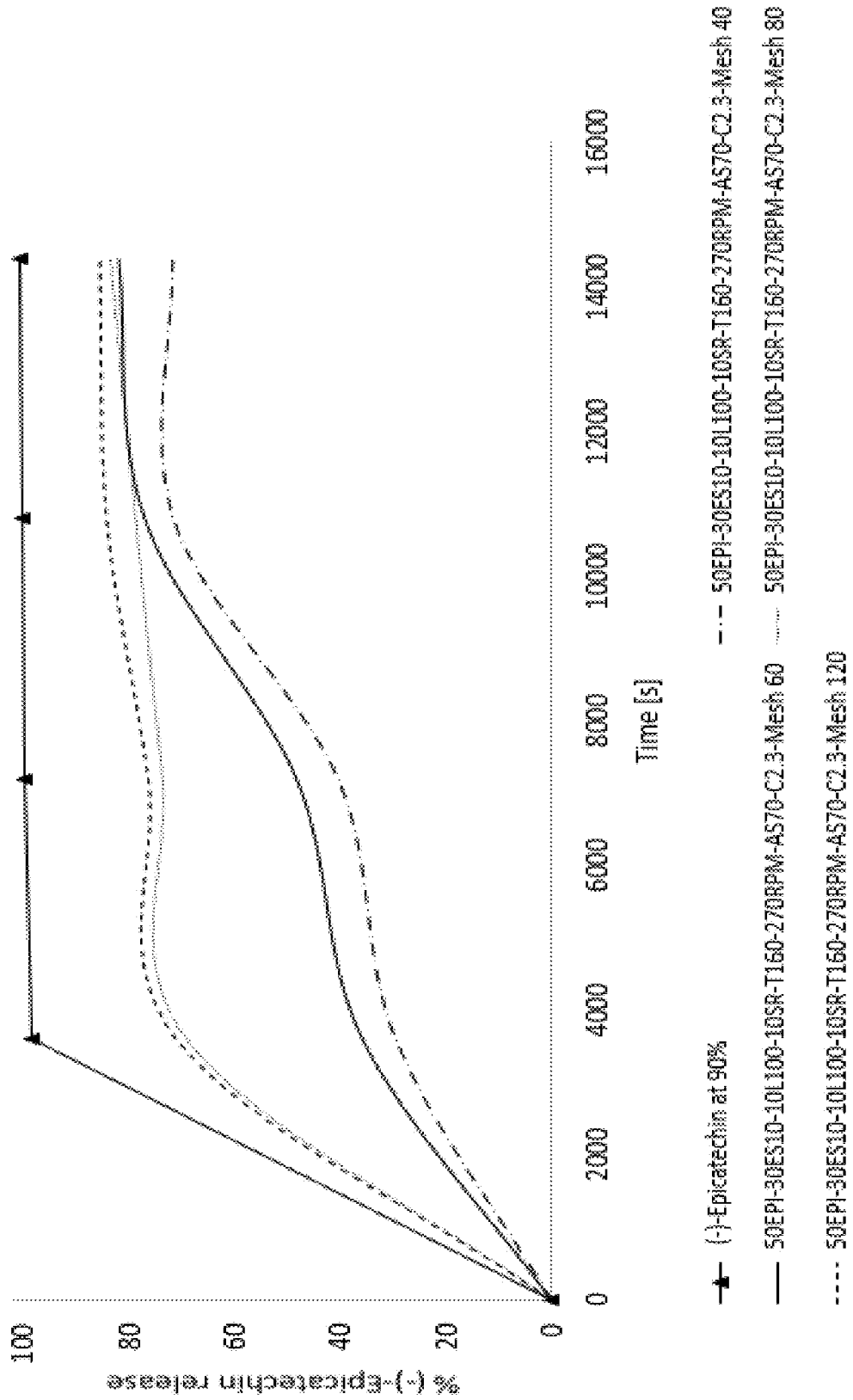
FIG. 33 describes the release profile of (−)-Epicatechin at 2 hour in a medium with pH of 1.2 and 2 more hours in a medium with pH of 6.8, at 37° C. for example XIX.

FIG. 33 describes the release profile of (−)-Epicatechin at 2 hour in a medium with pH of 1.2 and 2 more hours in a medium with pH of 6.8, at 37° C. Releases for example XIX with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

Table 14 shows the release profile percentages for EXAMPLE XIX with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120):

TABLE 14

| Samples | 30 s % | 60 s % | 120 s % | 1 h % | 2 h % | 3 h % | 4 h % |
|---|---|---|---|---|---|---|---|
| (−)-EPICATECHIN AT 90% | 75.30 | 88.70 | 93.43 | 98.59 | 99.94 | 100.22 | 100.84 |
| 50EPI-30ES10-10L100-10SR-T160-270 RPM-AS70-C2.3-Mesh 40 | 4.78 | 5.89 | 6.81 | 29.53 | 40.44 | 71.69 | 71.83 |
| 50EPI-30ES10-10L100-10SR-T160-270 RPM-AS70-C2.3-Mesh 60 | 5.37 | 7.37 | 8.84 | 35.82 | 48.34 | 77.21 | 82.15 |
| 50EPI-30ES10-10L100-10SR-T160-270 RPM-AS70-C2.3-Mesh 80 | 7.21 | 9.72 | 13.31 | 69.01 | 73.67 | 78.77 | 83.53 |
| 50EPI-30ES10-10L100-10SR-T160-270 RPM-AS70-C2.3-Mesh 120 | 7.81 | 12.38 | 14.42 | 71.19 | 76.57 | 84.52 | 85.77 |

Example XX

50EXT-30ES10-10L100-10SR-T155-400RPM-AS70-C2.3
50% Cocoa Extract
30% Ethocel Standard 10 (Dow polymer)
10% Eudragit L100 (Evonik polymer)
10% Kollidon SR (Basf polymer)

Process Conditions: twin screw extrusion (Nano 16 Leistritz) at 400 RPM (co-rotating screws) and temperature profile: 165° C. (feed zone), 150° C., 140° C. (metering zone), 140° C. (die); feeding rate of volumetric feeder at 990 g/h, and estimated filling factor 26%.

Figure 34:
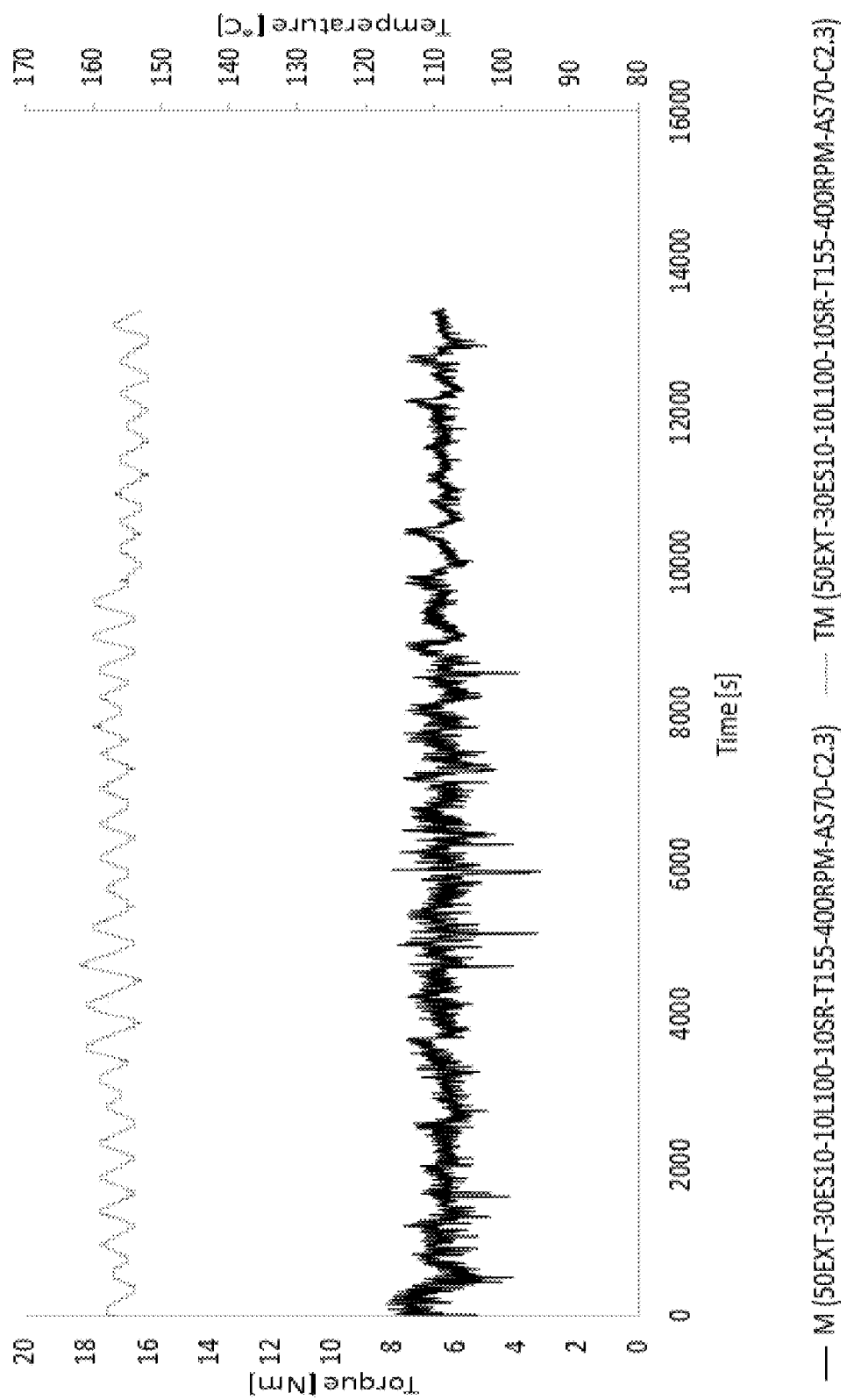
FIG. 34 illustrates the torque and melt temperature behavior of example XX.

FIG. 34 illustrates the torque and melt temperature behavior of example XX.

Figure 35:
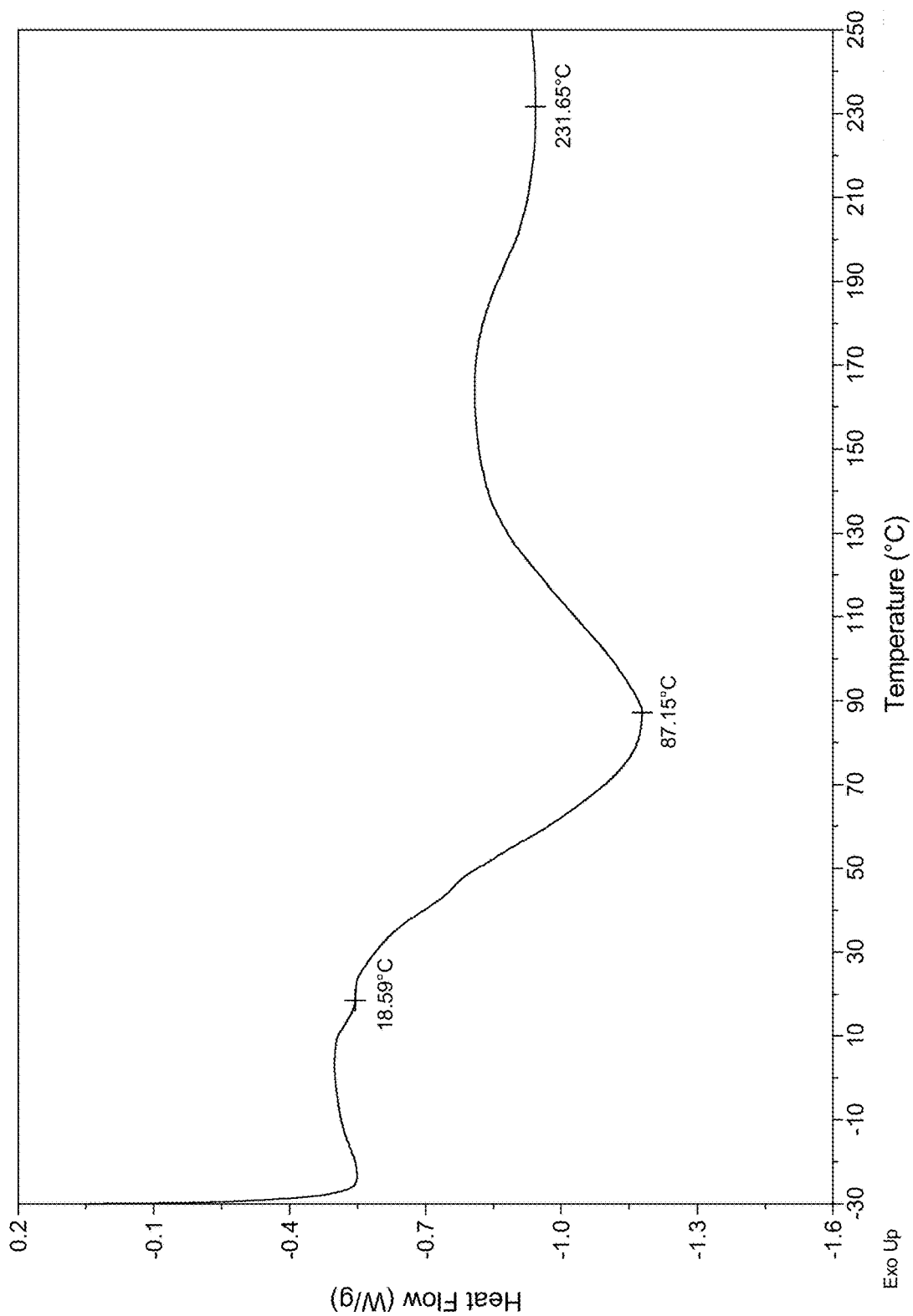
FIG. 35 features the thermal characterization of example XX.

FIG. 35 features the thermal characterization of example XX.

Figure 36:
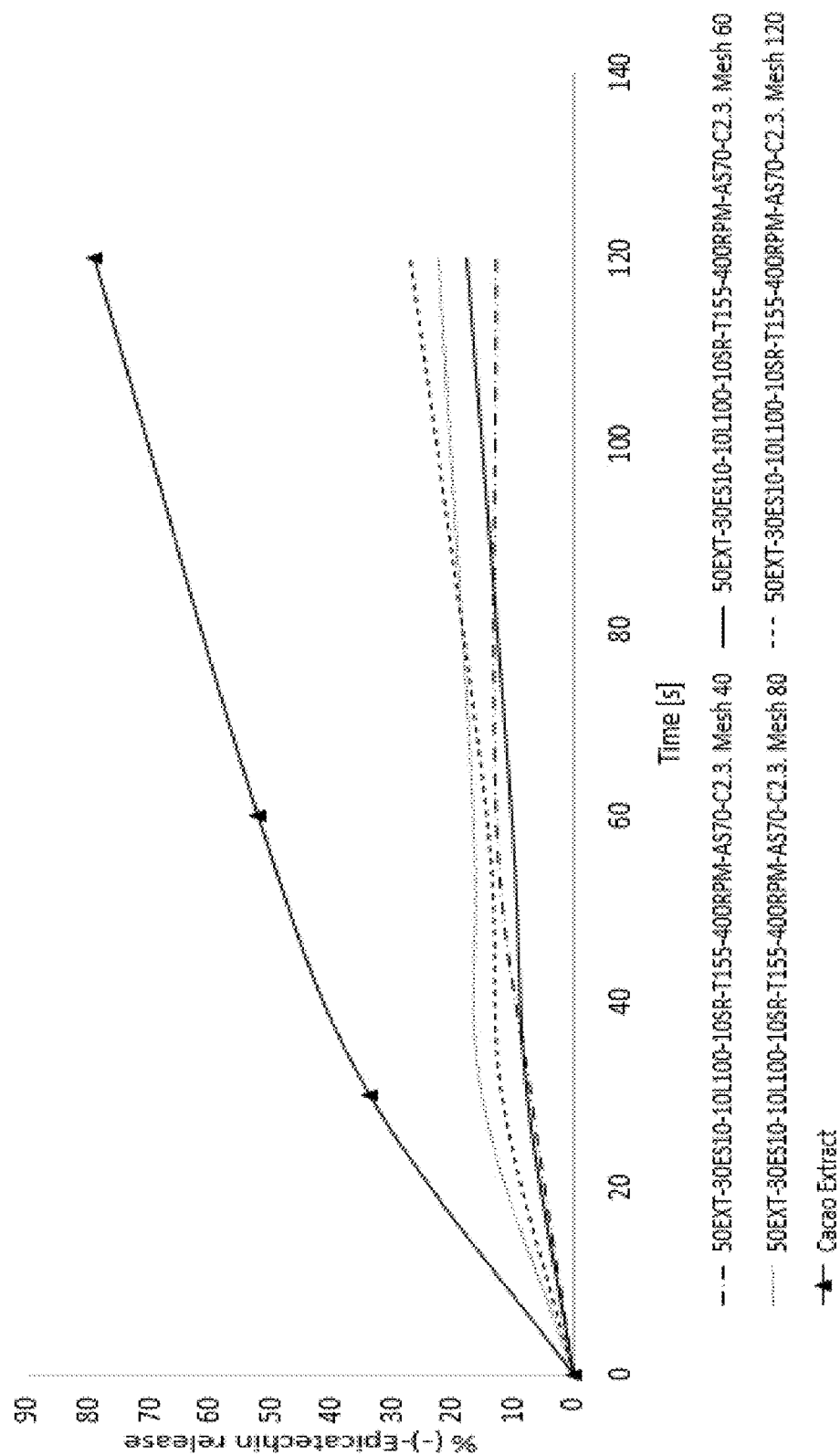
FIG. 36 illustrates the release profile of (−)-Epicatechin in artificial saliva at pH 6.2 and 23° C. for example XX.

FIG. 36 illustrates the release profile of (−)-Epicatechin in artificial saliva at pH 6.2 and 23° C. for example XX with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

Figure 37:
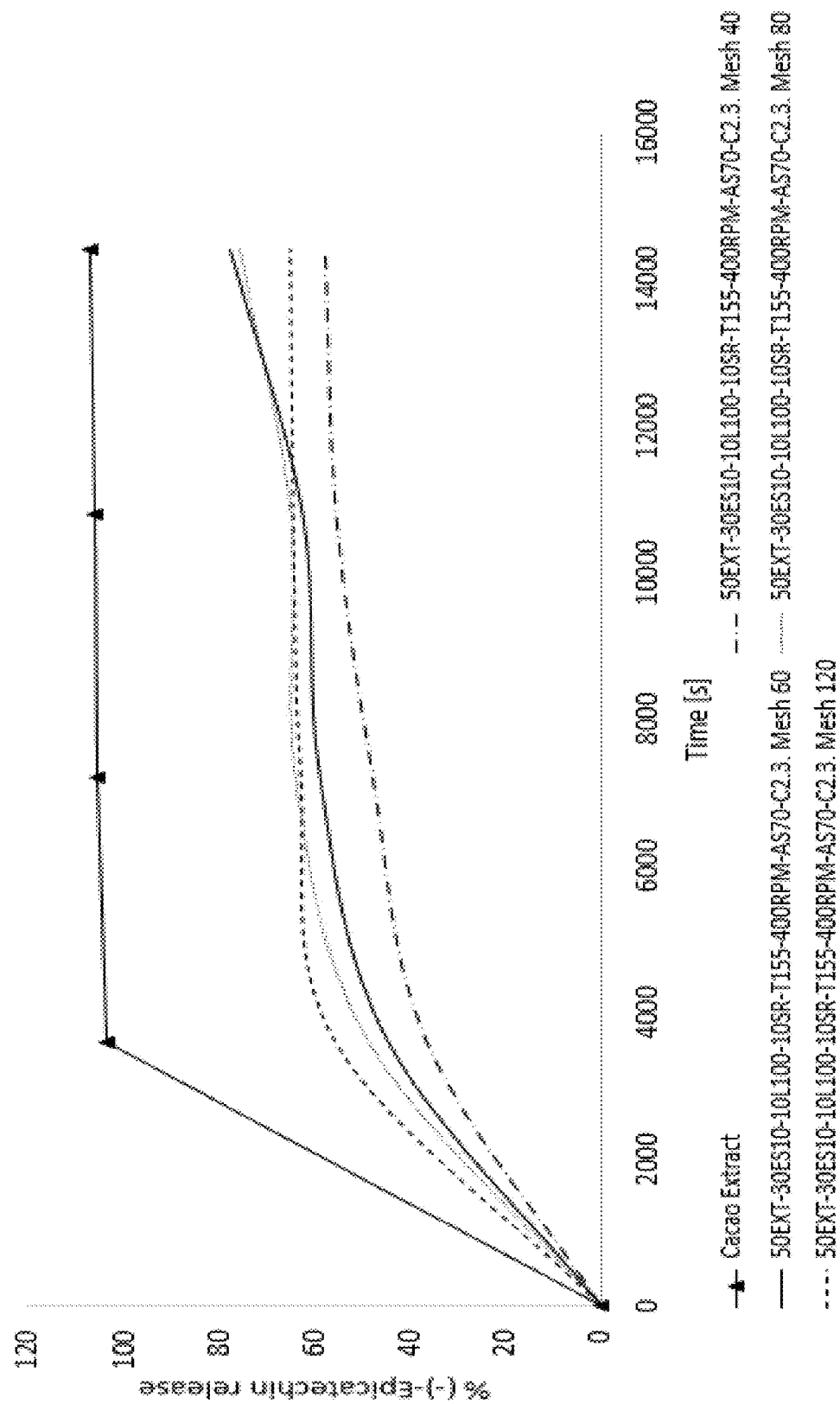
FIG. 37 describes the release profile of epicatechin at 2 hour in a medium with pH of 1.2 and 2 more hours in a medium with pH of 6.8, at 37° C. for example XX.

FIG. 37 describes the release profile of epicatechin at 2 hour in a medium with pH of 1.2 and 2 more hours in a medium with pH of 6.8, at 37° C. Releases for example XX with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

Table 15 features the release profile percentages for EXAMPLE XX with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120)

TABLE 15

| Samples | Time | | | | | | |
|---|---|---|---|---|---|---|---|
| | 30 s % | 60 s % | 120 s % | 1 h % | 2 h % | 3 h % | 4 h % |
| Cocoa Extract | 33.53 | 51.86 | 78.86 | 103.48 | 105.51 | 105.90 | 106.91 |
| 50EXT-30ES10-10L100-10SR-T155-400 RPM-AS70-C2.3-Mesh 40 | 7.12 | 12.83 | 12.83 | 36.48 | 47.65 | 55.36 | 57.59 |
| 50EXT-30ES10-10L100-10SR-T155-400 RPM-AS70-C2.3-Mesh 60 | 7.59 | 10.07 | 17.37 | 44.61 | 58.82 | 62.44 | 77.60 |
| 50EXT-30ES10-10L100-10SR-T155-400 RPM-AS70-C2.3-Mesh 80 | 15.00 | 16.38 | 22.10 | 48.67 | 63.89 | 64.87 | 75.58 |
| 50EXT-30ES10-10L100-10SR-T155-400 RPM-AS70-C2.3-Mesh 120 | 11.75 | 14.21 | 26.83 | 55.77 | 62.88 | 64.46 | 65.07 |

Example XXI

50EXT-30AN7-10L100-10 SR-T155-400RPM-AS73-C2.3

50% Cocoa Extract

30% Aqualon N7 (Ashland polymer)

10% Eudragit L100 (Evonik polymer)

10% Kollidon SR (Basf polymer)

Process Conditions: twin screw extrusion (Nano 16 Leistritz) at 400 RPM (co-rotating screws) and temperature profile: 165° C. (feed zone), 145° C., 140° C. (metering zone), 140° C. (die), feeding rate of volumetric feeder at 1.04 kg/h, and estimated filling factor 27%.

Figure 38:
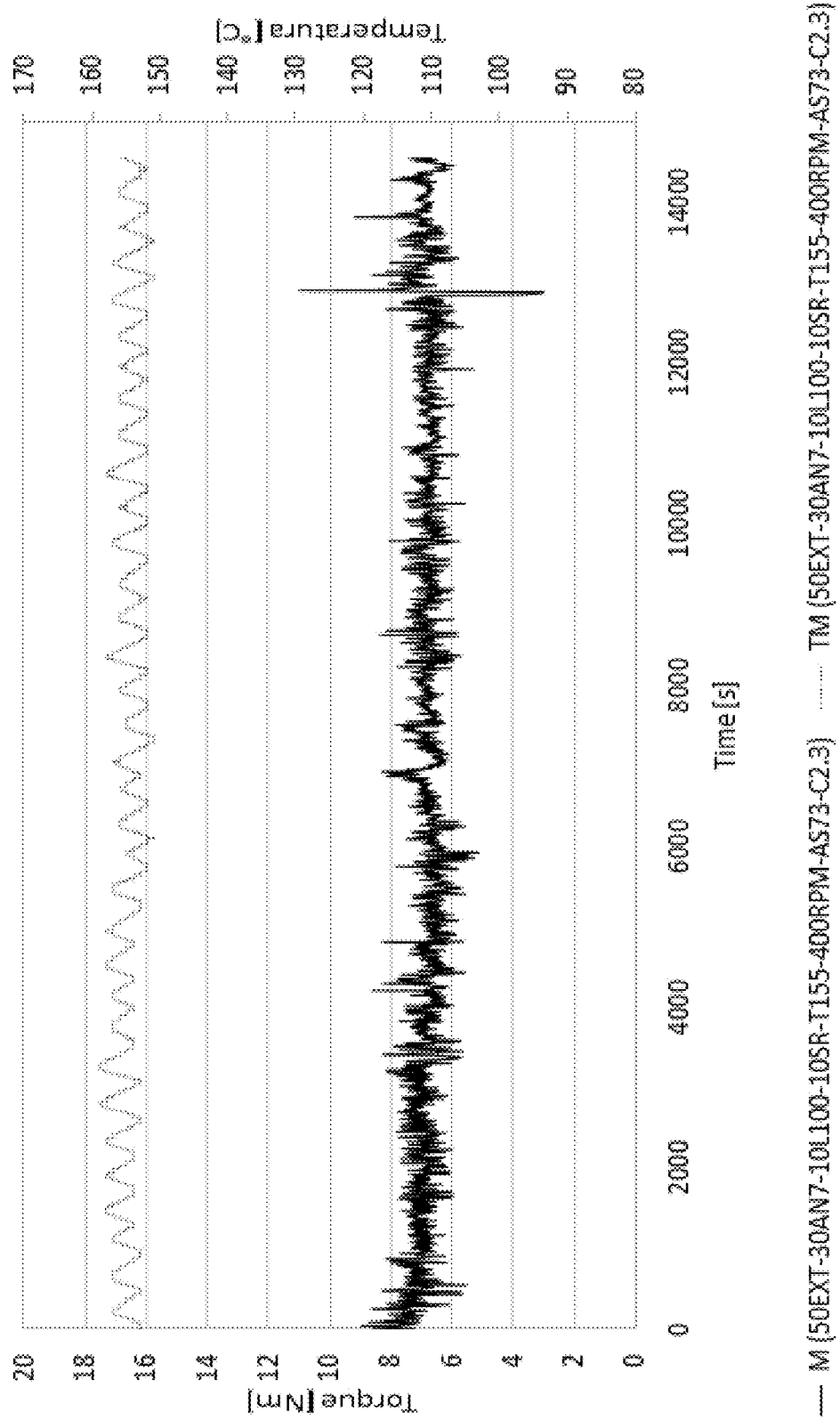
FIG. 38 shows the torque and melt temperature behavior of example XXI.

FIG. 38 shows the torque and melt temperature behavior of example XXI.

Figure 39:
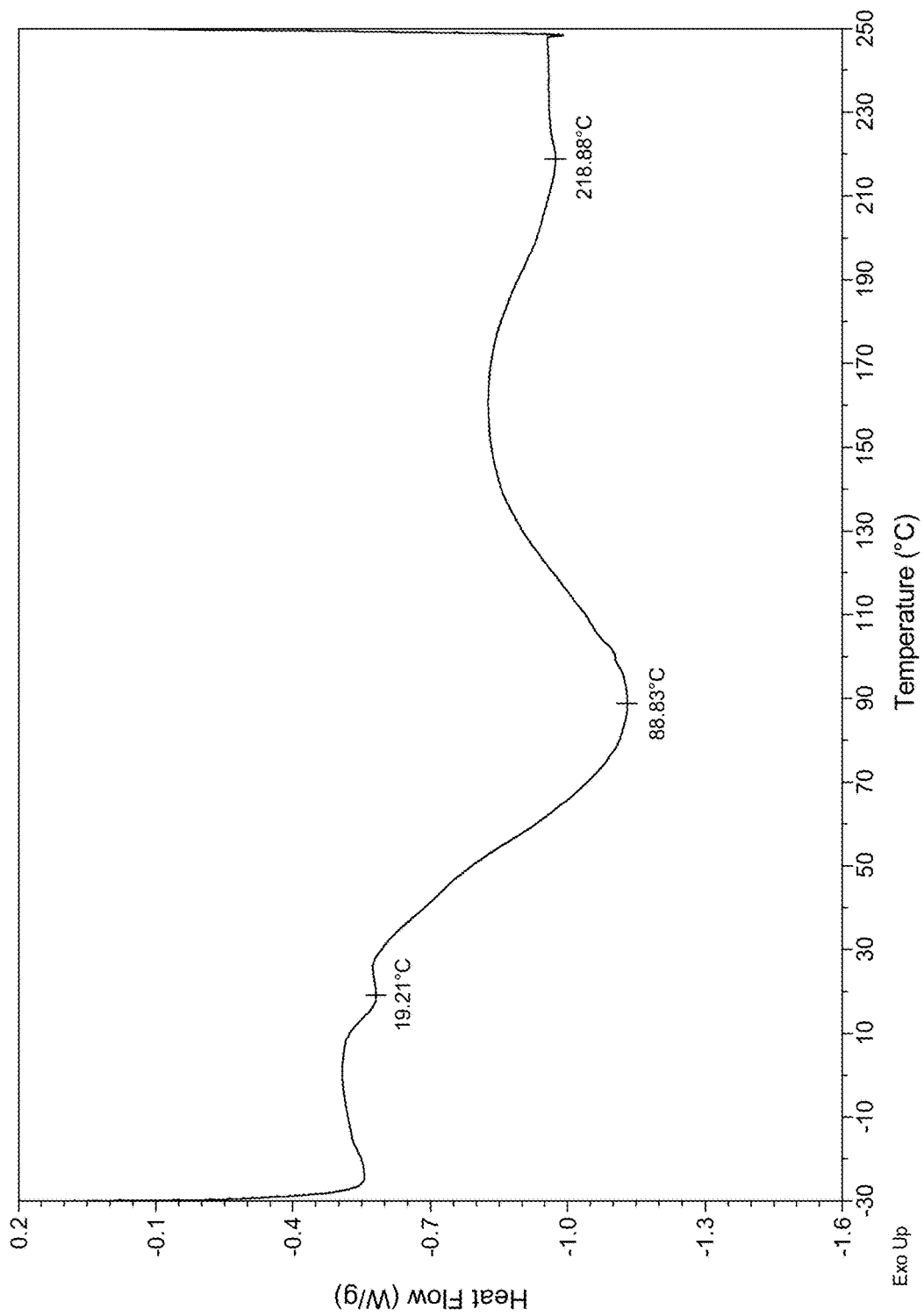
FIG. 39 describes the thermal characterization of example XXI.

FIG. 39 describes the thermal characterization of example XXI.

Figure 40:
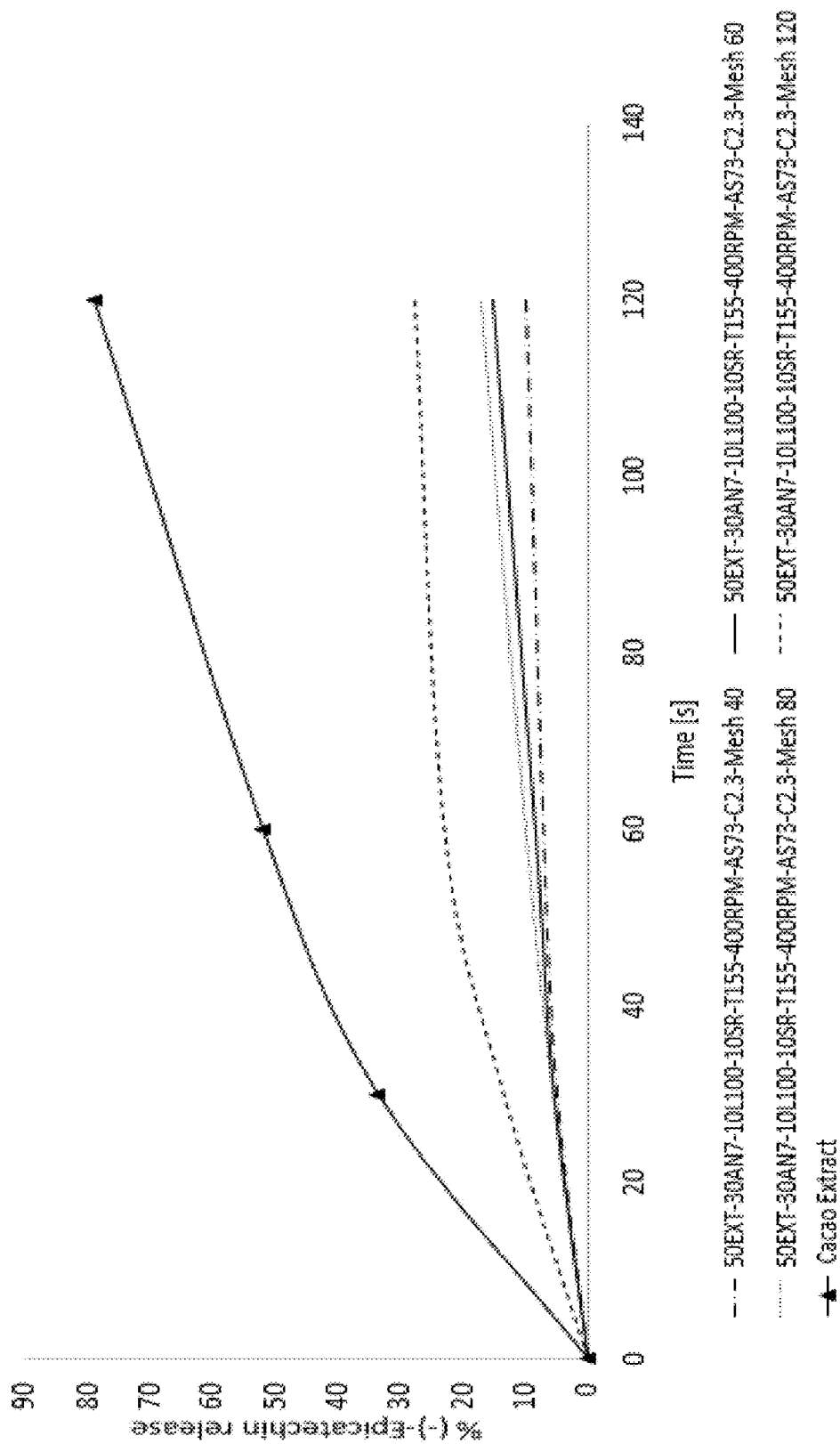
FIG. 40 illustrates the release profile of (−)-Epicatechin in artificial saliva at pH 6.2 and 23° C. for example XXI.

FIG. 40 illustrates the release profile of (−)-Epicatechin in artificial saliva at pH 6.2 and 23° C. for example XXI with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

Figure 41:
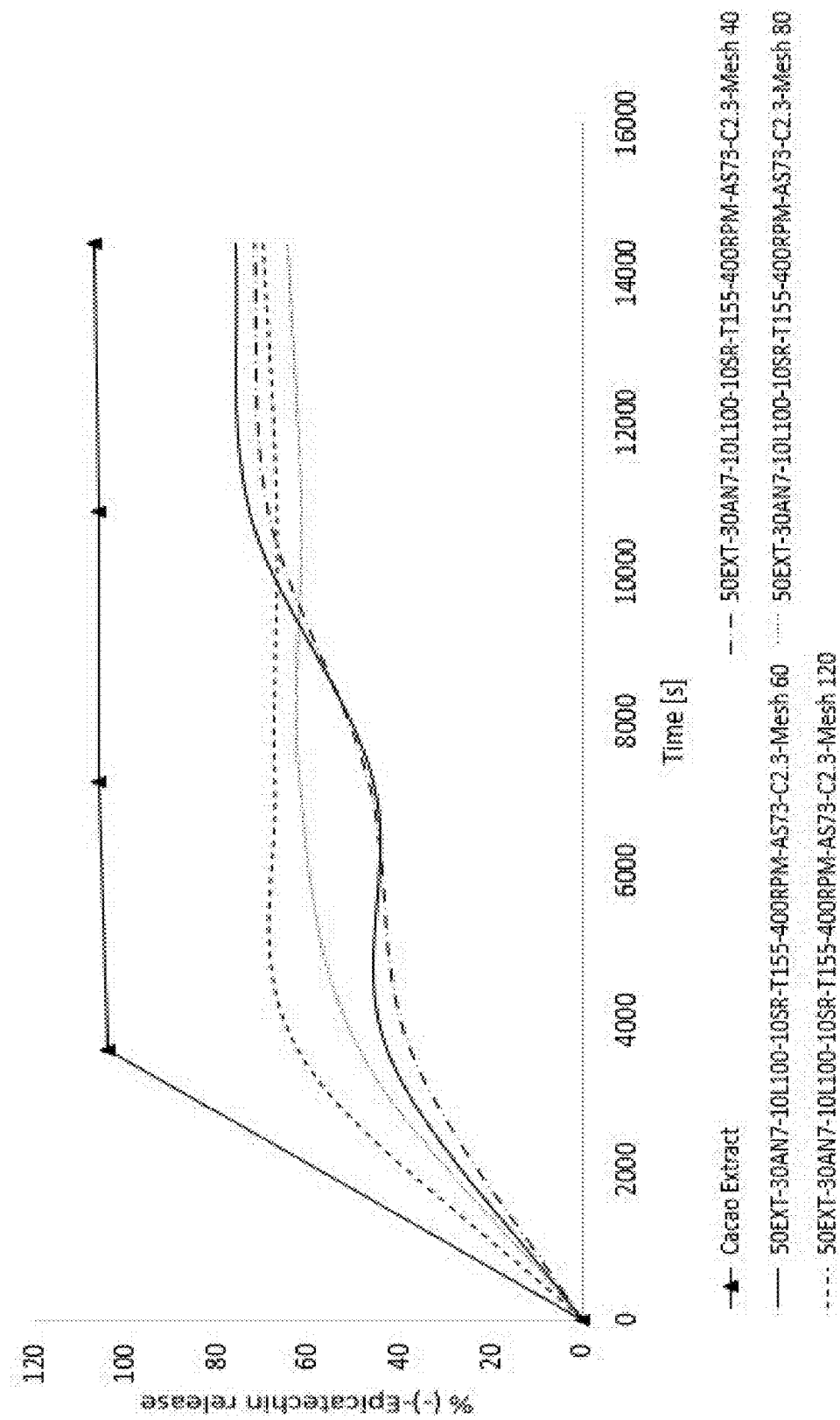
FIG. 41 shows the release profile of (−)-Epicatechin at 2 hour in a medium with pH of 1.2 and 2 more hours in a medium with pH of 6.8, at 37° C. for example XXI.

FIG. 41 shows the release profile of (−)-Epicatechin at 2 hour in a medium with pH of 1.2 and 2 more hours in a medium with pH of 6.8, at 37° C. Releases for example XXI with particle size distribution between 250 μm and 425 μm (Mesh 40), particle size distribution between 180 μm and 250 μm (Mesh 60), particle size distribution between 125 μm and 180 μm (Mesh 80), and particle size smaller than 125 μm (Mesh 120).

Table 16 illustrates the dissolution release percentages for EXAMPLE XXI with particle size of 425 μm (Mesh 40), 250 μm (Mesh 60), 180 μm (Mesh 80), and 125 μm (Mesh 120):

TABLE 16

| Samples | Time | | | | | | |
|---|---|---|---|---|---|---|---|
| | 30 s % | 60 s % | 120 s % | 1 h % | 2 h % | 3 h % | 4 h % |
| Cocoa Extract | 33.53 | 51.86 | 78.86 | 103.48 | 105.51 | 105.90 | 106.91 |
| 50EXT-30AN7-10L100-10SR-T155-400 RPM-AS73-C2.3-Mesh 40 | 4.95 | 7.12 | 9.88 | 37.50 | 46.64 | 68.50 | 71.54 |
| 50EXT-30AN7-10L100-10SR-T155-400 RPM-AS73-C2.3-Mesh 60 | 5.38 | 8.30 | 15.00 | 42.58 | 45.62 | 72.55 | 75.58 |
| 50EXT-30AN7-10L100-10SR-T155-400 RPM-AS73-C2.3Mesh 80 | 5.54 | 9.88 | 16.97 | 48.67 | 61.86 | 61.43 | 64.46 |
| 50EXT-30AN7-10L100-10SR-T155-400 RPM-AS73-C2.3Mesh 120 | 13.50 | 23.08 | 27.81 | 61.86 | 66.94 | 66.48 | 69.52 |

Example XXII

Chocolate Candy Production Using Nutraceutical Compound 50EPI-30AN7-10L100-10SR-T160-250 rpm-AS70-C2.3—in Mesh 120 for 200 mg of Polyphenols/Unit of Chocolate Candy

TABLE 16

| Ingredients | Lower limit [w/w %] | Upper limit [w/w %] |
| --- | --- | --- |
| Sucrose | 20% | 30% |
| Liquor, solids and Colombian origin cocoa butter | 50% | 55% |
| Essence | 0.1% | 1.0% |
| Nutraceutical compound 10193-120 | 0.2% | 0.4% |

Nutraceutical compound 10193-120 in equivalent to: 50EPI-30AN7-10L100-10SR-T160-250 rpm-AS70-C2.3—in MESH 120—(Example XVIII)

Manufacturing Process of Chocolate Candy:
1. Blending of ingredients (Nutraceutical compound included)
2. Refining process: <30 microns. 22-35° C.
3. Conching process per 24 hours, Rolls temperature: 60° C.
4. Tempering chocolate process
5. Molding chocolate
6. Cooling chocolate
7. Demolding chocolate
8. Packaging chocolate Result of Organoleptic Panel:

Test 1, Good texture, melts well in the mouth, presents creaminess or pleasant fat sensation, good micrage. The total impression is 3, although it is different from the pattern in descriptors. Not significant differences in bitter taste was perceived.

TABLE 17

| Name of product: Chocolate cover 70% |
| --- |
| Test Taste profile |
| Sample preparation Pilot plant. Differences are expected |

| Descriptor | Sample 1 10193-120 Example XXII | Pattern |
| --- | --- | --- |
| Sweet taste | 2.5 | 3 |
| Chocolate taste | 4.5 | 4.5 |
| Bitter taste | 3 | 2.5 |
| Vanilla taste | 0 | 1 |
| Nut taste | 1 | 0 |
| Green taste | 0 | 1.5 |
| Dry grass taste | 1.5 | 0 |
| Fruity taste | 0 | 1 |
| Floral taste | 0 | 1.5 |
| Astringent taste | 2 | 3 |
| Total impression | 3 | 3 |

*Total scale impression or general quality: 1: Low; 2: Medium; 3: High

Figure 42:
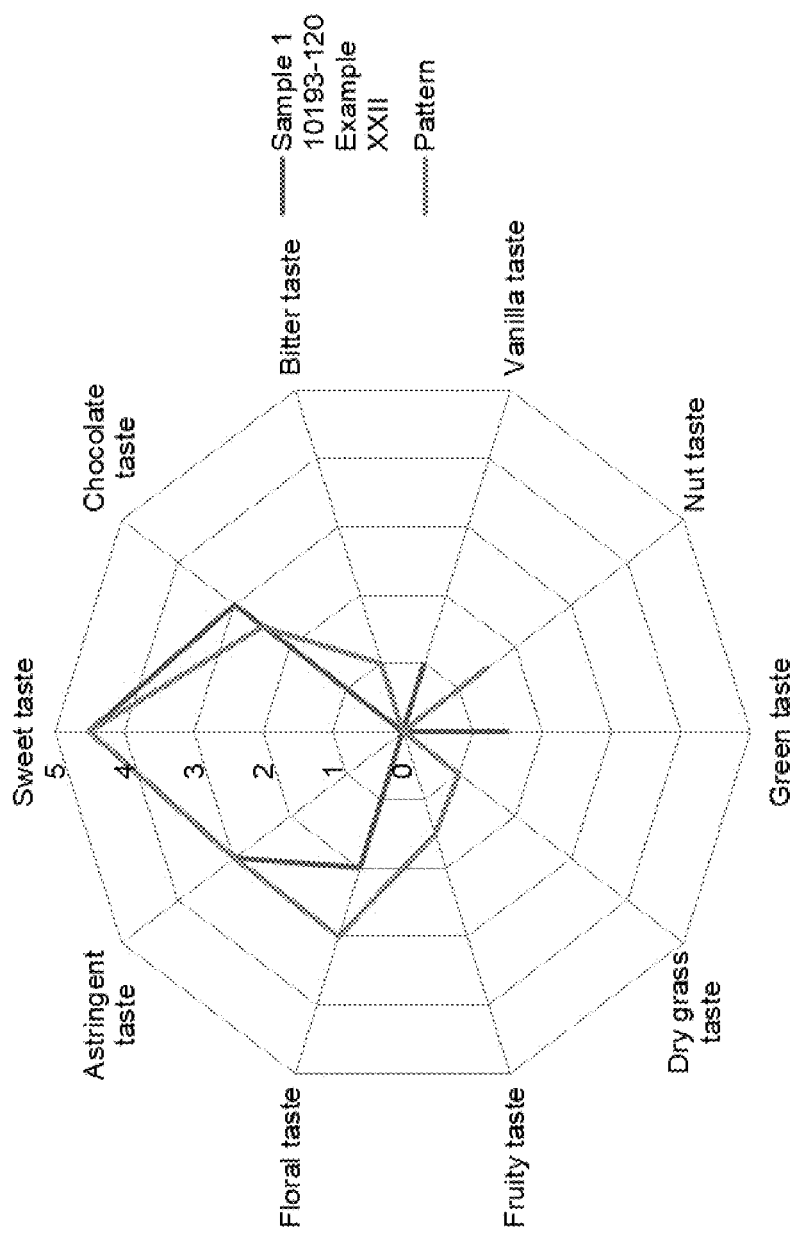
FIG. 42 is a comparative radar graphic for taste profile in chocolate candy evaluated (examples XXII).

FIG. 42 is a comparative radar graphic for taste profile in chocolate candy evaluated (examples XXII)

Example XXIII

Cereal Bar #1 Production Using Nutraceutical Compound 50EPI-30AN7-10L100-10SR-T160-250 rpm-AS70-C2.3—in Mesh 120 for 90 mg of (−)-Epicatechin/Unit of Cereal Bar

| Ingredients | Lower limit [w/w %] | Upper limit [w/w %] |
| --- | --- | --- |
| Binder | 40% | 60% |
| Polysaccharides | | |
| Polyols | | |
| Milk matrix | | |
| Solid | 45% | 55% |
| Assorted cereals | | |
| Nutraceutical compound 10193-120 | 1% | 2% |

Manufacturing Process:

Mixing the ingredients of the binder, and take it to a higher Brix than 50

Mix the binder, with the solid and Nutraceutical compound 10193-120

Formation of the bar. 80-95° C. (Process time: aprox 5 min)

Cooling below 14° C.

Cutting and packaging

Nutraceutical compound 10193-120 in equivalent to: 50EPI-30AN7-10L100-10SR-T160-250rpm-AS70-C2.3—in MESH 120—(Example XVIII)

Result of Organoleptic Panel:

Excess binder, different texture, pale color of the binder. Not significant differences in bitter taste was perceived.

Example XXIV

Cereal Bar #2 Production Using Nutraceutical Compound 50EPI-30AN7-10L100-10SR-T160-250 rpm-AS70-C2.3—in Mesh 40 for 90 mg of (−)-Epicatechin/Unit of Cereal Bar

| | Lower limit [w/w %] | Upper limit [w/w %] |
| --- | --- | --- |
| Binder | 40% | 60% |
| Polysaccharides | | |
| Polyols | | |
| Milk matrix | | |
| Solid | 45% | 55% |
| Assorted cereals | | |
| Nutraceutical compound 10193-40 | 1% | 2% |

Manufacturing process:

Mixing the ingredients of the binder, and take it to a higher Brix than 50

Mix the binder, with the solid and Nutraceutical compound 10193-40

Formation of the bar. 80-95° C. (Process time: aprox 5 min)

Cooling below 14° C.

Cutting and packaging

Nutraceutical compound 10193-40 in equivalent to: 50EPI-30AN7-10L100-10SR-T160-250rpm-AS70-C2.3—in MESH 40—(Example XVIII)

Result of Organoleptic Panel:

Less crispy, lack brightness, has a strange taste (PSH grease—Molding). Not significant differences in bitter taste was perceived.

Example XXV

Cereal Bar #3 Production Using Nutraceutical Compound 50EPI-30ES10-10L100-10SR-T160-270 rpm-AS70-C2.3—in Mesh 120 for 90 mg of (−)-Epicatechin/Unit of Cereal Bar Ingredients

|  | Lower limit [w/w %] | Upper limit [w/w %] |
|---|---|---|
| Binder | 40% | 60% |
| Polysaccharides |  |  |
| Polyols |  |  |
| Milk matrix |  |  |
| Solid | 45% | 55% |
| Assorted cereals |  |  |
| Nutraceutical compound 10195-120 | 1% | 2% |

Manufacturing Process:
Mixing the raw materials of the binder, and take it to a higher Brix than 50
Mix the binder, with the solid and Nutraceutical compound 10195-120
Formation of the bar. 80-95° C. (Process time: aprox 5 min)
Cooling below 14° C.
Cutting and packaging
Nutraceutical compound 10195-120 in equivalent to: 50EPI-30ES10-10L100-10SR-T160-270 rpm-AS70-C2.3—in MESH 120—(Example XIX)
Result of Organoleptic Panel:
Dry, it seems with less binder, more opaque. Not significant differences in bitter taste was perceived.

Example XXVI

Cereal Bar #4 Production Using Nutraceutical Compound 50EPI-30ES10-10L100-10SR-T160-270 rpm-AS70-C2.3—in Mesh 40 for 90 mg of (-)-Epicatechin/Unit of Cereal Bar

| Ingredients | Lower limit [w/w %] | Upper limit [w/w %] |
|---|---|---|
| Binder | 40% | 60% |
| Polysaccharides |  |  |
| Polyols |  |  |
| Milk matrix |  |  |
| Solid | 45% | 55% |
| Assorted cereals |  |  |
| Nutraceutical compound 10195-40 | 1% | 2% |

Manufacturing Process:
Mixing the raw materials of the binder, and take it to a higher Brix than 50
Mix the binder, with the solid and Nutraceutical compound 10195-40
Formation of the bar. 80-95° C. (Process time: aprox 5 min)
Cooling below 14° C.
Cutting and packaging
Nutraceutical compound 10195-40 in equivalent to: 50EPI-30ES10-10L100-10SR-T160-270rpm-AS70-C2.3—in MESH 40—(Example XIX)
Result of Organoleptic Panel:
Texture more similar to the pattern, appearance similar to the pattern, residual flavor, and fatty taste (apparently it is the fat used to portion). Not significant differences in bitter taste was perceived.

Example XXVII

Cereal Bar #5 Production Using Nutraceutical Compound 50EXT-30ES10-10L100-10SR-T155-400 rpm-AS70-C2.3—in Mesh 40 for 90 mg of (-)-Epicatechin/Unit of Cereal Bar

| Ingredients | Lower limit [w/w %] | Upper limit [w/w %] |
|---|---|---|
| Binder | 40% | 60% |
| Polysaccharides |  |  |
| Polyols |  |  |
| Milk matrix |  |  |
| Solid | 45% | 55% |
| Assorted cereals |  |  |
| Nutraceutical compound 10196-40 | 20% | 20% |

Manufacturing process:
Mixing the raw materials of the binder, and take it to a higher Brix than 50
Mix the binder, with the solid and Nutraceutical compound 10196-40
Formation of the bar. 80-95° C. (Process time: aprox 5 min)
Cooling below 14° C.
Cutting and packaging
Nutraceutical compound 10196-40 in equivalent to: 50EXT-30ES10-10L100-10SR-T155-400 rpm-AS70-C2.3—in Mesh 40—(Example XX)
Result of Organoleptic Panel:
Sandy feeling, a lot of particle residue that is not pleasant. Not significant differences in bitter taste was perceived.

Product Name: Cereal Bar
Test name Taste profile
Samples preparation Manufacturing in Pilot Plant. Some differences are expected.

| Descriptor | Sample 1: 10193-40 Example XXIV | Sample 2: 10195-120 Example XXV | Sample 3: 10195-40 Example XXVI | Sample 4: 10196-40 Example XXVII | Sample 5: 10193-120 Example XXIII | Pattern |
|---|---|---|---|---|---|---|
| Salty taste | 0.5 | 0 | 0.5 | 0 | 0 | 1 |
| Sweet taste | 3.5 | 3 | 4 | 3.5 | 4.5 | 4 |
| Dairy taste | 1.5 | 1.5 | 2 | 0 | 1.5 | 2 |
| Bitter taste | 2 | 2 | 2 | 2.5 | 2.5 | 2 |
| Cereal taste | 3 | 3.5 | 3.5 | 3 | 2.5 | 3.5 |
| Toasted taste | 0 | 0 | 0 | 3 | 0 | 0 |
| Caramel taste | 0 | 0 | 0 | 0 | 0 | 0 |
| Total impression | 2 | 2 | 3 | 2 | 2 | 3 |

*Total scale impression or general quality: 1: Low; 2: Medium; 3: High

General Remarks

Sample 1, Less crispy, lack brightness, has a strange taste (PSH grease—Molding)

Sample 2, Dry, it seems with less binder, more opaque.

Sample 3, Texture more similar to the pattern, appearance similar to the pattern, residual flavor, and fatty taste (apparently it is the fat used to portion).

Sample 4, Sandy feeling, a lot of particle residue that is not pleasant.

Sample 5, Excess binder, different texture, pale color of the binder.

Figure 43:
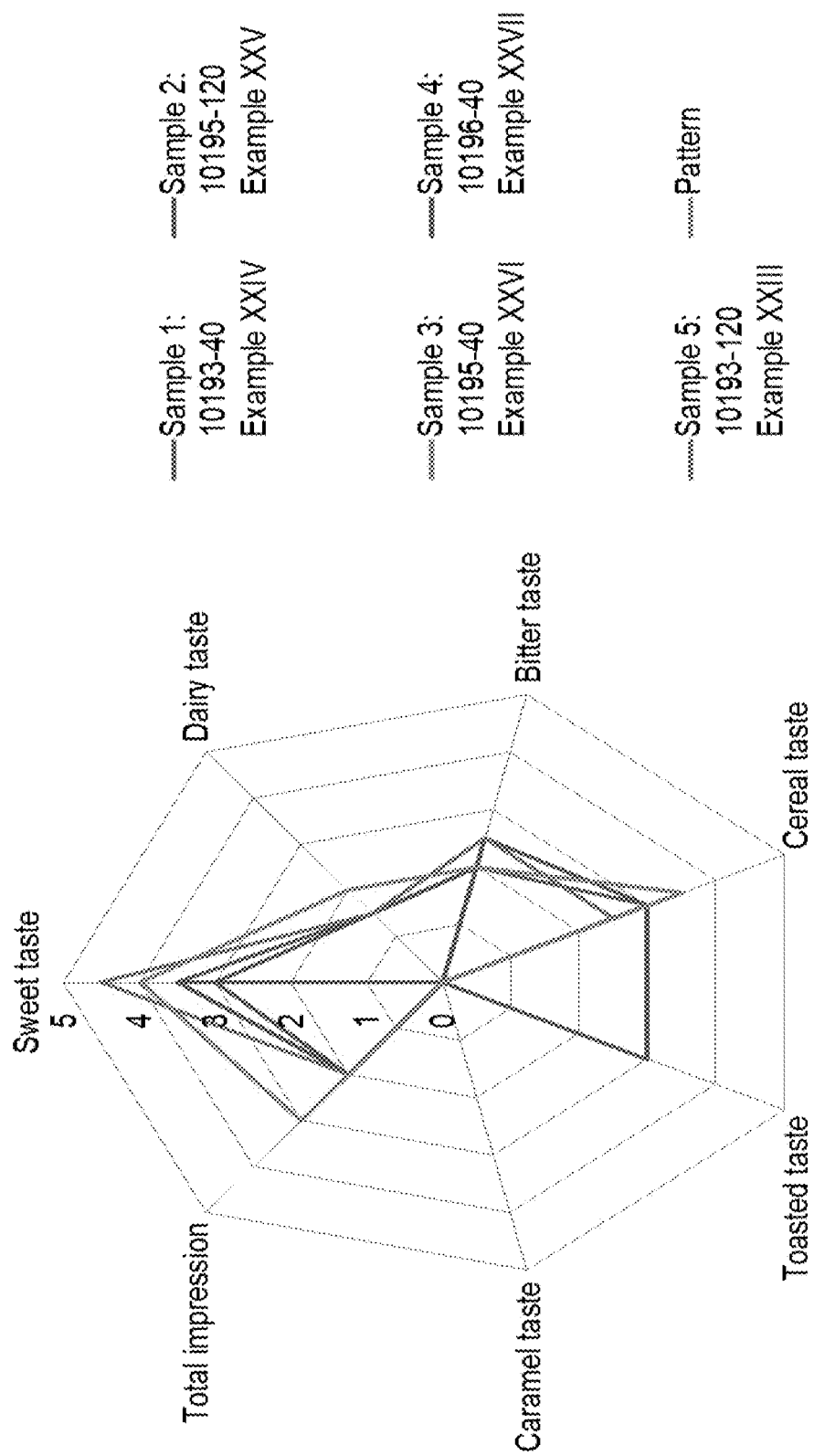
FIG. 43 is comparative radar graphic for taste profile in cereal bars evaluated (examples XXIII, XIV, XV, XVI, XVII).

FIG. 43 is comparative radar graphic for taste profile in cereal bars evaluated (examples XXIII, XIV, XV, XVI, XVII)

Example XXVIII

Screw Configurations (−)-Epicatechin is degraded by light, temperature, residence time and excessive shear.

The possible degradation of the (−)-Epicatechin during extrusion limits the operating conditions of the extruder, and possible screw configurations.

The best suitable screw should have a long feeding zone and short melting zone to control the melt temperature.

Figure 44:
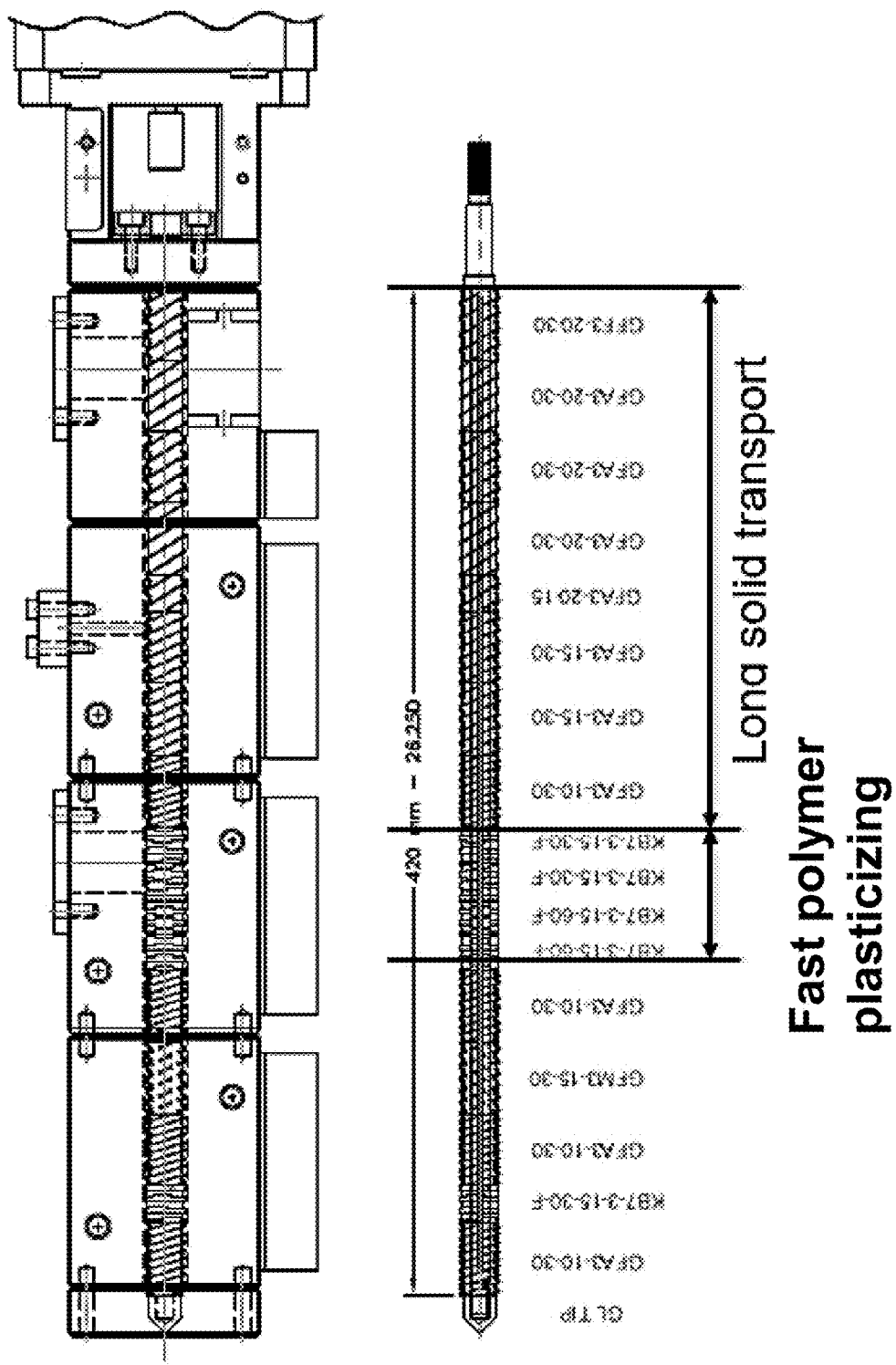
FIGS. 44 and 45 show two possible screw configurations useful for melt extrusion.
Figure 45:
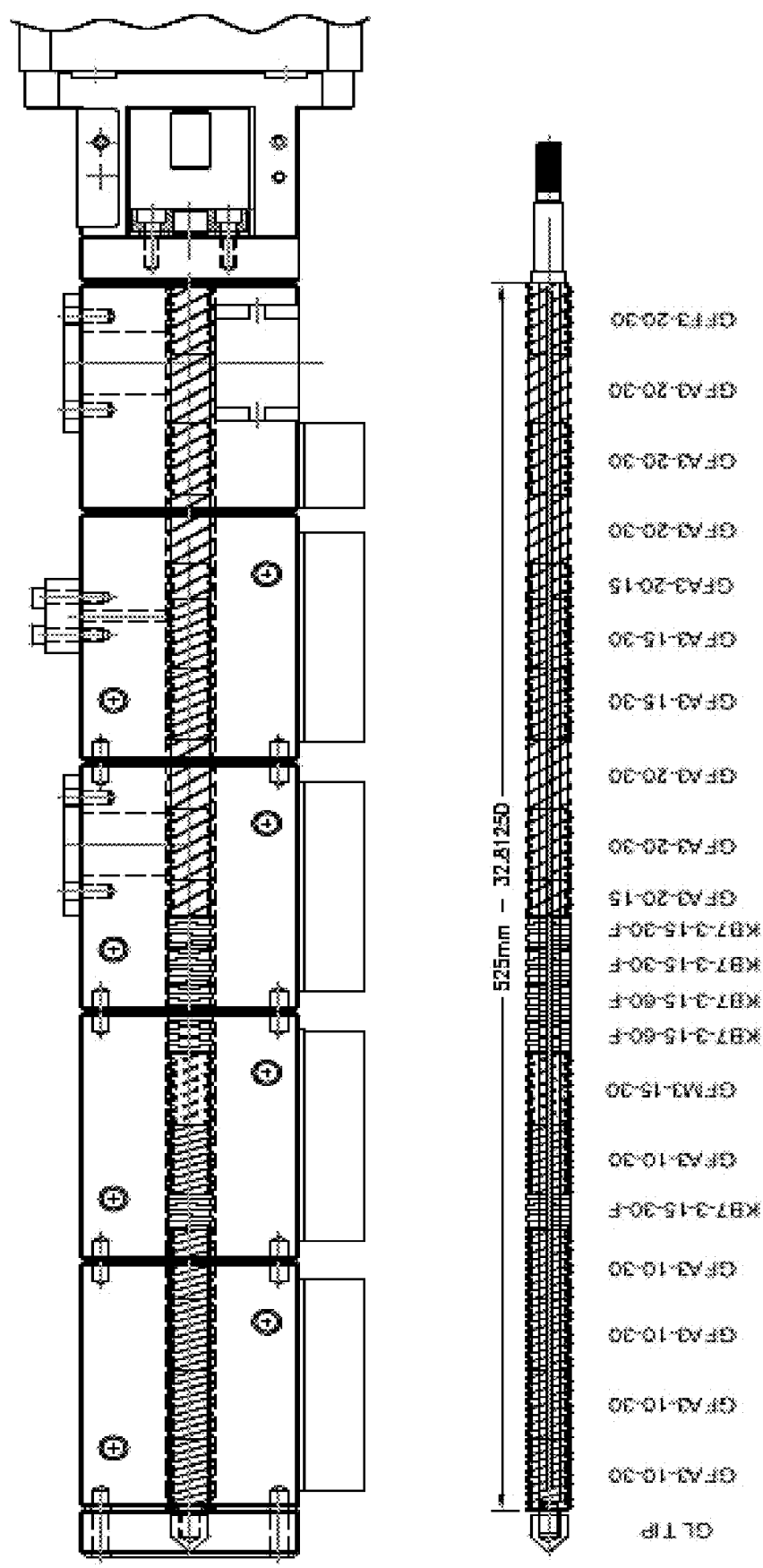

FIGS. 44 and 45 show two possible screw configurations.

Another option could be the use of an additional feeder for the cacao or cocoa extracts or pure (−)-epicatechin. This set up requires two feeders: one for the polymers and one for the extracts. The feeders can be located as demanded by the cocoa or cacao extract. The polymer feeder should be placed close to the main hopper, and the second feeder (cocoa or cacao extract) should be placed after the melting zone.

The temperature profile should deliver a polymer melt below 160° C. as it was shown in the EXAMPLES XVIII, XIX, XX and XXI.

Screw configuration 2.3: D=16 mm, L/D=26.25

Screw Configuration 2.4: D=16 mm, L/D=32.81

With the above screw configurations and the reported operating conditions, the loss of (−)-epicatechin during extrusion was reduced to values below 8.8% wt.: This assessment was measured by HPLC. The physical mixtures were used as reference values (See (−)-Epicatechin content).

| Samples | (−)-Epicatechin Content [% w/w] | EPI Loss in process (% w/w) |
|---|---|---|
| 50EPI-30AN7-10SR-10L100-MESH 120 | 41.3 | 7.6 |
| 50EPI-30ES10-10SR-10L100-MESH 120 | 40.6 | 8.8 |
| 50EPI-30AN7-10SR-10L100 (PHYSICAL MIXTURE) | 44.7 | Reference value |
| 50EPI-30ES10-10SR-10L100 (PHYSICAL MIXTURE) | 44.5 | Reference value |
| EPICATECHIN AT 90% | 85.7 | Reference value |

All patents, patent applications and publications cited in this application including all cited references in those patents, applications and publications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is claimed is:

1. A cocoa extract composition rich in flavonoids consisting essentially of a cocoa extract dispersed by hot melt extrusion or hot melt mixing and encapsulated in polymer matrices selected from the group consisting of:
   (i) a mixture of a polyvinyl caprolactam-polyvinyl acetate-polyethylene glycol graft copolymer with a copolymer of methacrylic acid and methyl methacrylate; and
   (ii) a mixture of ethyl cellulose, polyvinyl acetate-polyvinylpyrrolidone copolymer and a copolymer of methacrylic acid and methyl methacrylate.

* * * * *